United States Patent
Krieg et al.

(10) Patent No.: US 7,795,235 B2
(45) Date of Patent: Sep. 14, 2010

(54) SEMI-SOFT C-CLASS IMMUNOSTIMULATORY OLIGONUCLEOTIDES

(75) Inventors: Arthur M. Krieg, Wellesley, MA (US); Ulrike Samulowitz, Langenfeld (DE); Jörg Vollmer, Düsseldorf (DE); Eugen Uhlmann, Glashuetter (DE)

(73) Assignees: Coley Pharmaceutical GmbH, Dusseldorf (DE); Coley Pharmaceutical Group, Inc., New York, NY (US)

( * ) Notice: Subject to any disclaimer, the term of this patent is extended or adjusted under 35 U.S.C. 154(b) by 0 days.

(21) Appl. No.: 12/336,986

(22) Filed: Dec. 17, 2008

(65) Prior Publication Data

US 2009/0137519 A1    May 28, 2009

Related U.S. Application Data

(62) Division of application No. 11/255,100, filed on Oct. 20, 2005, now Pat. No. 7,566,703.

(60) Provisional application No. 60/620,759, filed on Oct. 20, 2004.

(51) Int. Cl.
    A61K 45/00    (2006.01)
    A61K 38/00    (2006.01)
    A61K 31/70    (2006.01)
    A01N 37/18    (2006.01)

(52) U.S. Cl. .............................. 514/44 R; 514/2; 514/8; 514/12; 424/278.1; 424/279.1

(58) Field of Classification Search ................. None
See application file for complete search history.

(56) References Cited

U.S. PATENT DOCUMENTS

| | | |
|---|---|---|
| 4,806,463 A | 2/1989 | Goodchild et al. |
| 5,004,810 A | 4/1991 | Draper |
| 5,166,195 A | 11/1992 | Ecker |
| 5,194,428 A | 3/1993 | Agrawal et al. |
| 5,264,423 A | 11/1993 | Cohen et al. |
| 5,276,019 A | 1/1994 | Cohen et al. |
| 5,475,096 A | 12/1995 | Gold et al. |
| 5,514,788 A | 5/1996 | Bennett et al. |
| 5,527,899 A | 6/1996 | Froehler |
| 5,587,361 A | 12/1996 | Cook et al. |
| 5,663,153 A | 9/1997 | Hutcherson et al. |
| 5,670,637 A | 9/1997 | Gold et al. |
| 5,696,248 A | 12/1997 | Peyman et al. |
| 5,723,335 A | 3/1998 | Hutcherson et al. |
| 6,031,086 A | 2/2000 | Switzer |
| 6,194,388 B1 | 2/2001 | Krieg et al. |
| 6,207,646 B1 | 3/2001 | Krieg et al. |
| 6,207,819 B1 | 3/2001 | Manoharan et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,348,312 B1 | 2/2002 | Peyman et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,498,148 B1 | 12/2002 | Raz |
| 6,521,637 B2 | 2/2003 | Macfarlane |
| 6,589,940 B1 | 7/2003 | Raz et al. |
| 6,605,708 B1 | 8/2003 | Habus et al. |
| 6,653,292 B1 | 11/2003 | Krieg et al. |
| 6,727,230 B1 | 4/2004 | Hutcherson et al. |
| 6,815,429 B2 | 11/2004 | Agrawal |
| 6,821,957 B2 | 11/2004 | Krieg et al. |
| 6,943,240 B2 | 9/2005 | Bauer et al. |
| 6,949,520 B1 | 9/2005 | Hartmann et al. |
| 6,977,245 B2 | 12/2005 | Klinman et al. |
| 7,001,890 B1 | 2/2006 | Wagner et al. |
| 7,105,495 B2 | 9/2006 | Agrawal et al. |
| 7,108,844 B2 | 9/2006 | Carpentier |
| 7,223,741 B2 | 5/2007 | Krieg |
| 7,262,286 B2 | 8/2007 | Kandimalla et al. |
| 7,271,156 B2 | 9/2007 | Krieg et al. |
| 7,276,489 B2 | 10/2007 | Agrawal et al. |
| 7,354,711 B2 | 4/2008 | Macfarlane |
| 7,402,572 B2 | 7/2008 | Krieg et al. |
| 7,407,944 B2 | 8/2008 | Agrawal et al. |

(Continued)

FOREIGN PATENT DOCUMENTS

EP    0 468 520 A2    1/1992

(Continued)

OTHER PUBLICATIONS

Press Release, Jan. 2007, "Coley Pharmaceutical Group Updates Hepatitis C Drug Development Strategy".

(Continued)

*Primary Examiner*—N. M Minnifield
(74) *Attorney, Agent, or Firm*—Wolf, Greenfield & Sacks, P.C.; Gregg C. Benson

(57) ABSTRACT

The invention relates to specific C-Class semi-soft CpG immunostimulatory oligonucleotides that are useful for stimulating an immune response. In particular the oligonucleotides are useful for treating allergy, such as allergic rhinitis and asthma, cancer and infectious disease, such as hepatitis B and hepatitis C.

5 Claims, 52 Drawing Sheets

U.S. PATENT DOCUMENTS

| | | | |
|---|---|---|---|
| 7,410,975 B2 | 8/2008 | Lipford et al. | |
| 7,488,490 B2 | 2/2009 | Davis et al. | |
| 7,514,415 B2* | 4/2009 | Klinman et al. | 514/44 R |
| 7,517,861 B2* | 4/2009 | Krieg et al. | 514/44 R |
| 7,524,828 B2* | 4/2009 | Krieg et al. | 514/44 R |
| 7,566,703 B2* | 7/2009 | Krieg et al. | 514/44 R |
| 7,569,533 B2* | 8/2009 | SenGupta et al. | 510/417 |
| 7,576,066 B2* | 8/2009 | Krieg | 514/44 R |
| 7,585,847 B2* | 9/2009 | Bratzler et al. | 514/44 R |
| 7,605,138 B2* | 10/2009 | Krieg | 514/44 R |
| 7,615,227 B2* | 11/2009 | Klinman et al. | 424/198.1 |
| 7,615,539 B2* | 11/2009 | Uhlmann et al. | 514/44 R |
| 7,632,822 B2* | 12/2009 | Agrawal et al. | 514/44 R |
| 2001/0044416 A1 | 11/2001 | McCluskie et al. | |
| 2002/0091097 A1 | 7/2002 | Bratzler et al. | |
| 2002/0137714 A1 | 9/2002 | Kandamilla et al. | |
| 2002/0156033 A1 | 10/2002 | Bratzler et al. | |
| 2002/0164341 A1 | 11/2002 | Davis et al. | |
| 2002/0165178 A1 | 11/2002 | Schetter et al. | |
| 2002/0198165 A1 | 12/2002 | Bratzler et al. | |
| 2003/0026782 A1 | 2/2003 | Krieg | |
| 2003/0026801 A1 | 2/2003 | Weiner et al. | |
| 2003/0032443 A1 | 2/2003 | Johnson et al. | |
| 2003/0049266 A1 | 3/2003 | Fearon et al. | |
| 2003/0050263 A1 | 3/2003 | Krieg et al. | |
| 2003/0050268 A1 | 3/2003 | Krieg et al. | |
| 2003/0055014 A1 | 3/2003 | Bratzler | |
| 2003/0091599 A1 | 5/2003 | Davis et al. | |
| 2003/0100527 A1 | 5/2003 | Krieg et al. | |
| 2003/0119773 A1 | 6/2003 | Raz et al. | |
| 2003/0129605 A1 | 7/2003 | Yu et al. | |
| 2003/0148316 A1 | 8/2003 | Lipford et al. | |
| 2003/0148976 A1 | 8/2003 | Krieg et al. | |
| 2003/0166001 A1 | 9/2003 | Lipford | |
| 2003/0175731 A1 | 9/2003 | Fearon et al. | |
| 2003/0181406 A1 | 9/2003 | Schetter et al. | |
| 2003/0186912 A1 | 10/2003 | Agrawal | |
| 2003/0191079 A1 | 10/2003 | Krieg et al. | |
| 2003/0224010 A1 | 12/2003 | Davis et al. | |
| 2003/0232074 A1 | 12/2003 | Lipford et al. | |
| 2003/0232443 A1 | 12/2003 | Bennett et al. | |
| 2004/0006034 A1 | 1/2004 | Raz et al. | |
| 2004/0009949 A1 | 1/2004 | Krieg | |
| 2004/0030118 A1 | 2/2004 | Wagner et al. | |
| 2004/0053880 A1 | 3/2004 | Krieg | |
| 2004/0058883 A1 | 3/2004 | Phillips et al. | |
| 2004/0067902 A9 | 4/2004 | Bratzler et al. | |
| 2004/0067905 A1 | 4/2004 | Krieg | |
| 2004/0087534 A1 | 5/2004 | Krieg et al. | |
| 2004/0087538 A1 | 5/2004 | Krieg et al. | |
| 2004/0092472 A1 | 5/2004 | Krieg | |
| 2004/0106568 A1 | 6/2004 | Krieg et al. | |
| 2004/0131628 A1 | 7/2004 | Bratzler et al. | |
| 2004/0132677 A1 | 7/2004 | Fearon et al. | |
| 2004/0132685 A1 | 7/2004 | Krieg et al. | |
| 2004/0136948 A1 | 7/2004 | Fearon et al. | |
| 2004/0142469 A1 | 7/2004 | Krieg et al. | |
| 2004/0143112 A1 | 7/2004 | Krieg et al. | |
| 2004/0147468 A1 | 7/2004 | Krieg et al. | |
| 2004/0152649 A1 | 8/2004 | Krieg | |
| 2004/0152656 A1 | 8/2004 | Krieg et al. | |
| 2004/0152657 A1 | 8/2004 | Krieg et al. | |
| 2004/0162258 A1 | 8/2004 | Krieg et al. | |
| 2004/0162262 A1 | 8/2004 | Krieg et al. | |
| 2004/0167089 A1 | 8/2004 | Krieg et al. | |
| 2004/0171150 A1 | 9/2004 | Krieg et al. | |
| 2004/0171571 A1 | 9/2004 | Krieg et al. | |
| 2004/0181045 A1 | 9/2004 | Krieg et al. | |
| 2004/0198680 A1 | 10/2004 | Krieg | |
| 2004/0198688 A1 | 10/2004 | Krieg et al. | |
| 2004/0229835 A1 | 11/2004 | Krieg et al. | |
| 2004/0234512 A1 | 11/2004 | Wagner et al. | |
| 2004/0235770 A1 | 11/2004 | Davis et al. | |
| 2004/0235774 A1 | 11/2004 | Bratzler et al. | |
| 2004/0235777 A1 | 11/2004 | Wagner et al. | |
| 2004/0235778 A1 | 11/2004 | Wagner et al. | |
| 2004/0266719 A1 | 12/2004 | McCluskie et al. | |
| 2005/0004061 A1 | 1/2005 | Krieg et al. | |
| 2005/0004062 A1 | 1/2005 | Krieg et al. | |
| 2005/0009774 A1 | 1/2005 | Krieg et al. | |
| 2005/0032734 A1 | 2/2005 | Davis et al. | |
| 2005/0032736 A1 | 2/2005 | Krieg et al. | |
| 2005/0037403 A1 | 2/2005 | Krieg et al. | |
| 2005/0037985 A1 | 2/2005 | Krieg et al. | |
| 2005/0043529 A1 | 2/2005 | Davis et al. | |
| 2005/0049215 A1 | 3/2005 | Krieg et al. | |
| 2005/0049216 A1 | 3/2005 | Krieg et al. | |
| 2005/0054601 A1 | 3/2005 | Wagner et al. | |
| 2005/0054602 A1 | 3/2005 | Krieg et al. | |
| 2005/0059619 A1 | 3/2005 | Krieg et al. | |
| 2005/0059625 A1 | 3/2005 | Krieg et al. | |
| 2005/0070491 A1 | 3/2005 | Krieg et al. | |
| 2005/0075302 A1 | 4/2005 | Hutcherson et al. | |
| 2005/0100983 A1 | 5/2005 | Bauer et al. | |
| 2005/0101554 A1 | 5/2005 | Krieg et al. | |
| 2005/0101557 A1 | 5/2005 | Krieg et al. | |
| 2005/0119273 A1 | 6/2005 | Lipford et al. | |
| 2005/0123523 A1 | 6/2005 | Krieg et al. | |
| 2005/0130911 A1 | 6/2005 | Uhlmann et al. | |
| 2005/0130918 A1 | 6/2005 | Agrawal et al. | |
| 2005/0148537 A1 | 7/2005 | Krieg et al. | |
| 2005/0169888 A1 | 8/2005 | Hartmann et al. | |
| 2005/0171047 A1 | 8/2005 | Krieg et al. | |
| 2005/0181422 A1 | 8/2005 | Bauer et al. | |
| 2005/0182017 A1 | 8/2005 | Krieg | |
| 2005/0197314 A1 | 9/2005 | Krieg et al. | |
| 2005/0215501 A1 | 9/2005 | Lipford et al. | |
| 2005/0233995 A1 | 10/2005 | Krieg et al. | |
| 2005/0233999 A1 | 10/2005 | Krieg et al. | |
| 2005/0239732 A1 | 10/2005 | Krieg et al. | |
| 2005/0239733 A1 | 10/2005 | Jurk et al. | |
| 2005/0239734 A1 | 10/2005 | Uhlmann et al. | |
| 2005/0239736 A1 | 10/2005 | Krieg et al. | |
| 2005/0244379 A1 | 11/2005 | Krieg et al. | |
| 2005/0244380 A1 | 11/2005 | Krieg et al. | |
| 2005/0245477 A1 | 11/2005 | Krieg et al. | |
| 2005/0250726 A1 | 11/2005 | Krieg et al. | |
| 2005/0256073 A1 | 11/2005 | Lipford et al. | |
| 2005/0266015 A1 | 12/2005 | Clerici et al. | |
| 2005/0267064 A1 | 12/2005 | Krieg et al. | |
| 2005/0277604 A1 | 12/2005 | Krieg et al. | |
| 2005/0277609 A1 | 12/2005 | Krieg et al. | |
| 2006/0003955 A1 | 1/2006 | Krieg et al. | |
| 2006/0014713 A1 | 1/2006 | Agrawal et al. | |
| 2006/0019916 A1 | 1/2006 | Krieg et al. | |
| 2006/0019918 A1 | 1/2006 | Agrawal et al. | |
| 2006/0019923 A1 | 1/2006 | Davis et al. | |
| 2006/0058251 A1 | 3/2006 | Krieg et al. | |
| 2006/0058254 A1 | 3/2006 | Dina et al. | |
| 2006/0074040 A1 | 4/2006 | Kandimalla et al. | |
| 2006/0089326 A1 | 4/2006 | Krieg et al. | |
| 2006/0094683 A1 | 5/2006 | Krieg et al. | |
| 2006/0140875 A1 | 6/2006 | Krieg et al. | |
| 2006/0154890 A1 | 7/2006 | Bratzler et al. | |
| 2006/0172966 A1 | 8/2006 | Lipford et al. | |
| 2006/0188913 A1 | 8/2006 | Krieg et al. | |
| 2006/0211639 A1 | 9/2006 | Bratzler et al. | |
| 2006/0211644 A1 | 9/2006 | Krieg et al. | |
| 2006/0229271 A1 | 10/2006 | Krieg et al. | |
| 2006/0241076 A1 | 10/2006 | Uhlmann et al. | |
| 2006/0246035 A1 | 11/2006 | Ahluwalia et al. | |
| 2006/0286070 A1 | 12/2006 | Hartmann et al. | |
| 2006/0287263 A1 | 12/2006 | Davis et al. | |
| 2007/0009482 A9 | 1/2007 | Krieg et al. | |

| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0093439 A1 | 4/2007 | Agrawal et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0226649 A1 | 9/2008 | Schetter et al. |
| 2009/0017021 A1 | 1/2009 | Davis et al. |
| 2009/0060927 A1 | 3/2009 | Wagner et al. |

FOREIGN PATENT DOCUMENTS

| WO | WO 98/49288 A1 | 11/1998 |
| WO | WO 99/56755 A1 | 11/1999 |
| WO | WO 00/06588 A1 | 2/2000 |
| WO | WO 00/14217 A2 | 3/2000 |
| WO | WO 00/67023 A1 | 11/2000 |
| WO | WO 00/67787 A2 | 11/2000 |
| WO | WO 03/015711 A2 | 2/2003 |
| WO | WO 03/035836 A2 | 5/2003 |
| WO | WO 2004/005476 A2 | 1/2004 |
| WO | WO 2004/007743 A2 | 1/2004 |
| WO | WO 2004/016805 A2 | 2/2004 |
| WO | WO 2004/026888 A2 | 4/2004 |
| WO | WO 2004/039829 A2 | 5/2004 |
| WO | WO 2004/053104 A2 | 6/2004 |
| WO | WO 2004/087203 A2 | 10/2004 |
| WO | WO 2004/094671 A2 | 11/2004 |
| WO | WO 2006/110607 A2 | 10/2006 |
| WO | WO 2006/134423 A2 | 12/2006 |
| WO | WO 2006/135434 A2 | 12/2006 |
| WO | WO 2007/095316 A2 | 8/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 A2 | 6/2008 |
| WO | WO 2008/139262 A2 | 11/2008 |

OTHER PUBLICATIONS

Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".
Press Release, Hybridon, Inc. Hybridon shows immonumodulatory activity of synthetic oligonucleotides. Cambrige, MA. May 7, 2001.
Agrawal et al., Pharmacokinetics of oligonucleotides. Ciba Found Symp. 1997;209:60-75; discussion 75-8.
Agrawal et al., Novel immunomodulatory oligonucleotides prevent development of allergic airway inflammation and airway hyperresponsiveness in asthma. Int Immunopharmacol. Jan. 2004;4(1):127-38.
Agrawal et al., Pharmacokinetics, biodistribution, and stability of oligodeoxynucleotide phosphorothioates in mice. Proc Natl Acad Sci U S A. Sep. 1, 1991;88(17):7595-9.
Agrawal et al., Medicinal chemistry and therapeutic potential of CpG DNA. Trends Mol Med. Mar. 2002;8(3):114-21.
Agrawal et al., Pharmacokinetics of antisense oligonucleotides. Clin Pharmacokinet. Jan. 1995;28(1):7-16.
Ahluwalia et al., Immunostimulatiory progiles from two classes of CpG ODN administered subcutaneously to healthy subjects. ICI FOCIS 2004. Poster.
Ammerpohl et al., Complex protein binding to the mouse M-lysozyme gene downstream enhancer involves single-stranded DNA binding. Gene. Oct. 24, 1997;200(1-2):75-84.
An et al., Isoforms of the EP3 subtype of human prostaglandin E2 receptor transduce both intracellular calcium and cAMP signals. Biochemistry. Dec. 6, 1994;33(48):14496-502.
Anderson et al., Selective inhibition of cyclooxygenase (COX)-2 reverses inflammation and expression of COX-2 and interleukin 6 in rat adjuvant arthritis. J Clin Invest. Jun. 1, 1996;97(11):2672-9.
Asadullah et al., IL-10 is a key cytokine in psoriasis. Proof of principle by IL-10 therapy: a new therapeutic approach. J Clin Invest. Feb. 15, 1998;101(4):783-94.
Bhagat et al., CpG penta- and hexadeoxyribonucleotides as potent immunomodulatory agents. Biochem Biophys Res Commun. Jan. 24, 2003;300(4):853-61.
Blaxter et al., Genes expressed in *Brugia malayi* infective third stage larvae. Mol Biochem Parasitol. Apr. 1996;77(1):77-93.
Cooper et al., Safety and immunogenicity of CPG 7909 injection as an adjuvant to Fluarix influenza vaccine. Vaccine. Aug. 13, 2004;22(23-24):3136-43.
Cox et al., Isolation of an Alu repetitive DNA binding protein and effect of CpG methylation on binding to its recognition sequence. Biochim Biophys Acta. Mar. 4, 1998;1396(1):67-87.
Crooke et al., Phosphorothioate Oligonucleotides. Therapeut Apps. 1995;Ch. 5:63-84.
Dalpke et al., CpG-DNA as immune response modifier. Int J Med Microbiol. Oct. 2004;294(5):345-54.
Dar et al., Attenuated cytokine responses in porcine lymph node cells stimulated with CpG DNA are associated with low frequency of IFNalpha-producing cells and TLR9 mRNA expression. Vet Immunol Immunopathol. Jun. 15, 2008;123(3-4):324-36. Epub Feb. 17, 2008.
Filion et al., Development of immunomodulatory six base-length non-CpG motif oligonucleotides for cancer vaccination. Vaccine, Jun. 23, 2004;22(19):2480-8.
Goldberg et al., Beyond danger: unmethylated CpG dinucleotides and the immunopathogenesis of disease. Immunol Lett. Jul. 3, 2000;73(1):13-8.
Hartmann et al., Delineation of a CpG phosphorothioate oligodeoxynucleotide for activating primate immune responses in vitro and in vivo. J Immunol. Feb. 1, 2000;164(3):1617-24.
Hartmann et al., Rational design of new CpG oligonucleotides that combine B cell activation with high IFN-alpha induction in plasmacytoid dendritic cells. Eur J. Immunol. Jun. 2003;33(6):1633-41.
Heeg et al., CpG DNA as a Th1 trigger. Int Arch Allergy Immunol. Feb. 2000;121(2):87-97.
Iho et al., Oligodeoxynucleotides containing palindrome sequences with internal 5'-CpG-3' act directly on human NK and activated T cells to induce IFN-gamma production in vitro. J Immunol. Oct. 1, 1999;163(7):3642-52.
Jiang et al., Enhancing immunogenicity by CpG DNA. Curr Opin Mol Ther. Apr. 2003;5(2):180-5.
Juffermans et al., CpG oligodeoxynucleotides enhance host defense during murine tuberculosis. Infect Immun. Jan. 2002;70(1):147-52.
Jurk et al., C-Class CpG ODN: sequence requirements and characterization of immunostimulatory activities on mRNA level. Immunobiology. 2004;209(1-2):141-54.
Kandimalla et al., Towards optimal design of second-generation immunomodulatory oligonucleotides. Curr Opin Mol Ther. Apr. 2002;4(2):122-9.
Kandimalla et al., Divergent synthetic nucleotide motif recognition pattern: design and development of potent immunomodulatory oligodeoxyribonucleotide agents with distinct cytokine induction profiles. Nucleic Acids Res. May 1, 2003;31(9):2393-400.
Kandimalla et al., Secondary structures in CpG oligonucleotides affect immunostimulatory activity. Biochem Biophys Res Commun. Jul. 11, 2003;306(4):948-53.
Klinman et al., Immunotherapeutic uses of CpG oligodeoxynucleotides. Nat Rev Immunol. Apr. 2004;4(4):249-58.
Krieg at al., Immune effects and therapeutic applications of CpG motifs in bacterial DNA. Immunopharmacology. Jul. 25, 2000;48(3):303-5.

Krieg et al., Lymphocyte activation mediated by oligodeoxynucleotides or DNA containing novel un-methylated CpG motifs. American College of Rheumatology 58th National Scientific Meeting. Minneapolis, Minnesota, Oct. 22, 1994. Abstracts. Arthritis Rheum. Sep. 1994;37(9 Suppl).

Krieg et al., CpG motifs in bacterial DNA trigger direct B-cell activation. Nature. Apr. 6, 1995;374(6522):546-9.

Krieg et al., The role of CpG dinucleotides in DNA vaccines. Trends Microbiol. Jan. 1998;6(1):23-7.

Krieg et al., Causing a commotion in the blood: immunotherapy progresses from bacteria to bacterial DNA. Immunol Today. Oct. 2000;21(10):521-6.

Krieg et al., P-chirality-dependent immune activation by phosphorothioate CpG oligodeoxynucleotides. Oligonucleotides. 2003;13(6):491-9.

Krieg, Immune effects and mechanisms of action of CpG motifs. Vaccine. Nov. 8, 2001;19(6):618-22.

Krieg, The role of CpG motifs in innate immunity. Curr Opin Immunol. Feb. 2000;12(1):35-43.

Krieg et al., Mechanism of action of CpG DNA. Curr Top Microbiol Immunol. 2000;247:1-21.

Krieg, Therapeutic potential of Toll-like receptor 9 activation. Nat Rev Drug Discov. Jun. 2006;5(6):471-84.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71.

Krieg, Now I know my CpGs.Trends Microbiol. Jun. 2001;9(6):249-52.

Kuramoto et al., Induction of T-cell-mediated immunity against MethA fibrosarcoma by intratumoral injections of a *Bacillus* Calmette-Guerin nucleic acid fraction. Cancer Immunol Immunother. 1992;34(5):283-8.

Lipford et al., Bacterial DNA as immune cell activator. Trends Microbiol. Dec. 1998;6(12):496-500.

Loke et al., Delivery of c-myc antisense phosphorothioate oligodeoxynucleotides to hematopoietic cells in culture by liposome fusion: specific reduction in c-myc protein expression correlates with inhibition of cell growth and DNA synthesis. Curr Top Microbiol Immunol. 1988;141:282-9.

Lyer et al., Modified oligonucleotides—synthesis, properties and applications. Curr Opin Mol Ther. Jun. 1999;1(3):344-58. Review. No abstract available.

Mackellar et al., Synthesis and physical properties of anti-HIV antisense oligonucleotides bearing terminal lipophilic groups. Nucleic Acids Res. Jul. 11, 1992;20(13):3411-7.

Marshall et al., Identification of a novel CpG DNA class and motif that optimally stimulate B cell and plasmacytoid dendritic cell functions. J Leukoc Biol. Jun. 2003;73(6):781-92.

Marshall et al., Superior activity of the type C class of ISS in vitro and in vivo across multiple species. DNA Cell Biol. Feb. 2005;24(2):63-72.

McCluskie et al., The use of CpG DNA as a mucosal vaccine adjuvant. Curr Opin Investig Drugs. Jan. 2001;2(1):35-9.

McIntyre et al., A sense phosphorothioate oligonucleotide directed to the initiation codon of transcription factor NF-kappa B p65 causes sequence-specific immune stimulation. Antisense Res Dev. 1993 Winter;3(4):309-22.

Messina et al., The influence of DNA structure on the in vitro stimulation of murine lymphocytes by natural and synthetic polynucleotide antigens. Cell Immunol. Mar. 1993;147(1):148-57.

Mojcik et al., Administration of a phosphorothioate oligonucleotide antisense to murine endogenous retroviral MCF env causes immune effects in vivo in a sequence-specific manner. Clin Immunol Immunopathol. May 1993;67(2):130-6.

Mutwiri et al., Strategies for enhancing the immunostimulatory effects of CpG oligodeoxynucleotides. J Control Release. May 31, 2004;97(1):1-17.

Nichani et al., Systemic innate immune responses following intrapulmonary delivery of CpG oligodeoxynucleotides in sheep. Vet Immunol Immunopathol. Feb. 15, 2007;115(3-4):357-68. Epub Dec. 1, 2006.

Nyce et al., DNA antisense therapy for asthma in an animal model. Nature. Feb. 20, 1997;385(6618):721-5.

Perlaky et al., Growth inhibition of human tumor cell lines by antisense oligonucleotides designed to inhibit p120 expression. Anticancer Drug Des. Feb. 1993;8(1):3-14.

Pisetsky et al., Influence of backbone chemistry on immune activation by synthetic oligonucleotides. Biochem Pharmacol. Dec. 15, 1999;58(12):1981-8.

Pisetsky et al., Stimulation of murine lymphocyte proliferation by a phosphorothioate oligonucleotide with antisense activity for herpes simplex virus. Life Sci. 1994;54(2):101-7.

Pisetsky et al., Stimulation of in vitro proliferation of murine lymphocytes by synthetic oligodeoxynucleotides. Mol Biol Rep. Oct. 1993;18(3):217-21.

Pisetsky, The influence of base sequence on the immunostimulatory properties of DNA. Immunol Res. 1999;19(1):35-46.

Polanczyk et al., Immunostimulatory effects of DNA and CpG motifs. Cent Eur J of Immunol. 2000;25(3):160-6.

Rankin et al., CpG motif identification for veterinary and laboratory species demonstrates that sequence recognition is highly conserved. Antisense Nucleic Acid Drug Dev. Oct. 2001;11(5):333-40.

Satoh et al., The study of mechanisms in CpG oligodeoxynucleotides-induced aggravation in murine allergic contact dermititis to 2,4-dinitrofluorobenzene. Fukushima Igaku Zasshi. 2002;52(3):237-50, Abstract only.

Say et al., Synthesis and biological activities of 2-arylquinolin-4-amines. Dissertation Abstracts International. 2001;68(8B):3629.

Scheule, The role of CpG motifs in immunostimulation and gene therapy. Adv Drug Deliv Rev. Nov. 15, 2000;44(2-3):119-34.

Stein et al., Problems in interpretation of data derived from in vitro and in vivo use of antisense oligodeoxynucleotides, Antisense Res Dev. 1994 Summer;4(2):67-9.

Stein et al., Non-antisense effects of oligodeoxynucleotides. Antisense Technology. 1997; ch11: 241-64.

Storey et al., Anti-sense phosphorothioate oligonucleotides have both specific and non-specific effects on cells containing human papillomavirus type 16. Nucleic Acids Res. Aug. 11, 1991;19(15):4109-14.

Tam et al., Liposomal encapsulation enhances the activity of immunostimulatory oligonucleotides. Future Lipidology. Feb. 2006; 1(1): 35-46.

Threadgill et al., Mitogenic synthetic polynucleotides suppress the antibody response to a bacterial polysaccharide. Vaccine. Jan. 1998;16(1):76-82.

Tokunaga et al., A synthetic single-stranded DNA, poly(dG,dC), induces interferon-alpha/beta and -gamma, augments natural killer activity, and suppresses tumor growth. Jpn J Cancer Res. Jun. 1988;79(6):682-6.

Tokunaga, Response of the organism to DNA—With a focus on immunostimulatory DNA. Kansen Ensho Meneki. 2001 Autumn; 31(3): 1-12. Japanese.

Uhlmann et al., Recent advances in the development of immunostimulatory oligonucleotides. Curr Opin Drug Discov Devel. Mar. 2003;6(2):204-17.

Vollmer et al., Characterization of three CpG oligodeoxynucleotide classes with distinct immunostimulatory activities. Eur J Immunol. Jan. 2004;34(1):251-62.

Vollmer et al., Impact of modifications of heterocyclic bases in CpG dinucleotides on their immune-modulatory activity. J Leukoc Biol. Sep. 2004;76(3):585-93. Epub Jun. 24, 2004.

Vollmer, CpG motifs to modulate innate and adaptive immune responses. Int Rev Immunol. May-Aug. 2006;25(3-4):125-34.

Vollmer, TLR9 in health and disease. Int Rev Immunol. May-Aug. 2006;25(3-4):155-81.

Vollmer et al., Identification of a new class of CpG oligonucleotides capapble of inducing both B cell proliferation and hihg IFN-alpha secretion from PBMC of HCV chronic carriers. Antiv Ther. 2002;7:L115.

Wang et al., Immunomodulatory oligonucleotides as novel therapy for breast cancer: pharmacokinetics, in vitro and in vivo anticancer activity, and potentiation of antibody therapy. Mol Cancer Ther. Aug. 2006;5(8):2106-14.

Wang et al., Synthetic oligodeoxynucleotides containing deoxycytidyl-deoxyguanosine dinucleotides (CpG ODNs) and modified analogs as novel anticancer therapeutics. Curr Pharm Des. 2005;11(22):2889-907.

Wilson et al., Immune mechanisms and therapeutic potential of CpG oligodeoxynucleotides. Int Rev Immunol. May-Aug. 2006;25(3-4):183-213. Review.

Yamamoto et al., Ability of oligonucleotides with certain palindromes to induce interferon production and augment natural killer cell activity is associated with their base length. Antisense Res Dev. 1994 Summer;4(2):119-22.

Yamamoto et al., Synthetic oligonucleotides with certain palindromes stimulate interferon production of human peripheral blood lymphocytes in vitro. Jpn J Cancer Res. Aug. 1994;85(8):775-9.

Yu et al., 'Immunomers'—novel 3'-3'-linked CpG oligodeoxyribonucleotides as potent immunomodulatory agents. Nucleic Acids Res. Oct. 15, 2002;30(20):4460-9.

Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.

Zhao et al., Effect of different chemically modified oligodeoxynucleotides on immune stimulation. Biochem Pharmacol. Jan. 26, 1996;51(2):173-82.

Zimmermann et al., Immunostimulatory DNA as adjuvant: efficacy of phosphodiester CpG oligonucleotides is enhanced by 3' sequence modifications. Vaccine. Feb. 14, 2003;21(9-10):990-5.

* cited by examiner

One-way Analysis of Variance (ANOVA)

The P value is 0.0032, considered very significant.
Variation among column means is significantly greater than expected by chance.

Dunnett Multiple Comparisons Test

Control column: OVA
If the value of q is greater than 2.632 then the P value is less than 0.05.

| Comparison | | Mean Difference | q | P value |
|---|---|---|---|---|
| OVA vs SAL | | 6783.6 | 4.311 | ** P<0.01 |
| OVA vs | 10upk | 1943.2 | 1.191 | ns P>0.05 |
| OVA vs SEQ ID | 30upk | 3482.7 | 2.134 | ns P>0.05 |
| OVA vs NO:7 | 100upk | 2900.9 | 1.700 | ns P>0.05 |
| OVA vs | 300upk | 5095.1 | 2.986 | * P<0.05 |

| Difference | | Mean Difference | Lower 95% CI | Upper 95% CI |
|---|---|---|---|---|
| OVA - SAL | | 6783.6 | 2642.4 | 10925 |
| OVA | -10upk | 1943.2 | -2351.8 | 6238.1 |
| OVA SEQ ID | -30upk | 3482.7 | -812.18 | 7777.6 |
| OVA NO:7 | -100upk | 2900.9 | -1590.8 | 7392.7 |
| OVA | -300upk | 5095.1 | 603.3 | 9586.8 |

Assumption test: Are the standard deviations of the groups equal?

Fig. 23A

One-way Analysis of Variance (ANOVA)

The P value is 0.0001, considered extremely significant.
Variation among column means is significantly greater than expected by chance.

Dunnett Multiple Comparisons Test

Control column: OVA
If the value of q is greater than 2.632 then the P value is less than 0.05.

| Comparison | | Mean Difference | q | P value |
|---|---|---|---|---|
| OVA vs SAL | | 344.57 | 5.770 | ** P<0.01 |
| OVA vs | 10upk | 135.02 | 2.180 | ns P>0.05 |
| OVA vs SEQ ID | 30upk | 133.59 | 2.157 | ns P>0.05 |
| OVA vs NO:7 | 100upk | 81.278 | 1.255 | ns P>0.05 |
| OVA vs | 300upk | 142.28 | 2.197 | ns P>0.05 |

| Difference | | Mean Difference | Lower 95% CI | Upper 95% CI |
|---|---|---|---|---|
| OVA - SAL | | 344.57 | 187.41 | 501.73 |
| OVA - | -10upk | 135.02 | -27.982 | 298.01 |
| OVA - SEQ ID | -30upk | 133.59 | -29.410 | 296.58 |
| OVA - NO:7 | -100upk | 81.278 | -89.189 | 251.74 |
| OVA - | -300upk | 142.28 | -28.189 | 312.74 |

Assumption test: Are the standard deviations of the groups equal?

Fig. 23B

One-way Analysis of Variance (ANOVA)

The P value is < 0.0001, considered extremely significant.
Variation among column means is significantly greater than expected by chance.

Dunnett Multiple Comparisons Test

Control column: OVA
If the value of q is greater than 2.620 then the P value is less than 0.05.

| Comparison | | Mean Difference | q | P value |
|---|---|---|---|---|
| OVA vs SAL | | 6783.6 | 6.220 | ** P<0.01 |
| OVA vs | -10upk | 5140.3 | 4.346 | ** P <0.01 |
| OVA vs SEQ ID | -30upk | 4723.6 | 4.176 | ** P <0.01 |
| OVA vs NO:2 | -100upk | 4100.3 | 3.760 | ** P <0.01 |
| OVA vs | -300upk | 3032.2 | 2.780 | * P <0.05 |

| Difference | | Mean Difference | Lower 95% CI | Upper 95% CI |
|---|---|---|---|---|
| OVA - SAL | | 6783.6 | 3926.4 | 9640.8 |
| OVA - | -10upk | 5140.3 | 2041.2 | 8239.3 |
| OVA - SEQ ID | -30upk | 4723.6 | 1760.3 | 7686.8 |
| OVA - NO:2 | -100upk | 4100.3 | 1243.1 | 6957.5 |
| OVA - | -300upk | 3032.2 | 175.01 | 5889.4 |

Assumption test: Are the standard deviations of the groups equal?

Fig. 25A

One-way Analysis of Variance (ANOVA)

The P value is 0.0003, considered extremely significant.
Variation among column means is significantly greater than expected by chance.

Dunnett Multiple Comparisons Test

Control column: OVA
If the value of q is greater than 2.620 then the P value is less than 0.05.

| Comparison | Mean Difference | q | P value | |
|---|---|---|---|---|
| OVA vs SAL | 344.57 | 4.854 | ** | P <0.01 |
| OVA vs SEQ ID NO:2 -10upk | 217.61 | 2.826 | * | P <0.05 |
| OVA vs SEQ ID NO:2 -30upk | 151.02 | 2.051 | ns | P >0.05 |
| OVA vs SEQ ID NO:2 -100upk | 137.94 | 1.943 | ns | P >0.05 |
| OVA vs SEQ ID NO:2 -300upk | 35.569 | 0.5011 | ns | P >0.05 |

| Difference | Mean Difference | Lower 95% CI | Upper 95% CI |
|---|---|---|---|
| OVA - SAL | 344.57 | 158.59 | 530.55 |
| OVA - SEQ ID NO:2 -10upk | 217.61 | 15.892 | 419.33 |
| OVA - SEQ ID NO:2 -30upk | 151.02 | -41.864 | 343.90 |
| OVA - SEQ ID NO:2 -100upk | 137.94 | -48.031 | 323.92 |
| OVA - SEQ ID NO:2 -300upk | 35.569 | -150.41 | 221.55 |

Assumption test: Are the standard deviations of the groups equal?

Fig. 25B

```
                        SEQUENCE LISTING

<160> NUMBER OF SEQ ID NOS: 68

<210> SEQ ID NO 1
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 1
tcgtcgacgt tcggcgcgcg ccg                                            23

<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 2
tcgtcgtcgt tcggcgcgcg ccg                                            23

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3
tcgtcgttcg gcgcgccg                                                  18

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4
tcgtcgacga tcggcgcgcg ccg                                            23
```

<210> SEQ ID NO 5
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 5
ttcgtcgttt tgtcgtt                                              17

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 6
tttcgtcgtt tcgtcgtt                                             18

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 7
tcgtcgtttt gacgttttgt cgtt                                      24

<210> SEQ ID NO 8
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 8
tcgtcgtttt gtcgttttgt cgtt                                      24

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 9
tcgcgacgtt cggcgcgcgc cg                                        22

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 10
tcgtcgtttt gacgttttgt cgtt                                      24

<210> SEQ ID NO 11
<211> LENGTH: 20
<212> TYPE: DNA
<213> ORGANISM: Artificial sequence
<220> FEATURE:

```
<223> OTHER INFORMATION: Synthetic oligonucleotide

<400> SEQUENCE: 11
tccaggactt ctctcaggtt                                              20

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
cgtcgtcgtt cggcgcgcgc cg                                           22

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
gtcgtcgttc ggcgcgcgcc g                                            21

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tcgtcgttcg gcgcgcgccg                                              20

<210> SEQ ID NO 15
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 15
cgtcgtcgtt cggcgcgcgc cg                                           22

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 16
gtcgtcgttc ggcgcgcgcc g                                            21

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tcgtcgttcg gcgcgcgccg                                              20
```

```
<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
cgtcgttcgg cgcgcgccg                                                        19

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
gtcgttcggc gcgcgccg                                                         18

<210> SEQ ID NO 20
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 20
tcgttcggcg cgcgccg                                                          17

<210> SEQ ID NO 21
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 21
tcgtcgtcgt tcggcgcgcg cc                                                    22

<210> SEQ ID NO 22
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 22
tcgtcgtcgt tcggcgc                                                          17

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
tcgtcgtcgt tcggcgcgcg c                                                     21

<210> SEQ ID NO 24
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (5)..(5)
<223> OTHER INFORMATION: where n is any nucleotide
<220> FEATURE:
<221> NAME/KEY: misc_feature
<222> LOCATION: (8)..(8)
<223> OTHER INFORMATION: where n is any nucleotide
<220> FEATURE:
<221> NAME/KEY: misc_feature
<222> LOCATION: (9)..(10)
<223> OTHER INFORMATION: where n is any nucleotide and where any one or
      more n can be present or absent
<220> FEATURE:
<221> NAME/KEY: misc_feature
<222> LOCATION: (11)..(11)
<223> OTHER INFORMATION: where n is a pyrimidine
<220> FEATURE:
<221> NAME/KEY: misc_feature
<222> LOCATION: (13)..(13)
<223> OTHER INFORMATION: where n is any nucleotide

<400> SEQUENCE: 24
ttcgncgnnn ngncgtt                                                  17

<210> SEQ ID NO 25
<211> LENGTH: 17
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: where n is t or c

<400> SEQUENCE: 25
ttcgtcgttt ngtcgtt                                                  17

<210> SEQ ID NO 26
<211> LENGTH: 24
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: where n is any nucleotide
<220> FEATURE:
<221> NAME/KEY: misc_feature
<222> LOCATION: (7)..(7)
<223> OTHER INFORMATION: where n is any nucleotide
<220> FEATURE:
<221> NAME/KEY: misc_feature
<222> LOCATION: (8)..(10)
<223> OTHER INFORMATION: where n is any nucleotide and where any one or
      more n may be present or absent
<220> FEATURE:
<221> NAME/KEY: misc_feature
<222> LOCATION: (11)..(11)
<223> OTHER INFORMATION: where n is any nucleotide
<220> FEATURE:
<221> NAME/KEY: misc_feature
<222> LOCATION: (14)..(22)
<223> OTHER INFORMATION: where n is any nucleotide and where any one or
      more n may be present or absent

<400> SEQUENCE: 26
tcgncgnnnn ncgnnnnnnn nncg                                          24

<210> SEQ ID NO 27
<211> LENGTH: 24
<212> TYPE: DNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(10)
<223> OTHER INFORMATION: where n is any nucleotide and where any one or
      more n may be present or absent
<220> FEATURE:
<221> NAME/KEY: misc_feature
<222> LOCATION: (18)..(20)
<223> OTHER INFORMATION: where n is any nucleotide and where any one or
      more n may be present or absent

<400> SEQUENCE: 27
tcgtcgtnnn tcggcgcnnn gccg                                              24

<210> SEQ ID NO 28
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: where n is any nucleotide
<220> FEATURE:
<221> NAME/KEY: misc_feature
<222> LOCATION: (7)..(7)
<223> OTHER INFORMATION: where n is any nucleotide
<220> FEATURE:
<221> NAME/KEY: misc_feature
<222> LOCATION: (10)..(10)
<223> OTHER INFORMATION: where n is any nucleotide
<220> FEATURE:
<221> NAME/KEY: misc_feature
<222> LOCATION: (19)..(19)
<223> OTHER INFORMATION: where n is any nucleotide
<220> FEATURE:
<221> NAME/KEY: misc_feature
<222> LOCATION: (20)..(23)
<223> OTHER INFORMATION: where n is any nucleotide and where any one or
      more n may be present or absent

<400> SEQUENCE: 28
tcgncgncgn tcggcgcgnn nnn                                               23

<210> SEQ ID NO 29
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 29
tcgtcgtttt                                                              10

<210> SEQ ID NO 30
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (9)..(10)
<223> OTHER INFORMATION: where n is an abasic linker

<400> SEQUENCE: 30 tcgtcgttnn                                                              10
```

<210> SEQ ID NO 31
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 31
tcgacgtcga                                                          10

<210> SEQ ID NO 32
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 32
tcgtcgacga                                                          10

<210> SEQ ID NO 33
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 33
tcgcgacgtt                                                          10

<210> SEQ ID NO 34
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 34
tcgcgtcgtt                                                          10

<210> SEQ ID NO 35
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 35
caatatttat tg                                                       12

<210> SEQ ID NO 36
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 36
ccgttttgtg g                                                        11

<210> SEQ ID NO 37
<211> LENGTH: 13
<212> TYPE: DNA
<213> ORGANISM: Artificial sequence
<220> FEATURE:
<223> OTHER INFORMATION: Synthetic oligonucleotide

```
<400> SEQUENCE: 37
cggcgccgtg ccg                                                        13

<210> SEQ ID NO 38
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 38
cggcgccgtt gccg                                                       14

<210> SEQ ID NO 39
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(7)
<223> OTHER INFORMATION: where n is an abasic linker

<400> SEQUENCE: 39
cggcgnncgc cg                                                         12

<210> SEQ ID NO 40
<211> LENGTH: 13
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(8)
<223> OTHER INFORMATION: where n is an abasic linker

<400> SEQUENCE: 40
cggcgnnntg ccg                                                        13

<210> SEQ ID NO 41
<211> LENGTH: 14
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (7)..(8)
<223> OTHER INFORMATION: where n is an abasic linker

<400> SEQUENCE: 41
cggcggnncc gccg                                                       14

<210> SEQ ID NO 42
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 42
cggcgtcgcc gccg                                                       14

<210> SEQ ID NO 43
```

```
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 43
cgtcgacggg acggg                                                       15

<210> SEQ ID NO 44
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 44
cgtcgacgtg acggg                                                       15

<210> SEQ ID NO 45
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 45
gagagttggg ctctc                                                       15

<210> SEQ ID NO 46
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 46
gtcgaggagg t                                                           11

<210> SEQ ID NO 47
<211> LENGTH: 12
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(7)
<223> OTHER INFORMATION: where n is an abasic linker

<400> SEQUENCE: 47
taatanntat ta                                                          12

<210> SEQ ID NO 48
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 48
taatatccat ta                                                          12

<210> SEQ ID NO 49
<211> LENGTH: 12
<212> TYPE: DNA
<213> ORGANISM: Artificial sequence
```

```
<220> FEATURE:
<223> OTHER INFORMATION: Synthetic oligonucleotide

<400> SEQUENCE: 49
taatatttat ta                                                          12

<210> SEQ ID NO 50
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 50
ggcgcgctgc cg                                                          12

<210> SEQ ID NO 51
<211> LENGTH: 36
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: where n is a purine
<220> FEATURE:
<221> NAME/KEY: misc_feature
<222> LOCATION: (2)..(2)
<223> OTHER INFORMATION: where n is not c
<220> FEATURE:
<221> NAME/KEY: misc_feature
<222> LOCATION: (5)..(6)
<223> OTHER INFORMATION: where n is a pyrimidine
<220> FEATURE:
<221> NAME/KEY: misc_feature
<222> LOCATION: (6)..(31)
<223> OTHER INFORMATION: where one internucleotide linkage is a 3' to 3'
      linkage
<220> FEATURE:
<221> NAME/KEY: misc_feature
<222> LOCATION: (7)..(18)
<223> OTHER INFORMATION: where n is any nucleotide and where any one or
      more n may be present or absent
<220> FEATURE:
<221> NAME/KEY: misc_feature
<222> LOCATION: (18)..(30)
<223> OTHER INFORMATION: where n is any nucleotide and where any one or
      more n may be present or absent
<220> FEATURE:
<221> NAME/KEY: misc_feature
<222> LOCATION: (31)..(32)
<223> OTHER INFORMATION: where n is a pyrimidine
<220> FEATURE:
<221> NAME/KEY: misc_feature
<222> LOCATION: (35)..(35)
<223> OTHER INFORMATION: where n is not c
<220> FEATURE:
<221> NAME/KEY: misc_feature
<222> LOCATION: (36)..(36)
<223> OTHER INFORMATION: where n is a purine

<400> SEQUENCE: 51
nncgnnnnnn nnnnnnnnnn nnnnnnnnnn nngcnn                                36

<210> SEQ ID NO 52
<211> LENGTH: 48
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
```

```
<222> LOCATION: (4)..(6)
<223> OTHER INFORMATION: where 3 nucleotides may be present or absent
<220> FEATURE:
<221> NAME/KEY: misc_feature
<222> LOCATION: (7)..(9)
<223> OTHER INFORMATION: where 3 nucleotides may be present or absent
<220> FEATURE:
<221> NAME/KEY: misc_feature
<222> LOCATION: (10)..(12)
<223> OTHER INFORMATION: where feature may be present or absent
<220> FEATURE:
<221> NAME/KEY: misc_feature
<222> LOCATION: (12)..(37)
<223> OTHER INFORMATION: where one internucleotide linkage is a 3' to 3'
      linkage
<220> FEATURE:
<221> NAME/KEY: misc_feature
<222> LOCATION: (13)..(24)
<223> OTHER INFORMATION: where n is any nucleotide and where any one or
      more n may be present or absent
<220> FEATURE:
<221> NAME/KEY: misc_feature
<222> LOCATION: (25)..(36)
<223> OTHER INFORMATION: where n is any nucleotide and where any one or
      more n may be present or absent
<220> FEATURE:
<221> NAME/KEY: misc_feature
<222> LOCATION: (40)..(42)
<223> OTHER INFORMATION: where 3 nucleotides may be present or absent
<220> FEATURE:
<221> NAME/KEY: misc_feature
<222> LOCATION: (43)..(45)
<223> OTHER INFORMATION: where 3 nucleotides may be present or absent
<220> FEATURE:
<221> NAME/KEY: misc_feature
<222> LOCATION: (46)..(48)
<223> OTHER INFORMATION: where 3 nucleotides may be present or absent

<400> SEQUENCE: 52
tcgtcgtcgt cgnnnnnnnn nnnnnnnnnn nnnnnngctg ctgctgct                    48

<210> SEQ ID NO 53
<211> LENGTH: 11
<212> TYPE: DNA
<213> ORGANISM: Artificial sequence
<220> FEATURE:
<223> OTHER INFORMATION: Synthetic oligonucleotide

<400> SEQUENCE: 53
tcgtcgtttt a                                                            11

<210> SEQ ID NO 54
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 54
cggcgccgtg ccg                                                          13

<210> SEQ ID NO 55
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 55
cggcgtcgtg ccg                                                          13
```

<210> SEQ ID NO 56
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 56
tcgtcgtttt acggcgccgt gccg                              24

<210> SEQ ID NO 57
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 57
tcgtcgtttt acggcgtcgt gccg                              24

<210> SEQ ID NO 58
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 58
cggcgcgcgc cg                                           12

<210> SEQ ID NO 59
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 59
cggcggccgc cg                                           12

<210> SEQ ID NO 60
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 60
cgacgatcgt cg                                           12

<210> SEQ ID NO 61
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 61
cgacgtacgt cg                                           12

<210> SEQ ID NO 62
<211> LENGTH: 12
<212> TYPE: DNA
<213> ORGANISM: Artificial sequence
<220> FEATURE:
<223> OTHER INFORMATION: Synthetic oligonucleotide

```
<400> SEQUENCE: 62
cgcgcgcgcg cg                                                          12

<210> SEQ ID NO 63
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 63
gcgcgcgcgc gc                                                          12

<210> SEQ ID NO 64
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 64
ccccccgggg gg                                                          12

<210> SEQ ID NO 65
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 65
ggggggcccc cc                                                          12

<210> SEQ ID NO 66
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 66
cccccggggg                                                             10

<210> SEQ ID NO 67
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 67
gggggccccc                                                             10

<210> SEQ ID NO 68
<211> LENGTH: 10
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: where n is inosine
<220> FEATURE:
```

```
<221> NAME/KEY: misc_feature
<222> LOCATION: (6)..(6)
<223> OTHER INFORMATION: where n is inosine

<400> SEQUENCE: 68 tcntcntttt                                                          10
```

SEMI-SOFT C-CLASS IMMUNOSTIMULATORY OLIGONUCLEOTIDES

RELATED APPLICATION

This application is a divisional of U.S. Application Ser. No. 11/255,100, filed Oct. 20, 2005, which claims priority to U.S. Provisional Application having Ser. No. 60/620,759 entitled "SEMI-SOFT C-CLASS IMMUNOSTIMULATORY OLIGONUCLEOTIDES" filed Oct. 20, 2004, the entire contents of which are incorporated by reference herein.

FIELD OF THE INVENTION

The present invention relates generally to immunostimulatory oligonucleotides with reduced renal inflammatory effects, compositions thereof and methods of using the immunostimulatory oligonucleotides. In particular the immunostimulatory oligonucleotides are C-class semi-soft oligonucleotides that are particularly effective in the treatment of allergy and asthma, cancer and infectious disease.

BACKGROUND OF THE INVENTION

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P., et al., 1991, *J Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci. USA 96:9305-10).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci. USA 96:9305-10; Liang, 1996 J. Clin. Invest. 98:1119-1129).

Several different classes of CpG oligonucleotides has recently been described. One class is potent for activating B cells but is relatively weak in inducing IFN-α and NK cell activation; this class has been termed the B class. The B class CpG oligonucleotides typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class of CpG oligonucleotides activates B cells and NK cells and induces IFN-α; this class has been termed the C-class. The C-class CpG oligonucleotides, as first characterized, typically are fully stabilized, include a B class-type sequence and a GC-rich palindrome or near-palindrome. This class has been described in co-pending U.S. patent application US10/224,523 filed on Aug. 19, 2002 and related PCT Patent Application PCT/US02/26468 published under International Publication Number WO 03/015711.

SUMMARY OF THE INVENTION

It has been discovered that immunostimulatory properties of specific C-class CpG oligonucleotides with the selective inclusion of one or more non-stabilized linkages between certain nucleotides have significant activity and are particularly useful in the treatment of allergy and asthma. The non-stabilized linkages are preferably natural linkages, i.e., phosphodiester linkages or phosphodiester-like linkages. A non-stabilized linkage will typically, but not necessarily, be relatively susceptible to nuclease digestion. The immunostimulatory oligonucleotides of the instant invention include at least one non-stabilized linkage situated between a 5° C. and an adjacent 3' G, wherein both the 5° C. and the 3' G are internal nucleotides.

The immunostimulatory oligonucleotides of the instant invention are useful for inducing a Th1-like immune response. Accordingly, the immunostimulatory oligonucleotides of the instant invention are useful as adjuvants for vaccination, and they are useful for treating diseases including cancer, infectious disease, allergy, and asthma. They are believed to be of particular use in any condition calling for prolonged or repeated administration of immunostimulatory oligonucleotide for any purpose, but are particularly useful in the treatment of asthma and allergic diseases such as allergic rhinitis.

The present invention relates in part to immunostimulatory CpG containing oligonucleotides. In one aspect the invention is an oligonucleotide having the formula: 5' TC_GX$_1$C_G X$_2$N$_1$ X$_3$C_GN$_2$CG 3' (SEQ ID NO: 26). The oligonucleotide includes at least 2 stabilized internucleotide linkages. "_" represents phosphodiester or phosphodiester-like internucleotide linkage. N$_1$ is 0-3 nucleotides in length, N$_2$ is 0-9 nucleotides in length with N referring to any nucleotide. X$_1$, X$_2$, and X$_3$ are any nucleotide. In some embodiments X$_1$, X$_2$, and X$_3$ are T.

In some embodiments the oligonucleotide may comprise 5' T*C_GTC_GTN$_1$TC_GGCGCN$_1$GCCG 3' (SEQ ID NO: 27). In one embodiment the oligonucleotide may comprise 5' T*C_G*T*C_G*T*N$_1$*T*C_G*G*C*G*CN$_1$G*C*C*G 3' (SEQ ID NO: 27). In some embodiments N$_1$ is 3 or 2 nucleotides in length. In other embodiments N$_1$ is 0 nucleotides in length.

The immunostimulatory oligonucleotide may comprise 5' T*C_G*T*C_G*T*C_G*T*T*C_G*G*C*G*C_G*C*G* C*C*G 3' (SEQ ID NO: 2), wherein * represents a stabilized internucleotide linkage. Optionally, when specifically stated, 5' may refer to the free 5' end of the oligonucleotide and 3' may refer to the free 3' end of the oligonucleotide.

In other embodiments the immunostimulatory oligonucleotide may comprise 5' T*C_G*T*C_G*T*T*C_G*G*C*G*C*G*C*C*G 3' (SEQ ID NO: 3), wherein * represents a stabilized internucleotide linkage. Optionally, when specifically stated, 5' may refer to the free 5' end of the oligonucleotide and 3' may refer to the free 3' end of the oligonucleotide.

In another aspect, the immunostimulatory oligonucleotide has the following formula TC_G X$_1$C_G X$_2$C_G X$_3$TC_GGCGC_G N$_3$3' (SEQ ID NO: 28).

N$_3$ is 1-5 nucleotides in length with N referring to any nucleotide. In one embodiment N$_3$ is 5 nucleotides. X$_1$, X$_2$, and X$_3$ are any nucleotide. In some embodiments X$_1$ and X$_3$ are T.

In one embodiment the oligonucleotide may comprise 5' TC_GTC_GAC_GATC_GGCGC_GCGCCG3' (SEQ ID NO: 4), wherein the oligonucleotide includes at least 2 stabilized internucleotide linkages and _ represents phosphodiester or phosphodiester-like internucleotide linkage. In one embodiment the oligonucleotide may comprise 5' T*C_G*T*C_G*A*C_G*A*T*C_G*G*C*G*C_G*C*G*C*C*G 3' (SEQ ID NO: 4). Optionally, when specifically stated, 5' may refer to the free 5' end of the oligonucleotide and 3' may refer to the free 3' end of the oligonucleotide.

According to another aspect of the invention an immunostimulatory oligonucleotide having the following formula: 5' TTC_GX$_2$C_GN$_1$X$_1$_GX$_3$C_GTT 3' (SEQ ID NO: 24) is provided. The oligonucleotide includes at least 2 stabilized internucleotide linkages and _ represents phosphodiester or phosphodiester-like internucleotide linkage. N$_1$ is 1-3 nucleotides in length with N referring to any nucleotide. X$_1$ is a pyrimidine. X$_2$ and X$_3$ are any nucleotide. In some embodiments X$_2$ and X$_3$ are T.

In one embodiment the oligonucleotide may comprise 5' TTC_GTC_GTTTX$_1$_GTC_GTT 3' (SEQ ID NO: 25). In another embodiment the oligonucleotide may comprise 5' T*T*C_G*T*C_G*T*T*T*X$_1$_G*T*C_G*T*T 3' (SEQ ID NO: 25). In some embodiments X$_1$ is T or C.

The oligonucleotide may comprise 5' T*T*C_G*T*C_G*T*T*T*T_G*T*C_G*T*T 3' (SEQ ID NO: 5), wherein * represents a stabilized internucleotide linkage. Optionally, when specifically stated, 5' may refer to the free 5' end of the oligonucleotide and 3' may refer to the free 3' end of the oligonucleotide.

The oligonucleotide may comprise 5' T*T*T*C_G*T*C_G*T*T*T*C_G*T*C_G*T*T 3' (SEQ ID NO: 6), wherein * represents a stabilized internucleotide linkage. Optionally, when specifically stated, 5' may refer to the free 5' end of the oligonucleotide and 3' may refer to the free 3' end of the oligonucleotide.

In some aspects of the invention the oligonucleotide has one of the following formulas TCGTCGTTCGGCGCGCCG (SEQ ID NO: 3), TCGTCGTCGTTCGGCGCGCGCCG (SEQ ID NO: 2), TCGTCGACGATCGGCGCGCGCCG (SEQ ID NO: 4), TTCGTCGTTTTGTCGTT. (SEQ ID NO: 5), or TTTCGTCGTTTCGTCGTT. (SEQ ID NO: 6)

In other aspects of the invention the oligonucleotide has one of the following formulas TCGTCGTC, CGTCGTCG, GTCGTCGT, TCGTCGTT, CGTCGTTC, GTCGTTCG, TCGTTCGG, CGTTCGGC, GTTCGGCG, TTCGGCGC, TCGGCGCG, CGGCGCGC, GGCGCGCG, GCGCGCGC, CGCGCGCC, or GCGCGCCG.

In other aspects of the invention the oligonucleotide has one of the following formulas T*C_G*T*C_G*T*C, C_G*T*C_G*T*C_G, G*T*C_G*T*C_G*T, T*C_G*T*C_G*T*T, C_G*T*C_G*T*T*C, G*T*C_G*T*T*C_G, T*C_G*T*T*C_G*G, C_G*T*T*C_G*G*C, T*T*C_G*G*C*G*C, G*T*T*C_G*G*C*G, T*C_G*G*C*G*C_G, C_G*G*C*G*C_G*C, G*G*C*G*C_G*C*G, G*C*G*C_G*C*G*C, C*G*C_G*C*G*C*C, or G*C_G*C*G*C*C*G.

In other aspects of the invention an oligonucleotide comprising: T*C_G*T*C_G*T*C, wherein * represents a stabilized internucleotide linkage and _ represents phosphodiester or phosphodiester-like internucleotide linkage is provided. Optionally the oligonucleotide may be 5' T*C-G*T*C-G*T*C-G*T*T*C-G*G*C*G*C-G*C*G*C*C 3' (SEQ ID NO.: 21), 5' T*C-G*T*C-G*T*C-G*T*T*C-G*G*C*G*C 3' (SEQ ID NO.: 22), or 5' T*C-G*T*C-G*T*C-G*T*T*C-G*G*C*G*C-G*C*G*C 3' (SEQ ID NO.: 23), wherein 5' refers to the free 5' end of the oligonucleotide and 3' refers to the free 3' end of the oligonucleotide.

In other aspects an oligonucleotide comprising: T*C_G*T*T*C_G*G, wherein * represents a stabilized internucleotide linkage and _ represents phosphodiester or phosphodiester-like internucleotide linkage is provided. Optionally the oligonucleotide may be 5' C-G*T*C-G*T*C-G*T*T*C-G*G*C*G*C-G*C*G*C*C*G 3' (SEQ ID NO.: 15), 5' G*T*C-G*T*C-G*T*T*C-G*G*C*G*C-G*C*G*C*C*G 3' (SEQ ID NO.: 16), 5' T*C-G*T*C-G*T*T*C-G*G*C*G*C-G*C*G*C*C*G 3' (SEQ ID NO.: 17), 5' C-G*T*C-G*T*T*C-G*G*C*G*C-G*C*G*C*C*G 3' (SEQ ID NO.: 18), 5' G*T*C-G*T*T*C-G*G*C*G*C-G*C*G*C*C*G 3' (SEQ ID NO.: 19), or 5' T*C-G*T*T*C-G*G*C*G*C-G*C*G*C*C*G 3' (SEQ ID NO.: 20), wherein 5' refers to the free 5' end of the oligonucleotide and 3' refers to the free 3' end of the oligonucleotide.

A pharmaceutical composition comprising an oligonucleotide of the invention and a pharmaceutically acceptable carrier is provided.

In some embodiments the composition is formulated in a nebulizer or an inhaler. The inhaler may be a metered dose inhaler. Alternatively the inhaler is a powder inhaler.

In other embodiments the pharmaceutical composition may include a chemotherapeutic agent. In yet other embodiments the composition may include an anti-viral agent.

The pharmaceutical composition may optionally include a pharmaceutically acceptable carrier formulated for subcutaneous administration, oral administration or intranasal administration.

In one embodiment the oligonucleotide is in a pharmaceutical composition optionally comprising a pharmaceutically acceptable carrier. In some embodiments the oligonucleotide is formulated as an aerosol.

In one embodiment the oligonucleotide further comprises an adjuvant or a cytokine.

In one embodiment the oligonucleotide further comprises an antigen, wherein the oligonucleotide is a vaccine adjuvant.

In one embodiment the antigen is selected from the group consisting of: a viral antigen, a bacterial antigen, a fungal antigen, a parasitic antigen, and a tumor antigen. In one embodiment the antigen is encoded by a nucleic acid vector. In one embodiment the antigen is a peptide antigen. In one embodiment the antigen is covalently linked to the oligonucleotide or immunostimulatory nucleic acid molecule. In another embodiment the antigen is not covalently linked to the oligonucleotide or immunostimulatory nucleic acid molecule.

In one embodiment the phosphodiester or phosphodiester-like linkage is phosphodiester. In one embodiment the phosphodiester-like linkage is boranophosphonate or diastereomerically pure Rp phosphorothioate.

In one embodiment the stabilized backbone comprises a plurality of internucleotide linkages selected from the group consisting of: phosphorothioate, phosphorodithioate, methylphosphonate, methylphosphorothioate, and any combination thereof. In one embodiment the stabilized backbone comprises a plurality of phosphorothioate internucleotide linkages.

In one embodiment the immunostimulatory nucleic acid molecule is 4-100 nucleotides long.

In other aspects the invention is a method for treating asthma by administering to a subject having or at risk of having asthma an oligonucleotide of the invention in an effective amount to treat asthma.

In yet other aspects the invention is a method for treating allergy by administering to a subject having or at risk of having allergy an oligonucleotide of the invention in an effective amount to treat allergy. In one embodiment the subject has allergic rhinitis. In one embodiment the oligonucleotide is administered to a mucosal surface. In other embodiments the oligonucleotide is administered in an aerosol formulation. Optionally the oligonucleotide is administered intranasally.

A method for inducing cytokine production is provided according to another aspect of the invention. The method is performed by administering to a subject an immunostimulatory CpG oligonucleotide described herein in an effective amount to induce a cytokine selected from the group consisting of IL-6, IL-8, IL-12, IL-18, TNF, IFN-α, chemokines, and IFN-γ.

In another aspect the invention is a composition of the CpG immunostimulatory oligonucleotides described herein in combination with an antigen or other therapeutic compound, such as an anti-microbial agent. The anti-microbial agent may be, for instance, an anti-viral agent, an anti-parasitic agent, an anti-bacterial agent or an anti-fungal agent.

A composition of a sustained release device including the CpG immunostimulatory oligonucleotides described herein is provided according to another aspect of the invention.

The composition may optionally include a pharmaceutical carrier and/or be formulated in a delivery device. In some embodiments the delivery device is selected from the group consisting of cationic lipids, cell permeating proteins, and sustained release devices. In one embodiment the sustained release device is a biodegradable polymer or a microparticle.

According to another aspect of the invention a method of stimulating an immune response is provided. The method involves administering a CpG immunostimulatory oligonucleotide to a subject in an amount effective to induce an immune response in the subject. Preferably the CpG immunostimulatory oligonucleotide is administered orally, locally, in a sustained release device, mucosally, systemically, parenterally, or intramuscularly. When the CpG immunostimulatory oligonucleotide is administered to the mucosal surface it may be delivered in an amount effective for inducing a mucosal immune response or a systemic immune response. In preferred embodiments the mucosal surface is selected from the group consisting of an oral, nasal, rectal, vaginal, and ocular surface.

In some embodiments the method includes exposing the subject to an antigen wherein the immune response is an antigen-specific immune response. In some embodiments the antigen is selected from the group consisting of a tumor antigen, a viral antigen, a bacterial antigen, a parasitic antigen and a peptide antigen.

CpG immunostimulatory oligonucleotides are capable of provoking a broad spectrum of immune response. For instance these CpG immunostimulatory oligonucleotides can be used to redirect a Th2 to a Th1 immune response. CpG immunostimulatory oligonucleotides may also be used to activate an immune cell, such as a lymphocyte (e.g., B and T cells), a dendritic cell, and an NK cell. The activation can be performed in vivo, in vitro, or ex vivo, i.e., by isolating an immune cell from the subject, contacting the immune cell with an effective amount to activate the immune cell of the CpG immunostimulatory oligonucleotide and re-administering the activated immune cell to the subject. In some embodiments the dendritic cell presents a cancer antigen. The dendritic cell can be exposed to the cancer antigen ex vivo.

The immune response produced by CpG immunostimulatory oligonucleotides may also result in induction of cytokine production, e.g., production of IL-6, IL-8, IL-12, IL-18, TNF, IFN-α, chemokines, and IFN-γ.

In still another embodiment, the CpG immunostimulatory oligonucleotides are useful for treating cancer. The CpG immunostimulatory oligonucleotides are also useful according to other aspects of the invention in preventing cancer (e.g., reducing a risk of developing cancer) in a subject at risk of developing a cancer. The cancer may be selected from the group consisting of biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreatic cancer, prostate cancer, rectal cancer, sarcomas, thyroid cancer, and renal cancer, as well as other carcinomas and sarcomas. In some important embodiments, the cancer is selected from the group consisting of bone cancer, brain and CNS cancer, connective tissue cancer, esophageal cancer, eye cancer, Hodgkin's lymphoma, larynx cancer, oral cavity cancer, skin cancer, and testicular cancer.

CpG immunostimulatory oligonucleotides may also be used for increasing the responsiveness of a cancer cell to a cancer therapy (e.g., an anti-cancer therapy), optionally when the CpG immunostimulatory oligonucleotide is administered in conjunction with an anti-cancer therapy. The anti-cancer therapy may be a chemotherapy, a vaccine (e.g., an in vitro primed dendritic cell vaccine or a cancer antigen vaccine) or an antibody based therapy. This latter therapy may also involve administering an antibody specific for a cell surface antigen of, for example, a cancer cell, wherein the immune response results in antibody dependent cellular cytotoxicity (ADCC). In one embodiment, the antibody may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-111, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Thus, according to some aspects of the invention, a subject having cancer or at risk of having a cancer is administered a CpG immunostimulatory oligonucleotide and an anti-cancer therapy. In some embodiments, the anti-cancer therapy is selected from the group consisting of a chemotherapeutic agent, an immunotherapeutic agent and a cancer vaccine. In some embodiments the cancer medicament is taxol or a combination of carboplatin and paclitaxel.

In still another embodiment of the methods directed to preventing or treating cancer, the subject may be further administered interferon-α.

The invention in other aspects relates to methods for preventing disease in a subject. The method involves administering to the subject a CpG immunostimulatory oligonucleotide on a regular basis to promote immune system responsiveness to prevent disease in the subject. Examples of diseases or conditions sought to be prevented using the prophylactic methods of the invention include microbial infections (e.g., sexually transmitted diseases) and anaphylactic shock from food allergies.

In other aspects, the invention is a method for inducing an innate immune response by administering to the subject a CpG immunostimulatory oligonucleotide in an amount effective for activating an innate immune response.

According to another aspect of the invention a method for treating or preventing a viral or retroviral infection is provided. The method involves administering to a subject having or at risk of having a viral or retroviral infection, an effective amount for treating or preventing the viral or retroviral infection of any of the compositions of the invention.

In some embodiments the virus is caused by a hepatitis virus e.g., hepatitis B, hepatitis C, HIV, herpes virus, or papillomavirus.

A method for treating or preventing a bacterial infection is provided according to another aspect of the invention. The method involves administering to a subject having or at risk of having a bacterial infection, an effective amount for treating or preventing the bacterial infection of any of the compositions of the invention. In one embodiment the bacterial infection is due to an intracellular bacteria.

In another aspect the invention is a method for treating or preventing a parasite infection by administering to a subject having or at risk of having a parasite infection, an effective amount for treating or preventing the parasite infection of any of the compositions of the invention. In one embodiment the parasite infection is due to an intracellular parasite. In another embodiment the parasite infection is due to a non-helminthic parasite.

In some embodiments the subject is a human and in other embodiments the subject is a non-human vertebrate selected from the group consisting of a dog, cat, horse, cow, pig, turkey, goat, fish, monkey, chicken, rat, mouse, and sheep, In another aspect the invention relates to a method for inducing a TH1 immune response by administering to a subject any of the compositions of the invention in an effective amount to produce a TH1 immune response.

In another aspect, the invention relates to a method for treating autoimmune disease by administering to a subject having or at risk of having an autoimmune disease an effective amount for treating or preventing the autoimmune disease of any of the compositions of the invention.

In other embodiments the oligonucleotide is delivered to the subject in an effective amount to induce cytokine expression. Optionally the cytokine is selected from the group consisting of IL-6, TNFα, IFNα, IFNγ and IP-10. In other embodiments the oligonucleotide is delivered to the subject in an effective amount to shift the immune response to a Th1 biased response form a Th2 biased response.

The invention in some aspects is a method for treating airway remodeling, comprising: administering to a subject an oligonucleotide comprising a CG dinucleotide, in an effective amount to treat airway remodeling in the subject. In one embodiment the subject has asthma, chronic obstructive pulmonary disease, or is a smoker. In other embodiments the subject is free of symptoms of asthma.

Use of an oligonucleotide of the invention for stimulating an immune response is also provided as an aspect of the invention.

Use of an oligonucleotide of the invention in the manufacture of a medicament of for stimulating an immune response and performing any of the methods of the invention is also provided.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIGS. 22A and 22B depict histamine release as a function of increased airway resistance (22A) or decrease in lung compliance (22B). FIGS. 22C and 22D are bar graphs depicting the increase in airway resistance (22C) or decrease in lung compliance (22D) in response to treatment with saline, OVA or SEQ ID NO 7 at the indicated dosages.

FIG. 23 is a Summary of Statistical Analysis used herein (FIG. 22) for airway resistance (23A) and lung compliance (23B).

FIGS. 24A and 24B depict histamine release as a function of increased airway resistance (24A) or decrease in lung compliance (24B). FIGS. 24C and 24D are bar graphs depicting the increase in airway resistance (24C) or decrease in lung compliance (24D) in response to treatment with saline, OVA or SEQ ID NO 2 at the indicated dosages.

FIG. 25 is a Summary of Statistical Analysis used herein (FIG. 24) for airway resistance (25A) and lung compliance (25B)

FIG. 26 is a summary of the graphs in FIGS. 22 and 24.

DETAILED DESCRIPTION

Figure 1:
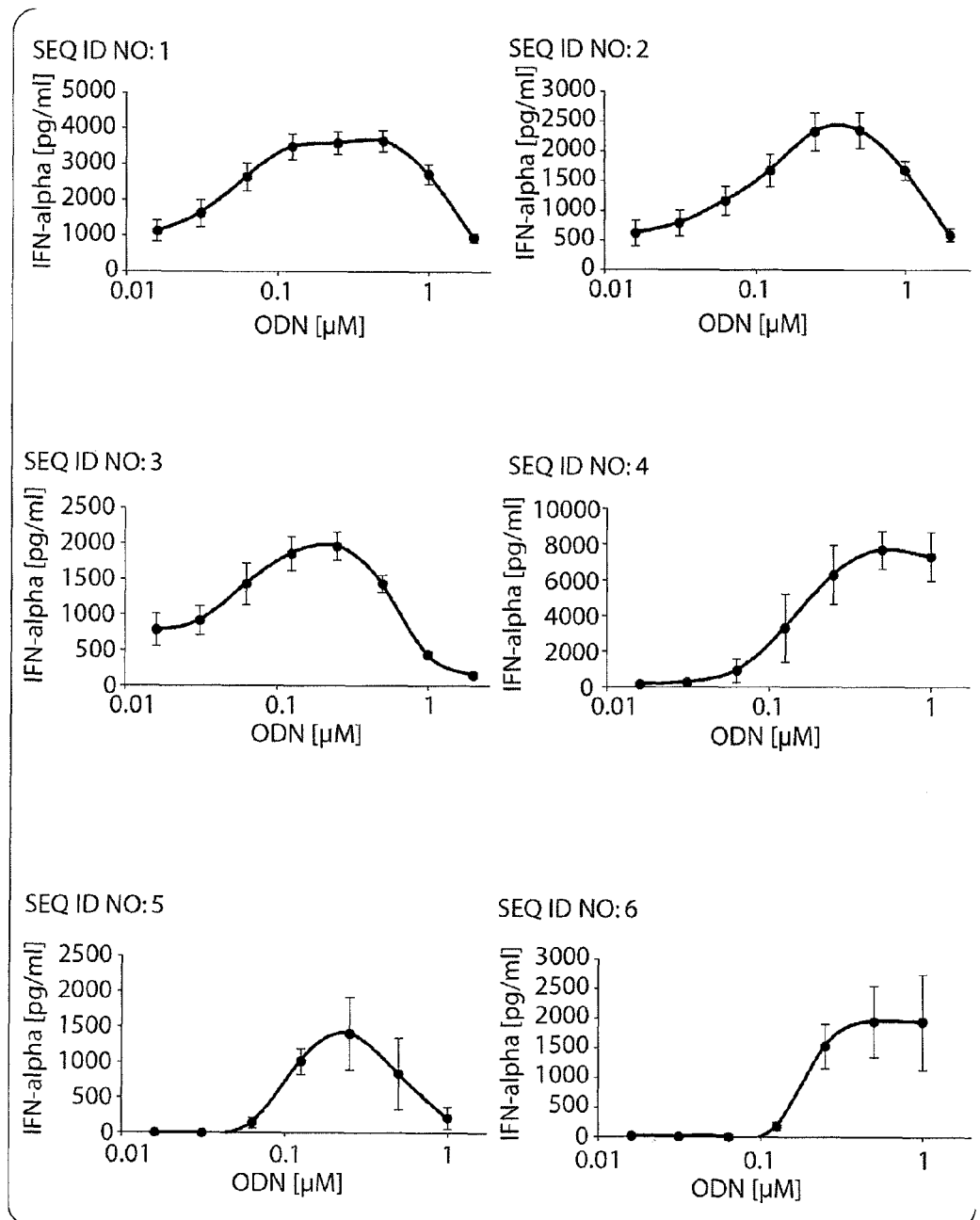
FIG. 1 is a series of graphs depicting IFN-alpha induction by human PBMC treated with CpG ODN.

A sub-set of C-class semi-soft immunostimulatory oligonucleotides are provided according to the invention. The immunostimulatory oligonucleotides of the invention described herein, in some embodiments have improved properties including similar or enhanced potency, reduced systemic exposure to the kidney, liver and spleen, and may have reduced reactogenicity at injection sites. Although applicant is not bound by a mechanism, it is believed that these improved properties are associated with the strategic placement within the immunostimulatory oligonucleotides of phosphodiester or phosphodiester-like "internucleotide linkages". The term "internucleotide linkage" as used herein refers to the covalent backbone linkage joining two adjacent nucleotides in a nucleic acid molecule. The covalent backbone linkage will typically be a modified or unmodified phosphate linkage, but other modifications are possible. Thus a linear oligonucleotide that is n nucleotides long has a total of n−1 internucleotide linkages. These covalent backbone linkages can be modified or unmodified in the immunostimulatory oligonucleotides according to the teachings of the invention.

In particular, phosphodiester or phosphodiester-like internucleotide linkages involve "internal dinucleotides". An internal dinucleotide in general shall mean any pair of adjacent nucleotides connected by an internucleotide linkage, in which neither nucleotide in the pair of nucleotides is a terminal nucleotide, i.e., neither nucleotide in the pair of nucleotides is a nucleotide defining the 5' or 3' end of the oligonucleotide. Thus a linear oligonucleotide that is n nucleotides long has a total of n−1 dinucleotides and only n−3 internal dinucleotides. Each internucleotide linkage in an internal dinucleotide is an internal internucleotide linkage. Thus a linear oligonucleotide that is n nucleotides long has a total of n−1 internucleotide linkages and only n−3 internal internucleotide linkages. The strategically placed phosphodiester or phosphodiester-like internucleotide linkages, therefore, refer to phosphodiester or phosphodiester-like internucleotide linkages positioned between any pair of nucleotides in the nucleic acid sequence. In some embodiments the phosphodiester or phosphodiester-like internucleotide linkages are not positioned between either pair of nucleotides closest to the 5' or 3' end.

The invention is based at least in some aspects on the surprising discovery that the specific C-class semi-soft oligonucleotides described herein have important immunostimulatory activity and are preferably useful in the treatment of allergy and asthma. These molecules have at least the same or in many cases possess greater immunostimulatory activity, in many instances, than corresponding fully stabilized immunostimulatory oligonucleotides having the same nucleotide sequence.

A semi-soft oligonucleotide is an immunostimulatory oligonucleotide having a partially stabilized backbone, in which phosphodiester or phosphodiester-like internucleotide linkages occur only within at least one internal pyrimidine-purine (YZ, preferably CG) dinucleotide. Semi-soft oligonucleotides generally possess increased immunostimulatory potency relative to corresponding fully stabilized immunostimulatory oligonucleotides. Due to the greater potency of semi-soft oligonucleotides, semi-soft oligonucleotides may be used at lower effective concentrations and have lower effective doses than conventional fully stabilized immunostimulatory oligonucleotides in order to achieve a desired biological effect.

Whereas fully stabilized immunostimulatory oligonucleotides can exhibit dose-response maxima, semi-soft oligonucleotides of the instant invention appear to have monotonically increasing dose-response curves (as assayed by TLR9 stimulation) extending into higher concentrations beyond the optimal concentration for corresponding fully stabilized immunostimulatory oligonucleotides. Thus it is believed that semi-soft oligonucleotides of the instant invention may induce greater immunostimulation than fully stabilized immunostimulatory oligonucleotides.

Whereas fully stabilized immunostimulatory oligonucleotides less than 20 nucleotides long can have modest immunostimulatory activity compared with longer (e.g., 24 nucleotides long) fully stabilized oligonucleotides, semi-soft oligonucleotides as short as 16 nucleotides long have been discovered to have immunostimulatory activity at least equal to immunostimulatory activity of fully stabilized oligonucleotides over 20 nucleotides long.

In some instances where a 6-mer phosphorothioate oligonucleotide appeared to lack immunostimulatory activity, substitution of even one phosphodiester internal CG internucleotide linkage for a phosphorothioate linkage was found to yield a corresponding 6-mer with immunostimulatory activity.

Thus the size (i.e., the number of nucleotide residues along the length of the oligonucleotide) of the immunostimulatory oligonucleotide may also contribute to the stimulatory activity of the oligonucleotide. For facilitating uptake into cells immunostimulatory oligonucleotides may have a minimum length of 6 nucleotide residues. Oligonucleotides of any size greater than 6 nucleotides (even many kb long) are capable of inducing an immune response according to the invention if sufficient immunostimulatory motifs are present, since larger nucleic acids are degraded inside of cells. It is believed by the instant inventors that semi-soft oligonucleotides as short as 4 nucleotides can also be immunostimulatory if they can be delivered to the interior of the cell. In certain preferred embodiments according to the instant invention, the immunostimulatory oligonucleotides are between 4 and 100 nucleotides long. In typical embodiments the immunostimulatory oligonucleotides are between 6 and 40 or 10 and 40 nucleotides long. In certain preferred embodiments according to the instant invention, the immunostimulatory oligonucleotides are between 6 and 19 or 6 and 24 nucleotides long.

It is also believed that the foregoing properties of semi-soft oligonucleotides generally increase with increasing "dose" of phosphodiester or phosphodiester-like internucleotide linkages involving internal CG dinucleotides. Thus it is believed, for example, that generally for a given oligonucleotide sequence with five internal CG dinucleotides, an oligonucleotide with five internal phosphodiester or phosphodiester-like CG internucleotide linkages is more immunostimulatory than an oligonucleotide with four internal phosphodiester or phosphodiester-like CG internucleotide linkages, which in turn is more immunostimulatory than an oligonucleotide with three internal phosphodiester or phosphodiester-like CG internucleotide linkages, which in turn is more immunostimulatory than an oligonucleotide with two internal phosphodiester or phosphodiester-like CG internucleotide linkages, which in turn is more immunostimulatory than an oligonucleotide with one internal phosphodiester or phosphodiester-like CG internucleotide linkage. Importantly, inclusion of even one internal phosphodiester or phosphodiester-like CG internucleotide linkage is believed to be advantageous over no internal phosphodiester or phosphodiester-like CG internucleotide linkage. In addition to the number of phosphodiester or phosphodiester-like internucleotide linkages, the position along the length of the oligonucleotide can also affect potency.

The immunostimulatory oligonucleotides of the present invention are generally protected from rapid degradation in the serum. The immunostimulatory oligonucleotides of the present invention are also generally protected from rapid degradation in most tissues, with the exception of particular tissues with specific or excessive nuclease activity that are capable of degrading the immunostimulatory oligonucleotides. This results in the reduction of immunostimulatory oligonucleotides in those particular tissues, the accumulation of which could otherwise lead to undesirable effects from long-term therapy utilizing degradation-resistant oligonucleotides. The oligonucleotides of the instant invention will generally include, in addition to the phosphodiester or phosphodiester-like internucleotide linkages at preferred internal positions, 5' and 3' ends that are resistant to degradation. Such degradation-resistant ends can involve any suitable modification that results in an increased resistance against exonuclease digestion over corresponding unmodified ends. For instance, the 5' and 3' ends can be stabilized by the inclusion there of at least one phosphate modification of the backbone. In a preferred embodiment, the at least one phosphate modification of the backbone at each end is independently a phosphorothioate, phosphorodithioate, methylphosphonate, or methylphosphorothioate internucleotide linkage. In another embodiment, the degradation-resistant end includes one or more nucleotide units connected by peptide or amide linkages at the 3' end. Yet other stabilized ends, including but not limited to those described further below, are meant to be encompassed by the invention.

As described above, the oligonucleotides of the instant invention include phosphodiester or phosphodiester-like linkages within and optionally adjacent to internal CG dinucleotides. Such CG dinucleotides are frequently part of immunostimulatory motifs. It is not necessary, however, that an oligonucleotide contain phosphodiester or phosphodiester-like linkages within every immunostimulatory motif. Additional phosphodiester or phosphodiester-like linkages may also be maintained for even more rapid renal digestion of these otherwise "stabilized oligonucleotides".

A phosphodiester internucleotide linkage is the type of linkage characteristic of nucleic acids found in nature. The phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNAse H. Thus for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. No. 5,177,198; U.S. Pat. No. 5,859,231; U.S. Pat. No. 6,160,109; U.S. Pat. No. 6,207,819; Sergueev et al., (1998) *J Am Chem Soc* 120:9417-27. In another preferred embodiment the phosphodiester-like internucleotide linkage is diasteriomerically pure Rp phosphorothioate. It is believed that diasteriomerically pure Rp phosphorothioate is more susceptible to nuclease digestion and is better at activating RNAse H than mixed or diastereomerically pure Sp phosphorothioate. It is to be noted that for purposes of the instant invention, the term "phosphodiester-like internucleotide linkage" specifically excludes phosphorodithioate and methylphosphonate internucleotide linkages.

The immunostimulatory oligonucleotide molecules of the instant invention have chimeric backbone. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could in one embodiment include at least one phosphodiester (phosphodiester or phosphodiester-like) linkage and at least one boranophosphonate (stabilized) linkage. In another embodiment a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endonuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation: peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) *Chem Rev* 90:544; Goodchild J (1990) *Bioconjugate Chem* 1:165. Methods for preparing chimeric oligonucleotides are also known. For instance patents issued to Uhlmann et al have described such techniques.

Mixed backbone modified ODN may be synthesized using a commercially available DNA synthesizer and standard phosphoramidite chemistry. (F. E. Eckstein, "Oligonucleotides and Analogues—A Practical Approach" *IRL Press. Oxford, UK,* 1991, and M. D. Matteucci and M. H. Caruthers, *Tetrahedron Lett.* 21, 719 (1980)) After coupling, PS linkages are introduced by sulfurization using the Beaucage reagent (R. P. Iyer, W. Egan, J. B. Regan and S. L. Beaucage, *J. Am. Chem. Soc.* 112, 1253 (1990)) (0.075 M in acetonitrile) or phenyl acetyl disulfide (PADS) followed by capping with acetic anhydride, 2,6-lutidine in tetrahydrofurane (1:1:8; v:v:v) and N-methylimidazole (16% in tetrahydrofurane). This capping step is performed after the sulfurization reaction to minimize formation of undesired phosphodiester (PO) linkages at positions where a phosphorothioate linkage should be located. In the case of the introduction of a phosphodiester linkage, e.g. at a CpG dinucleotide, the intermediate phosphorous-III is oxidized by treatment with a solution of iodine in water/pyridine. After cleavage from the solid support and final deprotection by treatment with concentrated ammonia (15 hrs at 50° C.), the ODN are analyzed by HPLC on a Gen-Pak Fax column (Millipore-Waters) using a NaCl-gradient (e.g. buffer A: 10 mM $NaH_2PO_4$ in acetonitrile/water=1:4/v:v pH 6.8; buffer B: 10 mM $NaH_2PO_4$, 1.5 M NaCl in acetonitrile/water=1:4/v:v; 5 to 60% B in 30 minutes at 1 ml/min) or by capillary gel electrophoresis. The ODN can be purified by HPLC or by FPLC on a Source High Performance column (Amersham Pharmacia). HPLC-homogeneous fractions are combined and desalted via a C18 column or by ultrafiltration. The ODN was analyzed by MALDI-TOF mass spectrometry to confirm the calculated mass.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

The oligonucleotides of the present invention are nucleic acids that contain specific sequences found to elicit an immune response. These specific sequences that elicit an immune response are referred to as "immunostimulatory motifs", and the oligonucleotides that contain immunostimulatory motifs are referred to as "immunostimulatory nucleic acid molecules" and, equivalently, "immunostimulatory nucleic acids" or "immunostimulatory oligonucleotides".

The immunostimulatory oligonucleotides of the invention thus include at least one immunostimulatory motif. In a preferred embodiment the immunostimulatory motif is an "internal immunostimulatory motif". The term "internal immunostimulatory motif" refers to the position of the motif sequence within a longer nucleic acid sequence, which is longer in length than the motif sequence by at least one nucleotide linked to both the 5' and 3' ends of the immunostimulatory motif sequence.

The immunostimulatory oligonucleotides include immunostimulatory motifs which are "CpG dinucleotides". A CpG dinucleotide can be methylated or unmethylated. An immunostimulatory oligonucleotide containing at least one unmethylated CpG dinucleotide is a nucleic acid molecule which contains an unmethylated cytosine-guanine dinucleotide sequence (i.e., an unmethylated 5' cytidine followed by 3' guanosine and linked by a phosphate bond) and which activates the immune system; such an immunostimulatory oligonucleotide is a CpG oligonucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068. An immunostimulatory oligonucleotide containing at least one methylated CpG dinucleotide is an oligonucleotide which contains a methylated cytosine-guanine dinucleotide sequence (i.e., a methylated 5' cytidine followed by a 3' guanosine and linked by a phosphate bond) and which activates the immune system.

It has recently been described that there are different classes of CpG oligonucleotides. One class is potent for activating B cells but is relatively weak in inducing IFN-α and NK cell activation; this class has been termed the B class. The B class CpG oligonucleotides typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the A class. The A class CpG oligonucleotides typically have stabilized poly-G sequences at 5' and 3' ends and a central palindromic phosphodiester CpG dinucleotide-containing sequence of at least 6 nucleotides. See, for example, published patent application PCT/US00/26527 (WO 01/22990).

Yet another class of CpG oligonucleotides activates B cells and NK cells and induces IFN-α; this class has been termed the C-class. The C-class CpG oligonucleotides, as first characterized, typically are fully stabilized, include a B class-type sequence and a GC-rich palindrome or near-palindrome. This class has been described in co-pending U.S. patent application Ser. No. 10/224,523, filed Aug. 19, 2002 and published as US2003/0148976 and US10/978,283 filed on Oct. 29, 2004, with a related PCT application published as WO2005/042018 the entire contents of which are incorporated herein by reference.

C-class oligonucleotides are also referred to as type C CpG ODN. In certain embodiments the C CpG ODN involve a combination of motifs wherein one motif is a CG-rich palindrome or a neutralizing motif, and another motif is a stimulatory motif; e.g., a CpG motif or the sequence TCGTCG.

The C CpG ODN may have the formula: 5' $X_1DCGHX_2$ 3'. $X_1$ and $X_2$ are independently any sequence 0 to 10 nucleotides long. D is a nucleotide other than C. C is cytosine. G is guanine. H is a nucleotide other than G. The nucleic acid sequence also includes a nucleic acid sequence selected from the group consisting of P and N positioned immediately 5' to $X_1$ or immediately 3' to $X_2$ N is a B-cell neutralizing sequence which begins with a CGG trinucleotide and is at least 10 nucleotides long. P is a GC-rich palindrome containing sequence at least 10 nucleotides long.

In some embodiments the immunostimulatory nucleic acid is 5' $NX_1DCGHX_2$ 3', 5' $X_1DCGHX_2N$ 3', 51 $PX_1DCGHX_2$ 3', 5<$X_1DCGHX_2P$ 3', 5' $X_1DCGHX_2PX_3$ 3', 5' $X_1DCGHPX_3$ 3', 5' $DCGHX_2PX_3$ 3', 5' $TCGHX_2PX_3$ 3', or 5' $DCGHPX_3$ 3'. $X_3$ is any sequence 0 to 10 nucleotides long. In other embodiments the immunostimulatory nucleic acid is 5' DCGHP 3'.

Optionally D and/or H are thymine (T).

In other embodiments H is T and $X_2$ is CG, CGT, CGTT, CGTTT, or CGTTTT.

H is T and $X_2$ is CG or CGTTTT according to other embodiments.

According to other embodiments C is unmethylated.

N includes at least four CG dinucleotides and no more than two CCG trinucleotides in some embodiments.

Optionally P includes at least one Inosine.

The nucleic acid may also include a poly-T sequence at the 5' end or the 3' end.

Alternatively the C CpG ODN may have the formula: 5' $N_1PyGN_2P$ 3'. G is guanine. $N_1$ is any sequence 1 to 6 nucleotides long. In some embodiments $N_1$ is at least 50% pyrimidines and preferably at least 50% T. In other embodiments $N_1$ includes at least one CG motif, at least one TCG motif, at least one CI motif, at least one TCI motif, at least one IG motif, or at least one TIG motif. $N_1$ is TCGG or TCGH in other embodiments. H is a nucleotide other than G.

Py is a pyrimidine. In some embodiments Py is an unmethylated C.

$N_2$ is any sequence 0 to 30 nucleotides long. In some embodiments $N_2$ is at least 50% pyrimidines or is at least 50% T. In other embodiments $N_2$ does not includes any poly G or poly A motifs.

P is a GC-rich palindrome containing sequence at least 10 nucleotides long. In some embodiments P is completely palindromic. In other embodiments P is a palindrome having between 1 and 3 consecutive intervening nucleotides. Optionally the intervening nucleotides may be TG. In other embodiments P includes at least 3, 4, or 5 C and at least 3, 4, or 5 G nucleotides. According to other embodiments P includes at least one Inosine.

In one embodiment the GC-rich palindrome has a base content of at least two-thirds G and C. In another embodiment the GC-rich palindrome has a base content of at least 81 percent G and C. In some embodiments the GC-rich palindrome is at least 12 nucleotides long. The GC-rich palindrome may be made up exclusively of C and G. In some embodiments the GC-rich palindrome can include at least one nucleotide that is neither C nor G.

In some embodiments the GC-rich palindrome includes at least one CGG trimer, at least one CCG trimer, or at least one CGCG tetramer. In some embodiments the GC-rich palindrome includes at least four CG dinucleotides. In certain preferred embodiments the GC-rich palindrome has a central CG dinucleotide.

In certain embodiments the GC-rich palindrome is CGGCGCGCGCCG (SEQ ID NO: 58), CGGCGGCCGCCG (SEQ ID NO: 59), CGACGATCGTCG (SEQ ID NO: 60) or CGACGTACGTCG (SEQ ID NO: 61).

In certain embodiments the GC-rich palindrome is CGCGCGCGCGCG (SEQ ID NO:62), GCGCGCGCGCGC (SEQ ID NO: 63), CCCCCCGGGGGG (SEQ ID NO: 64), GGGGGGCCCCCC (SEQ ID NO: 65), CCCCCGGGGG (SEQ ID NO: 66) or GGGGGCCCCC (SEQ ID NO: 67).

In some embodiments $N_1PyGN_2$ is a sequence selected from the group consisting of TTTTTCG, TCG, TTCG, TTTCG, TTTTCG, TCGT, TTCGT, TTTCGT, and TCGTCGT.

An immunostimulatory nucleic acid of 13-100 nucleotides in length is provided according to other aspects of the invention. The nucleic acid has the formula: 5' $N_1PyG/IN_2P$ 3'. G/I refers to single nucleotide which is either a G or an I. G is guanine and I is Inosine.

$N_1$ is any sequence 1 to 6 nucleotides long. Py is a pyrimidine. $N_2$ is any sequence 0 to 30 nucleotides long.

P is a palindrome containing sequence at least 10 nucleotides long. In some embodiments P is a GC-rich palindrome. In other embodiments P is an IC-rich palindrome.

$N_1PyIN_2$ in some embodiments is TCITCITTTT (SEQ ID NO: 62).

A class of oligonucleotides referred to herein as modified C-class oligonucleotides are characteristically monomeric in solution. It is believed that these nucleic acid molecules can form intramolecular duplex structures in vitro, rendering them stable against nuclease digestion. It is also believed that these same nucleic acid molecules can form intermolecular duplex and possibly even higher order structures within the environment of the intraendosomal compartment, where they are believed to exert their biological activity.

Modified C-class oligonucleotides have 3 general formulas. Formula I

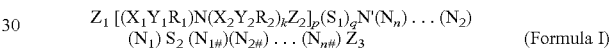

$$Z_1 [(X_1Y_1R_1)N(X_2Y_2R_2)_kZ_2]_p(S_1)_qN'(N_n)\ldots(N_2)(N_1) S_2 (N_{1\#})(N_{2\#})\ldots(N_{n\#}) Z_3 \quad \text{(Formula I)}$$

wherein each of $Z_1$, $Z_2$, and $Z_3$ is independently any sequence 0 to 12 nucleotides long which optionally includes a non-nucleotidic linker or abasic dSpacer; each of $X_1$ and $X_2$ is independently a thymidine, deoxyuridine, deoxyadenosine or a 5-substituted deoxyuridine; each of $Y_1$ and $Y_2$ is independently a cytosine (C) or a modified cytosine; each of $R_1$ and $R_2$ is independently a guanine (G) or a modified guanine; each of N and N' is independently any sequence 0 to 12 nucleotides long which optionally includes a non-nucleotidic linker or abasic dSpacer; $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3-internucleoside linkages; $S_2$ is any non-palindromic sequence 1 to 10 nucleotides long or a non-nucleotidic linker, an abasic linker (dSpacers), triethylene glycol units or hexaethylene glycol units; each of $N_1$, $N_2$, ... $N_n$, and $N_{1\#}$, $N_{2\#}$ ... $N_{n\#}$ is any nucleotide or modified nucleotide wherein $N_1$ base-pairs with $N_{1\#}$, $N_2$ base-pairs with $N_{2\#}$, ... and $N_n$ base-pairs with $N_{n\#}$; k is an integer from 0 to 5; n is an integer from 2 to 16; p is an integer from 1 to 6; and q is an integer from 0 to 10, and wherein when $(N_n)\ldots(N_2)(N_1) S_2 (N_{1\#})(N_{2\#})\ldots(N_{n\#})$ is 10 to 42 nucleotides long, $S_2$ is 4 to 10 nucleotides long, $S_2$ comprises a non-nucleotidic linker, an abasic linker (dSpacers), triethylene glycol units or hexaethylene glycol units, and/or $(N_n)\ldots(N_2)(N_1) S_2 (N_{1\#})(N_{2\#})\ldots(N_{n\#})$ has a GC content that is less than ⅔.

In one embodiment each of $N_1$, $N_2$, ... $N_n$, and $N_{1\#}$, $N_{2\#}$, ... $N_{n\#}$ is chosen from C, G, or modifications thereof, wherein C base-pairs with G.

In one embodiment each of $N_1$, $N_2$, ... $N_n$, and $N_{1\#}$, $N_{2\#}$, ... $N_{1\#}$ is chosen from T, A, or modifications thereof, and T base-pairs with A.

In these and other embodiments each of C, G, A, and T can refer to deoxynucleotides with corresponding bases cytosine, guanine, adenine, and thymine.

In one embodiment each of $N_1$, $N_2$ ... $N_n$, and $N_{1\#}$, $N_{2\#}$, ... $N_{n\#}$ is chosen from C, T, A, G, or modifications thereof, and C base-pairs with G, T base-pairs with G, A base-pairs with T, and A base-pairs with G.

In one embodiment each of $N_1$, $N_2$, ... $N_n$, and $N_{1\#}$, $N_{2\#}$, ... $N_{n\#}$ is chosen from unmodified or modified nucleotides which form Watson-Crick basepairs.

In one embodiment each of $N_1$, $N_2$ ... $N_n$, and $N_{1\#}$, $N_{2\#}$ ... $N_{n\#}$ is chosen from unmodified or modified nucleotides which form non-Watson-Crick basepairs.

In one embodiment the immunostimulatory nucleic acid molecule includes a partially stabilized backbone with at least one phosphodiester bond.

In one embodiment the immunostimulatory nucleic acid molecule includes a backbone with at least one stabilized internucleotide linkage.

In one embodiment internucleotide linkages of the oligonucleotide are all phosphorothioate linkages.

In one embodiment the immunostimulatory nucleic acid molecule includes a partially stabilized backbone with a phosphodiester bond joining at least one of $Y_1R_1$ or $Y_2R_2$.

In one embodiment $Y_1$ is C.

In one embodiment $R_1$ is G.

In one embodiment $Y_1$ is C and $R_1$ is G.

In one embodiment $X_1$ or $X_2$ is T.

In one embodiment $X_1$ is T, $X_2$ is T, $Y_1$ is C, $R_1$ is G, and k is 1.

In one embodiment $X_1$ is T, $X_2$ is T, $Y_1$ is C, $R_1$ is G, k is 1, p is 1, N and N' and $Z_3$ each contain zero nucleotides, and $Z_2$ is TTTT or d(UUUU).

In one embodiment $S_2$ is a non-nucleotidic linker.

In one embodiment $S_2$ contains at least one abasic dSpacer residue.

In one embodiment the oligonucleotide includes at least one branched non-nucleoside linkage.

In one embodiment the immunostimulatory nucleic acid molecule includes at least one doubler unit, at least one trebler unit, or at least one doubler unit and at least one trebler unit.

In one embodiment $S_1$ is a doubler unit or a trebler unit.

In one embodiment the oligonucleotide includes at least one 2'5'-, 5'5'-, 3'3'-, 2'2'-, or 2'3'-internucleoside linkage.

In one aspect the invention provides an immunostimulatory nucleic acid molecule of Formula II

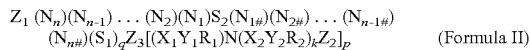   (Formula II)

wherein each of $Z_1$, $Z_2$, and $Z_3$ is independently any sequence 0 to 12 nucleotides long which optionally includes a non-nucleotidic linker or abasic dSpacer; each of $X_1$ and $X_2$ is independently a thymidine, deoxyuridine, deoxyadenosine or a 5-substituted deoxyuridine; each of $Y_1$ and $Y_2$ is independently a cytosine (C) or a modified cytosine; each of $R_1$ and $R_2$ is independently a guanine (G) or a modified guanine; N is any sequence 0 to 12 nucleotides long which optionally includes a non-nucleotidic linker or abasic dSpacer; $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages; $S_2$ is any non-palindromic sequence 1 to 10 nucleotides long or a non-nucleotidic linker, an abasic linker (dSpacers), triethylene glycol units or hexaethylene glycol units; each of $N_1$, $N_2$, ... $N_{n-1}$, $N_n$, and $N_{1\#}$, $N_{2\#}$, $N_{n-1\#}$, $N_{n\#}$ is any nucleotide or modified nucleotide wherein $N_1$ base-pairs with $N_{1\#}$, $N_2$ base-pairs with $N_{2\#}$, ... $N_{n-1}$ base-pairs with $N_{n-1\#}$, and $N_n$ base-pairs with $N_{n\#}$; k is an integer from 0 to 5; n is an integer from 2 to 16; p is an integer from 1 to 6; and q is an integer from 0 to 10, and wherein when $(N_n)$ ... $(N_2)(N_1) S_2 (N_{1\#})(N_{2\#})$ ... $(N_{n\#})$ is 10 to 42 nucleotides long, $S_2$ is 4 to 10 nucleotides long, $S_2$ comprises a non-nucleotidic linker, an abasic linker (dSpacers), triethylene glycol units or hexaethylene glycol units, and/or $(N_n)$ ... $(N_2)(N_1)S_2 (N_{1\#})(N_{2\#})$ ... $(N_{n\#})$ has a GC content that is less than $2/3$.

In one embodiment $Z_1 (N_n)(N_{n-1})$ is TYR, where Y is a cytosine or a modified cytosine and R is a guanine or a modified guanine.

In one embodiment each of $N_1$, $N_2$, ... $N_{n-1}$, $N_n$, and $N_{1\#}$, $N_{2\#}$, ... $N_{n-1\#}$, $N_{n\#}$ is chosen from C, G, or modifications thereof, wherein C base-pairs with G.

In one embodiment each of $N_1$, $N_2$, ... $N_{n-1}$, $N_n$, and $N_{1\#}$, $N_{2\#}$, ... $N_{n-\#}$, $N_{n\#}$ is chosen from T, A, or modifications thereof, and T base-pairs with A.

In these and other embodiments each of C, G, A, and T can refer to deoxynucleotides with corresponding bases cytosine, guanine, adenine, and thymine.

In one embodiment each of $N_1$, $N_2$, ... $N_{n-1}$, $N_n$, and $N_{1\#}$, $N_{2\#}$, ... $N_{n-1\#}$, $N_{n\#}$ is chosen from C, T, A, G, or modifications thereof, and C base-pairs with G, T base-pairs with G, A base-pairs with T, and A base-pairs with G.

In one embodiment each of $N_1$, $N_2$, ... $N_{n-\#}$, $N_n$, and $N_{1\#}$, $N_{2\#}$, ... $N_{n-\#}$, $N_{n\#}$, is chosen from unmodified or modified nucleotides which form Watson-Crick basepairs.

In one embodiment each of $N_1$, $N_2$, ... $N_{n-1}$, $N_n$, and $N_{1\#}$, $N_{2\#}$, ... $N_{n-\#}$, $N_{n\#}$ is chosen from unmodified or modified nucleotides which form non-Watson-Crick basepairs.

In one embodiment the immunostimulatory nucleic acid molecule includes a partially stabilized backbone with at least one phosphodiester bond.

In one embodiment the immunostimulatory nucleic acid molecule includes a backbone with at least one stabilized internucleotide linkage.

In one embodiment internucleotide linkages of the oligonucleotide are all phosphorothioate linkages.

In one embodiment the immunostimulatory nucleic acid molecule includes a partially stabilized backbone with a phosphodiester bond joining at least one of $Y_1R_1$ or $Y_2R_2$.

In one embodiment $Y_1$ is C.

In one embodiment $R_1$ is G.

In one embodiment $Y_1$ is C and $R_1$ is G.

In one embodiment $X_1$ or $X_2$ is T.

In one embodiment $X_1$ is T, $X_2$ is T, $Y_1$ is C, $R_1$ is G, and k is 1.

In one embodiment $X_1$ is T, $X_2$ is T, $Y_1$ is C, $R_1$ is G, k is 1, p is 1, N and N' and $Z_3$ each contain zero nucleotides, and $Z_2$ is TTTT or d(UUUU).

In one embodiment $S_2$ is a non-nucleotidic linker.

In one embodiment $S_2$ contains at least one abasic dSpacer residue.

In one embodiment the oligonucleotide includes at least one branched non-nucleoside linkage.

In one embodiment the immunostimulatory nucleic acid molecule includes at least one doubler unit, at least one trebler unit, or at least one doubler unit and at least one trebler unit.

In one embodiment $S_1$ is a doubler unit or a trebler unit.

In one embodiment the oligonucleotide includes at least one 2'5'-, 5'5'-, 3'3'-, 2'2'-, or 2'3'-internucleoside linkage.

In one aspect the invention provides an immunostimulatory nucleic acid molecule of Formula III

   (Formula III)

wherein U is $Z_1 [(X_1Y_1R_1) N(X_2Y_2R_2)_k Z_2]_p (S_1)_q$ N' $(N_n)$ ... $(N_3)(N_2)(N_1) S_2 (N_{1\#})(N_{2\#})(N_{3\#})$ ... $(N_{n\#})$; each of $Z_1$, $Z_2$, and $Z_3$ is independently any sequence 0 to 12 nucleotides long which optionally includes a non-nucleotidic linker or abasic dSpacer; each of $X_1$ and $X_2$ is independently a thymidine, deoxyuridine, deoxyadenosine or a 5-substituted deoxyuridine; each of $Y_1$ and $Y_2$ is independently a cytosine or a modified cytosine; each of $R_1$ and $R_2$ is independently a guanine or a modified guanine; each of N and N' is independently any sequence 0 to 12 nucleotides long which optionally includes a non-nucleotidic linker or abasic dSpacer; $S_1$ is a non-nucleotidic linker, an abasic linker (dSpacers), triethylene glycol units or hexaethylene glycol units, which optionally provides for 2'5'-, 5'5'-, 3'3'-, 2'2'-, or 2'3'-internucleoside linkages; $S_2$ is any non-palindromic sequence 1 to 10 nucleotides long or a non-nucleotidic linker, an abasic linker (dSpacers), triethylene glycol units or hexaethylene glycol units; $S_3$ is a direct or indirect 2'5'-, 5'5'-, 3'3'-, 2'2'-, or 2'3'-internucleoside linkage, or a non-nucleotidic linker, said non-nucleotidic linker including abasic linkers (dSpacers), triethylene glycol units, or hexaethylene glycol units facilitating a 2'5'-, 5'5'-, 3'3'-, 2'2'-, or 2'3'-linkage of m sequence parts; each of $N_1, N_2, \ldots N_n$, and $N_{1\#}, N_{2\#}, \ldots N_{n\#}$ is any nucleotide or modified nucleotide wherein $N_1$ base-pairs with $N_{1\#}$, $N_2$ base-pairs with $N_{2\#}$, $N_3$ base-pairs with $N_{3\#}$, ... and $N_n$ base-pairs with $N_{n\#}$; k is an integer from 0 to 5; m is an integer from 2 to 10; n is an integer from 2 to 16; p is an integer from 1 to 6; and q is an integer from 0 to 10.

In certain embodiments $Z_1 [(X_1Y_1R_1) N(X_2Y_2R_2)_k Z_2]_p (S_1)_q$ is a non-palindromic sequence.

In certain embodiments $Z_1 [(X_1Y_1R_1) N (X_2Y_2R_2)_k Z_2]_p (S_1)_q$ is TCGTCGTTTT (SEQ ID NO:29), TCGTCGTTDD (SEQ ID NO:30), TCGA, TCGAC, TCGACGTC, or TCGACGTCG, wherein D is dSpacer.

In certain embodiments $Z_1 [(X_1Y_1R_1) N (X_2Y_2R_2)_k Z_2]_p (S_1)_q$ is a palindromic sequence.

In certain embodiments $Z_1 [(X_1Y_1R_1) N (X_2Y_2R_2)_k Z_2]_p (S_1)_q$ is TCGACGTCGA (SEQ ID NO:31) or TCGTCGACGA (SEQ ID NO:32).

In certain embodiments $Z_1 [(X_1Y_1R_1) N (X_2Y_2R_2)_k Z_2]_p (S_1)_q$ is TCGCGACGTT (SEQ ID NO:33) or TCGCGTCGTT (SEQ ID NO:34).

In one embodiment $(N_n) \ldots (N_2)(N_1) S_2 (N_{1\#})(N_{2\#}) \ldots (N_{n\#}) Z_3$ includes a sequence AGCGAAGCT, CAATATT-TATTG (SEQ ID NO:35), CCGTTTTTGG (SEQ ID NO:36), CGGCGCCGTGCCG (SEQ ID NO:37), CGGCGCCGT-TGCCG (SEQ ID NO:38), CGGCGDDCGCCG (SEQ ID NO:39), CGGCGDDDTGCCG (SEQ ID NO:40), CGGCG-GDDCCGCCG (SEQ ID NO:41), CGGCGTCGCCGCCG (SEQ ID NO:42), CGTCGACGGGACGGG (SEQ ID NO:43), CGTCGACGTGACGGG (SEQ ID NO:44), GAGAGTTGGGCTCTC (SEQ ID NO:45), GTCGAG-GAGGT (SEQ ID NO:46), TAATADDTATTA (SEQ ID NO:47), TAATATCCATTA (SEQ ID NO:48), or TAATATT-TATTA (SEQ ID NO:49), wherein D is dSpacer.

In one embodiment $(N_n) \ldots (N_2)(N_1) S_2 (N_{1\#})(N_{2\#}) \ldots (N_{n\#})$ includes a sequence GGCGCGCTGCCG (SEQ ID NO:50).

In one embodiment the 5' end of the nucleic acid begins with an immunostimulatory motif chosen from $(TCG)_nN$ and $R\underline{D}CGY_1Y_2N$. T is thymine, C is unmethylated cytosine, G is guanine, R is a purine, $\underline{D}$ is not C, each of $Y_1$ and $Y_2$ independently is a pyrimidine, n is an integer between 1 and 4, inclusive, and N is any sequence 0-12 bases long.

The 3' end of the nucleic acid terminates in an inverted repeat capable of forming a hairpin or stem-loop structure. The term "terminates" refers to a structure at or near the 3' end. Thus, the end of the near palindrome may be positioned at the actual 3' end of the molecule or alternatively the 3' end may include 1 or more additional nucleotides that are not part of the inverted repeat structure. Preferably the 3' end of the molecule includes 3 or fewer nucleotides that do not form part of the inverted repeat structure.

In one embodiment an "inverted repeat capable of forming a hairpin or stem-loop structure" as used herein refers to a sequence of nucleotides that forms a GC-rich stem or hairpin that is 2 to 10 consecutive base pairs long, and includes at least one unmatched or mismatched base. In individual embodiments the GC-rich stem is 2, 3, 4, 5, 6, 7, 8, 9, or consecutive base pairs long. In some embodiments the GC-rich stem includes at least 2, 3, or 4 G-C base pairs.

In one embodiment an "inverted repeat capable of forming a hairpin or stem-loop structure" as used herein refers to a sequence of nucleotides that forms an AT-rich stem or hairpin that is 2 to 10 consecutive base pairs long, and includes at least one unmatched or mismatched base. In individual embodiments the AT-rich stem is 2, 3, 4, 5, 6, 7, 8, 9, or 10 consecutive base pairs long. In some embodiments the AT-rich stem includes at least 2, 3, or 4 A-T base pairs.

In some instances the at least one unmatched or mismatched base bridges the ends of the stem or hairpin. This may allow the formation of the secondary structure by providing a flexible point in the molecule for the stems to base pair and form a hairpin. Alternatively the unmatched or mismatched base(s) may be within the stem. Preferably if the mismatched base is within the stem, then the stem is at least 3 basepairs long. The unmatched or mismatched bases(s) may be any nucleotide. In some embodiments the unmatched or mismatched base is a T. Unmatched nucleotides at the end of double-strands are also known as overhanging nucleotides or dangling ends which can significantly stabilize duplex formation or hairpin formation. Freier S M et al. (1983) Effects of 3' dangling end stacking on the stability of GGCC and CCGG double helixes. *Biochemistry* 22:6198-206.

The nucleic acid also includes a partially stabilized backbone including at least one phosphodiester 5'-CpG-3' linkage.

In some instances the double-stranded part of the molecule may also contain unnatural (non-standard) basepairs (e.g., diaminopyridine paired with xanthosinc). Lutz M J et al. (1998) Recognition of a non-standard base pair by thermostable DNA polymerases. *Bioorg Med Chem Lett* 8:1149-52.

The formulas define subsets of the class of CpG oligonucleotides which demonstrated excellent immune stimulating properties. In the formulas 5' refers to the free 5' end of the oligonucleotide and 3' refers to the free 3' end of the oligonucleotide.

The oligonucleotides may have one or more accessible 5' or 3' ends. In some embodiments a 3' end can be linked to another 3' end. Since the importance of the 5' and 3' motifs has been discovered and described herein, it is also possible to create modified oligonucleotides having two such 5' or 3' ends. This may be achieved, for instance by attaching two oligonucleotides through a 3'-3' linkage to generate an oligonucleotide having one or two accessible 5' ends. Such a structure might have a formula such as 5'-R$\underline{D}$CGY$_1$Y$_2$N-NY$_2$Y$_1$GC$\underline{D}$R-5' (wherein $\underline{D}$ represents not C; SEQ ID NO:51) or 5'-(TCG)$_n$N—N(GCT)$_n$-5' (SEQ ID NO:52). The 3'3'- or 5'5'-linkage may be a phosphodiester, phosphorothioate, or any other modified internucleoside bridge. Methods for accomplishing such linkages are known in the art. For instance, such linkages have been described in Seliger H et al. (1991) Oligonucleotide analogs with terminal 3'-3'- and 5'-5'-internucleotidic linkages as antisense inhibitors of viral gene expression, *Nucleosides & Nucleotides* 10:469-77 and Jiang Z et al. (1999) Pseudo-cyclic oligonucleotides: in vitro and in vivo properties, *Bioorg Med Chem* 7:2727-35.

In some embodiments the oligonucleotide has one of the following structures:

| | |
|---|---|
| TCGTCGTTTTA, | (SEQ ID NO:53) |
| CGGCGCCGTGCCG, | (SEQ ID NO:54) |
| CGGCGTCGTGCCG, | (SEQ ID NO:55) |
| TCGTCGTTTTACGGCGCCGTGCCG, | (SEQ ID NO:56) |
| TCGTCGTTTTACGGCGTCGTGCCG, | (SEQ ID NO:57) |

The invention in one aspect involves the finding that a specific sub-class of C-class CpG immunostimulatory oligonucleotides having a chimeric backbone is highly effective in mediating immune stimulatory effects. These CpG oligonucleotides are useful therapeutically and prophylactically for stimulating the immune system to treat cancer, infectious diseases, allergy, asthma, autoimmune disease, and other disorders and to help protect against opportunistic infections following cancer chemotherapy. The strong yet balanced, cellular and humoral immune responses that result from CpG stimulation reflect the body's own natural defense system against invading pathogens and cancerous cells.

The invention involves, in one aspect, the discovery that a subset of CpG immunostimulatory oligonucleotides have improved immune stimulatory properties and reduced renal inflammatory effect. In some instances, renal inflammation has been observed in subjects that have been administered a completely phosphorothioate oligonucleotide. It is believed that the chimeric oligonucleotides described herein produce less renal inflammation than fully phosphorothioate oligonucleotides. Additionally these oligonucleotides are highly effective in stimulating an immune response. Thus, the phosphodiester region of the molecule did not reduce it's affectivity.

The preferred CpG immunostimulatory oligonucleotides fall within one of the following 7 general formulas:

5' TTC_GX$_2$C_GN$_1$X$_1$_GX$_3$C_GTT 3' (SEQ ID NO.: 24) wherein N$_1$ is 1-3 nucleotides in length with N referring to any nucleotide, X$_1$ is a pyrimidine, X$_2$ and X$_3$ are any nucleotide.

5' TTC_GTC_GTTTX$_1$_GTC_GTT 3' (SEQ ID NO.: 25), wherein X$_1$ is a pyrimidine.

```
                                    (SEQ ID NO.: 25)
    5' T*T*C_G*T*C*T*T*T*X₁_G*T*C_G*T*T 3',
``` wherein X$_1$ is a pyrimidine.

5' TC_GX$_1$C_G X$_2$N$_1$ X$_3$C_GN$_2$CG 3' (SEQ ID NO.: 26), wherein N$_1$ is 0-3 nucleotides in length, N$_2$ is 0-9 nucleotides in length with N referring to any nucleotide and X$_1$, X$_2$, and X$_3$ are any nucleotide.

5' TC_GTC_GTN$_1$TC_GGCGCN$_1$GCCG 3' (SEQ ID NO.: 27), wherein N$_1$ is 0-3 nucleotides in length.

```
                                    (SEQ ID NO.: 27)
    5' T*C_G*T*C_G*T*N₁*T*C_G*G*C*G*CN₁G*C*C*G 3',
``` wherein N$_1$ is 0-3 nucleotides in length.

5' TC_G X$_1$C_G X$_2$C_G X$_3$TC_GGCGC_G N$_3$ 3' (SEQ ID NO.: 28), wherein N$_3$ is 1-5 nucleotides in length with N referring to any nucleotide and X$_1$, X$_2$, and X$_3$ are any nucleotide.

Optionally, when specified in the formula, 5' refers to the free 5' end of the oligonucleotide and 3' refers to the free 3' end of the oligonucleotide.

The symbol * used in the formulas refers to the presence of a stabilized internucleotide linkage. The symbol _ in these structures refers to the presence of a phosphodiester internucleotide linkage. The internucleotide linkages not marked with an * may be stabilized or unstabilized, as long as the oligonucleotide includes at least 2-3 phosphodiester or phosphodiester like internucleotide linkages. In some embodiments it is preferred that the oligonucleotides include 3-6 phosphodiester or phosphodiester like linkages. In some cases the linkages between the CG motifs are phosphodiester and in other cases they are phosphorothioate or other stabilized linkages.

In some embodiment the oligonucleotide has one of the following structures:

```
                                              (SEQ ID NO: 2)
T*C_G*T*C_G*T*C_G*T*T*C_G*G*C*G*C_G*C*G*C*C*G (SEQ ID NO: 3)
T*C_G*T*C_G*T*T*C_G*G*C*G*C*G*C*C*G (SEQ ID NO: 4)
TC_GTC_GAC_GATC_GGCGC_GCGCCG (SEQ ID NO: 4)
T*C_G*T*C_G*A*C_G*A*T*C_G*G*C*G*C_G*C*G*C*C*G (SEQ ID NO: 5)
T*T*C_G*T*C_G*T*T*T*T_G*T*C_G*T*T (SEQ ID NO: 6)
T*T*T*C_G*T*C_G*T*T*T*C_G*T*C_G*T*T (SEQ ID NO: 3)
TCGTCGTTCGGCGCGCCG (SEQ ID NO: 2)
TCGTCGTCGTTCGGCGCGCGCCG (SEQ ID NO: 4)
TCGTCGACGATCGGCGCGCGCCG (SEQ ID NO: 5)
TTCGTCGTTTTGTCGTT (SEQ ID NO: 6)
TTTCGTCGTTTCGTCGTT

TCGTCGTC

CGTCGTCG

GTCGTCGT

TCGTCGTT

CGTCGTTC

GTCGTTCG

TCGTTCGG

CGTTCGGC

GTTCGGCG

TTCGGCGC

TCGGCGCG

CGGCGCGC

GGCGCGCG

GCGCGCGC

CGCGCGCC
```

```
-continued

GCGCGCCG.

T*C_G*T*C_G*T*C

C_G*T*C_G*T*C_G

G*T*C_G*T*C_G*T

T*C_G*T*C_G*T*T

C_G*T*C_G*T*T*C

G*T*C_G*T*T*C_G

T*C_G*T*T*C_G*G

C_G*T*T*C_G*G*C

G*T*T*C_G*G*C*G

T*T*C_G*G*C*G*C

T*C_G*G*C*G*C_G

C_G*G*C*G*C_G*C

G*G*C*G*C_G*C*G

G*C*G*C_G*C*G*C

C*G*C_G*C*G*C*C

G*C_G*C*G*C*C*G
```

The terms "nucleic acid" and "oligonucleotide" also encompass nucleic acids or oligonucleotides with substitutions or modifications, such as in the bases and/or sugars. For example, they include oligonucleotides having backbone sugars that are covalently attached to low molecular weight organic groups other than a hydroxyl group at the 2' position and other than a phosphate group or hydroxy group at the 5' position. Thus modified oligonucleotides may include a 2'-O-alkylated ribose group. In addition, modified oligonucleotides may include sugars such as arabinose or 2'-fluoroarabinose instead of ribose. Thus the oligonucleotides may be heterogeneous in backbone composition thereby containing any possible combination of polymer units linked together such as peptide-nucleic acids (which have an amino acid backbone with nucleic acid bases).

Nucleic acids also include substituted purines and pyrimidines such as C-5 propyne pyrimidine and 7-deaza-7-substituted purine modified bases. Wagner R W et al. (1996) Nat Biotechnol 14:840-4. Purines and pyrimidines include but are not limited to adenine, cytosine, guanine, thymine, 5-methylcytosine, 5-hydroxycytosine, 5-fluorocytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

The immunostimulatory oligonucleotides of the instant invention can encompass various chemical modifications and substitutions, in comparison to natural RNA and DNA, involving a phosphodiester internucleotide bridge, a β-D-ribose unit and/or a natural nucleotide base (adenine, guanine, cytosine, thymine, uracil). Examples of chemical modifications are known to the skilled person and are described, for example, in Uhhlmann E et al. (1990) Chem Rev 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) Annu Rev Pharmacol Toxicol 36:107-129; and Hunziker J et al. (1995) Mod Synth Methods 7:331-417. An oligonucleotide according to the invention may have one or more modifications, wherein each modification is located at a particular phosphodiester internucleotide bridge and/or at a particular β-D-ribose unit and/or at a particular natural nucleotide base position in comparison to an oligonucleotide of the same sequence which is composed of natural DNA or RNA.

For example, the invention relates to an oligonucleotide which may comprise one or more modifications and wherein each modification is independently selected from:
a) the replacement of a phosphodiester internucleotide bridge located at the 3' and/or the 5' end of a nucleotide by a modified internucleotide bridge,
b) the replacement of phosphodiester bridge located at the 3' and/or the 5' end of a nucleotide by a dephospho bridge,
c) the replacement of a sugar phosphate unit from the sugar phosphate backbone by another unit,
d) the replacement of a β-D-ribose unit by a modified sugar unit, and
e) the replacement of a natural nucleotide base by a modified nucleotide base.

More detailed examples for the chemical modification of an oligonucleotide are as follows.

A phosphodiester internucleotide bridge located at the 3' and/or the 5' end of a nucleotide can be replaced by a modified internucleotide bridge, wherein the modified internucleotide bridge is for example selected from phosphorothioate, phosphorodithioate, $NR^1R^2$-phosphoramidate, boranophosphate, α-hydroxybenzyl phosphonate, phosphate-$(C_1-C_{21})$—O-alkyl ester, phosphate-[$(C_6-C_{12})$aryl-$(C_1-C_{21})$—O-alkyl]ester, $(C_1-C_8)$alkylphosphonate and/or $(C_6-C_{12})$arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleotide by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

A sugar phosphate unit (i.e., a β-D-ribose and phosphodiester internucleotide bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) Nucleic Acids Res 17:6129-41), that is, e.g., the replacement by a morpholino-derivative unit; or to build up a polyamide nucleic acid ("PNA"; as described for example, in Nielsen P E et al. (1994) Bioconjug Chem 5:3-7), that is, e.g., the replacement by a PNA backbone unit, e.g., by 2-aminoethylglycine.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O—($C_1$-$C_6$)alkyl-ribose, preferably 2'-O—($C_1$-$C_6$) alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'—$NH_2$-2'-deoxyribose, β-D-xylo-furanose, a-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) Tetrahedron 49:7223) and/or bicyclosugar analogs (described, for example, in Tarkov M et al. (1993) *Helv Chim Acta* 76:481).

In some preferred embodiments the sugar is 2'-O-methylribose, particularly for one or both nucleotides linked by a phosphodiester or phosphodiester-like internucleotide linkage.

A modified base is any base which is chemically distinct from the naturally occurring bases typically found in DNA and RNA such as T, C, G, A, and U, but which share basic chemical structures with these naturally occurring bases. The modified nucleotide base may be, for example, selected from hypoxanthine, uracil, dihydrouracil, pseudouracil, 2-thiouracil, 4-thiouracil, 5-aminouracil, S—($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleotides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleotide bases. This list is meant to be exemplary and is not to be interpreted to be limiting.

The oligonucleotides may have one or more accessible 5' ends. It is possible to create modified oligonucleotides having two such 5' ends. This may be achieved, for instance by attaching two oligonucleotides through a 3'-3' linkage to generate an oligonucleotide having one or two accessible 5' ends. The 3'3'-linkage may be a phosphodiester, phosphorothioate or any other modified internucleotide bridge. Methods for accomplishing such linkages are known in the art. For instance, such linkages have been described in Seliger, H.; et al., Oligonucleotide analogs with terminal 3'-3'- and 5'-5'-internucleotidic linkages as antisense inhibitors of viral gene expression, Nucleotides & Nucleotides (1991), 10(1-3), 469-77 and Jiang, et al., Pseudo-cyclic oligonucleotides: in vitro and in vivo properties, Bioorganic & Medicinal Chemistry (1999), 7(12), 2727-2735.

Additionally, 3' 3'-inked oligonucleotides where the linkage between the 3'-terminal nucleotides is not a phosphodiester, phosphorothioate or other modified bridge, can be prepared using an additional spacer, such as tri- or tetra-ethylenglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

It recently has been reported that CpG oligonucleotides appear to exert their immunostimulatory effect through interaction with Toll-like receptor 9 (TLR9). Hemmi H et al. (2000) *Nature* 408.740-5. TLR9 signaling activity thus can be measured in response to CpG oligonucleotide or other immunostimulatory oligonucleotide by measuring NF-κB, NF-κB-related signals, and suitable events and intermediates upstream or downstream of NF-κB.

For use in the instant invention, the oligonucleotides of the invention can be synthesized de novo using any of a number of procedures well known in the art. For example, the b-cyanoethyl phosphoramidite method (Beaucage, S. L., and Caruthers, M. H., *Tet. Let.* 22:1859, 1981); and nucleotide H-phosphonate method (Garegg et al., *Tet. Let.* 27:4051-4054, 1986; Froehler et al., *Nucl. Acid. Res.* 14:5399-5407, 1986, Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

The oligonucleotides are partially resistant to degradation (e.g., are stabilized). A "stabilized oligonucleotide molecule" shall mean an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases. Other modified oligonucleotides include phosphodiester modified oligonucleotides, combinations of phosphodiester and phosphorothioate oligonucleotide, methylphosphonate, methylphosphorothioate, phosphorodithioate, p-ethoxy, and combinations thereof.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., *Chem. Rev.* 90:544, 1990; Goodchild, J., *Bioconjugate Chem.* 1:165, 1990).

Other stabilized oligonucleotides include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Oligonucleotides which contain diol, such as tetraethyleneglycol or hexaethyleneglycol, at either or both termini have also been shown to be substantially resistant to nuclease degradation.

It has been discovered according to the invention that the subsets of CpG immunostimulatory oligonucleotides have dramatic immune stimulatory effects on human cells such as PBMC cells, suggesting that these CpG immunostimulatory oligonucleotides are effective therapeutic agents for human vaccination, cancer immunotherapy, asthma immunotherapy, general enhancement of immune function, enhancement of hematopoietic recovery following radiation or chemotherapy, autoimmune disease and other immune modulatory applications. It has also been demonstrated that the subsets of CpG immunostimulatory oligonucleotides are useful in vivo for the treatment of asthma and allergic rhinitis.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Allergies are generally caused by IgE antibody generation against harmless allergens. The cytokines that are induced by systemic or mucosal administration of CpG immunostimulatory oligonucleotides are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the CpG immunostimulatory oligonucleotides to shift the immune response in a subject from a predominant Th2 (which is associated with production of IgE antibodies and allergy) to a balanced Th2/Th1 response (which is protective against allergic reactions), an effective dose for inducing an immune response of a CpG immunostimulatory oligonucleotide as a stand alone therapy without allergen or in combination with allergen can be administered to a subject to treat or prevent asthma and allergy.

Thus, the CpG immunostimulatory oligonucleotides have significant therapeutic utility in the treatment of allergic conditions such as asthma and allergic rhinitis. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

Asthma may be exacerbated by viral infections. The combination of asthma and viral infections significantly worsens the symptoms in a subject. The oligonucleotides used herein provide significant benefits for the treatment of viral induced exacerbation of asthma. Several examples of such therapy are presented below.

Allergic rhinitis is a disorder resulting in inflammation of the nasal mucosa caused by allergens such as pollen or dust. The term includes rhinitis medicamentosa, rhinitis sicca, and atrophic rhinitis. There are two general types of allergic rhinitis, seasonal and perennial. Seasonal allergic rhinitis is normally referred to as hay fever and is usually caused by mould or pollen. Perennial allergic rhinitis is usually caused by an inherent sensitivity to one or more types of allergen. This condition generally continues throughout the year or for as long as the patient is exposed to the allergen. Both types of allergic rhinitis involve a type 1 (IgE-mediated) hypersensitivity that leads to inflammation. This inflammation is thought to be caused by an excessive degranulation of mast cells and of blood-borne basophils in response to certain allergens. This leads to increased IgE levels and the concomitant release of inflammatory mediators, such as histamine, and of chemotactic factors, such as cytokines, prostaglandins and leukotrienes, that result in a localized inflammatory reaction.

The immunostimulatory oligonucleotides may be administered as stand alone therapy without an additional anti-allergy/asthma medicament or therapy or in combination with such a therapy or medicament. Typical anti allergy/asthma medicaments and therapies include the use of intranasal vasoconstrictors, intranasal and systemic antihistamines, intranasal glucocorticoids, mast cell stabilizers, such as cromolyn compounds, and oral decongestants.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens*, *Cupressus arizonica* and *Cupressus macrocarpa*); *Juniperus* (e.g. *Juniperus sabinoides*, *Juniperus virginiana*, *Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-γ and GM-CSF). The redirection or rebalance of the immune response from a Th2 to a Th1 response is particularly useful for the treatment or prevention of asthma. For instance, an effective amount for treating asthma can be that amount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The CpG immunostimulatory oligonucleotides of the invention cause an increase in Th1 cytokines which helps to rebalance the immune system, preventing or reducing the adverse effects associated with a predominately Th2 immune response.

The CpG immunostimulatory oligonucleotides are also useful in some aspects of the invention as a vaccine for the treatment of a subject at risk of developing an infection with an infectious organism or a cancer in which a specific cancer antigen has been identified, in addition to allergy or asthma. The CpG immunostimulatory oligonucleotides can also be given without the antigen or allergen for protection against infection, allergy or cancer, and in this case repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing an allergy to asthma includes those subjects that have been identified as having an allergy or asthma but that don't have the active disease during the CpG immunostimulatory oligonucleotide treatment as well as subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a CpG immunostimulatory oligonucleotide, the subject may be able to kill the cancer cells as they develop. If a tumor begins to form in the subject, the subject will develop a specific immune response against the tumor antigen.

In addition to the use of the CpG immunostimulatory oligonucleotides for prophylactic treatment, the invention also encompasses the use of the CpG immunostimulatory oligonucleotides for the treatment of a subject having an infection, an allergy, asthma, or a cancer.

A subject having an infection is a subject that has been exposed to an infectious pathogen and has acute or chronic detectable levels of the pathogen in the body. The CpG immunostimulatory oligonucleotides can be used with or without an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors, infections, and allergy/asthma in non human subjects. Cancer is one of the leading causes of death in companion animals (i.e., cats and dogs).

As used herein, the term treat, treated, or treating when used with respect to an disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

In the instances when the CpG oligonucleotide is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the CpG immunostimulatory oligonucleotide. For instance, in a subject at risk of developing a cancer or an infectious disease or an allergic or asthmatic response, the subject may be administered the CpG immunostimulatory oligonucleotide on a regular basis when that risk is greatest, i.e., during allergy season or after exposure to a cancer causing agent. Additionally the CpG immunostimulatory oligonucleotide may be administered to travelers before they travel to foreign lands where they are at risk of exposure to infectious agents. Likewise the CpG immunostimulatory oligonucleotide may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

The term substantially purified as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are included within the invention.

The oligonucleotides of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleotide analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

CpG immunostimulatory oligonucleotides can be combined with other therapeutic agents such as adjuvants to enhance immune responses. The CpG immunostimulatory oligonucleotide and other therapeutic agent may be administered simultaneously or sequentially. When the other therapeutic agents are administered simultaneously they can be administered in the same or separate formulations, but are administered at the same time. The other therapeutic agents are administered sequentially with one another and with CpG immunostimulatory oligonucleotide, when the administration of the other therapeutic agents and the CpG immunostimulatory oligonucleotide is temporally separated. The separation in time between the administration of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the CpG immunostimulatory oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The CpG immunostimulatory oligonucleotides are also useful as mucosal adjuvants. It has previously been discovered that both systemic and mucosal immunity are induced by mucosal delivery of CpG oligonucleotides. Thus, the oligonucleotides may be administered in combination with other mucosal adjuvants.

Immune responses can also be induced or augmented by the co-administration or co-linear expression of cytokines (Bueler & Mulligan, 1996; Chow et al, 1997; Geissler et al., 1997; Iwasaki et al., 1997; Kim et al., 1997) or B-7 co-stimulatory molecules (Iwasaki et al., 1997; Tsuji et al., 1997) with the CpG immunostimulatory oligonucleotides. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

The oligonucleotides are also useful for improving survival, differentiation, activation and maturation of dendritic cells. The CpG immunostimulatory oligonucleotides have the unique capability to promote cell survival, differentiation, activation and maturation of dendritic cells.

CpG immunostimulatory oligonucleotides also increase natural killer cell lytic activity and antibody dependent cellular cytotoxicity (ADCC). ADCC can be performed using a CpG immunostimulatory oligonucleotide in combination with an antibody specific for a cellular target, such as a cancer cell. When the CpG immunostimulatory oligonucleotide is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available.

The CpG immunostimulatory oligonucleotides may also be administered in conjunction with an anti-cancer therapy. Anti-cancer therapies include cancer medicaments, radiation and surgical procedures. As used herein, a "cancer medicament" refers to a agent which is administered to a subject for the purpose of treating a cancer, As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

In one embodiment, the cancer medicament is a chemotherapeutic agent selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MM1270, BAY 12-9566, RAS farnesyl transferase inhibitor, farnesyl transferase inhibitor, MMP, MTA/LY231514, LY264618Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphthalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate. In an important embodiment, the cancer medicament is taxol. In another embodiment the cancer medicament is a combination of carboplatin and paclitaxel.

In another embodiment, the cancer medicament is an immunotherapeutic agent selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Additionally, the methods of the invention are intended to embrace the use of more than one cancer medicament along with the CpG immunostimulatory oligonucleotides. As an example, where appropriate, the CpG immunostimulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The use of CpG immunostimulatory oligonucleotides in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The oligonucleotides when used in combination with monoclonal antibodies serve to reduce the dose of the antibody required to achieve a biological result.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The CpG immunostimulatory oligonucleotides are also useful for treating and preventing autoimmune disease. Autoimmune disease is a class of diseases in which a subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the CpG immunostimulatory oligonucleotides be administered with self antigens, particularly those that are the targets of the autoimmune disorder.

In other instances, the CpG immunostimulatory oligonucleotides may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th21Th3 response.

The invention also includes a method for inducing antigen non-specific innate immune activation and broad spectrum resistance to infectious challenge using the CpG immunostimulatory oligonucleotides. The term antigen non-specific innate immune activation as used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The CpG immunostimulatory oligonucleotides may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell. Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

Delivery vehicles or delivery devices for delivering antigen and oligonuclotides to surfaces have been described. The CpG immunostimulatory oligonucleotide and/or the antigen and/or other therapeutics may be administered alone (e.g., in saline or buffer) or using any delivery vehicles known in the art.

The term effective amount of a CpG immunostimulatory oligonucleotide refers to the amount necessary or sufficient to realize a desired biologic effect. For example, an effective amount of a CpG immunostimulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular CpG immunostimulatory oligonucleotide being administered the size of the subject, or the severity of the disease or condition. One of ordinary skill in the art can empirically determine the effective amount of a particular CpG immunostimulatory oligonucleotide and/or antigen and/or other therapeutic agent without necessitating undue experimentation.

Subject doses of the compounds described herein for mucosal or local delivery typically range from about 0.1 μg to 10 mg per administration, which depending on the application could be given daily, weekly, or monthly and any other amount of time there between. More typically mucosal or local doses range from about 10 μg to 5 mg per administration, and most typically from about 100 μg to 1 mg, with 2-4 administrations being spaced days or weeks apart. More typically, immune stimulant doses range from 1 μg to 10 mg per administration, and most typically 10 μg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the CpG immunostimulatory oligonucleotides are administered in combination with other therapeutic agents or in specialized delivery vehicles typically range from about 0.1 μg to 10 mg per administration, which depending on the application could be given daily, weekly, or monthly and any other amount of time there between. More typically parenteral doses for these purposes range from about 10 μg to 5 mg per administration, and most typically from about 100 μg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG immunostimulatory oligonucleotide can be administered to a subject by any mode that delivers the oligonucleotide to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (i.e., CpG immunostimulatory oligonucleotides, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the oligonucleotide or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the oligonucleotide may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the oligonucleotide or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the oligonucleotides (or derivatives thereof). The oligonucleotide is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (al-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered-dose inhaler device will generally comprise a finely divided powder containing the oligonucleotide suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide and may also include a bulking agent, such as lactose, sorbitol, sucrose, or mannitol in amounts which facilitate dispersal of the powder from the device, e.g., 50 to 90% by weight of the formulation. The oligonucleotide should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed, The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The CpG immunostimulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG immunostimulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Oligodeoxynucleotides (ODNs)

The following ODN are used in the examples.

| SEQ ID-NO. | Sequence |
|---|---|
| 1 | T*C_G*T*C_G*A*C_G*T*T*C_G*G*C*G*C_G*C*G*C*C*G |
| 2 | T*C_G*T*C_G*T*C_G*T*T*C_G*G*C*G*C_G*C*G*C*C*G |
| 3 | T*C_G*T*C_G*T*T*C_G*G*C*G*C*G*C*C*G |
| 4 | T*C_G*T*C_G*A*C_G*A*T*C_G*G*C*G*C_G*C*G*C*C*G |
| 5 | T*T*C_G*T*C_G*T*T*T*T_G*T*C_G*T*T |
| 6 | T*T*T*C_G*T*C_G*T*T*T*C_G*T*C_G*T*T |
| 7 | T*C_G*T*C_G*T*T*T*T*G*A*C_G*T*T*T*T*G*T*C_G*T*T |
| 8 | TCG TCG TTT TGT CGT TTT GTC GTT (all bonds *) |
| 9 | T*C_G*C_G*A*C_G*T*T*C_G*G*C*G*C_G*C*G*C*C*G |
| 10 | TCG TCG TTT TGA CGT TTT GTC GTT (all bonds *) |
| 14 | TCCAGGACTTCTCTCAGGTT (all bonds *) |
| 15 | C-G*T*C-G*T*C-G*T*T*C-G*G*C*G*C-G*C*G*C*C*G |
| 16 | G*T*C-G*T*C-G*T*T*C-G*G*C*G*C-G*C*G*C*C*G |
| 17 | T*C-G*T*C-G*T*T*C-G*G*C*G*C-G*C*G*C*C*G |
| 18 | C-G*T*C-G*T*T*C-G*G*C*G*C-G*C*G*C*C*G |
| 19 | G*T*C-G*T*T*C-G*G*C*G*C-G*C*G*C*C*G |
| 20 | T*C-G*T*T*C-G*G*C*G*C-G*C*G*C*C*G |
| 21 | T*C-G*T*C-G*T*C-G*T*T*C-G*G*C*G*C-G*C*G*C*C*C |
| 22 | T*C-G*T*C-G*T*C-G*T*T*C-G*G*C*G*C |
| 23 | T*C-G*T*C-G*T*C-G*T*T*C-G*G*C*G*C-G*C*G*C |

Materials and Methods:

Oligodeoxynucleotides (ODNs)

ODNs were purchased from Biospring (Frankfurt, Germany) or Sigma-Ark (Darmstadt, Germany), and were controlled for identity and purity by Coley Pharmaceutical GmbH (Langenfeld, Germany). ODNs were diluted in phosphate-buffered saline (Sigma, Germany), and stored at −20° C. All dilutions were carried out using pyrogen-free reagents. SEQ ID NO. 15-23 ODNs were synthesized by Trilink Biotechnologies.

Cell Purification

Peripheral blood buffy coat preparations from healthy male and female human donors were obtained from the Blood Bank of the University of Düsseldorf (Germany) and from these, PBMC were purified by centrifugation over Ficoll-Hypaque (Sigma). The purified PBMC were either used freshly (for most assays) or were suspended in freezing medium and stored at −70° C. When required, aliquots of these cells were thawed, washed and resuspended in RPMI 1640 culture medium (BioWhittaker, Belgium) supplemented with 5% (v/v) heat inactivated human AB serum (BioWhittaker, Belgium) or 10% (v/v) heat inactivated FCS, 2 mM L-glutamine (BioWhittaker), 100 U/ml penicillin and 100 µg/ml streptomycin (Invitrogen (Karlsruhe, Germany)).

Cytokine Detection

Thawed or fresh PBMC were seeded on 48 well flat-bottom plates, or 96 well round-bottom plates, and incubated with ODN in the concentrations as indicated in a humidified incubator at 37° C. Culture supernatants were collected and if not used immediately, were frozen at −20° C. until required. Amounts of cytokines in the supernatants were assessed using commercially available ELISA Kits (Diaclone, USA) or in-house ELISAs developed using commercially available antibodies (from Becton Dickinson/Pharmingen or PBL).

Studies for Example 13 were conducted as follows:

Spleens were removed from 6 mice (male, BALB/c). The splenocytes from each spleen were separated by pushing gently through a cell sieve (70 µm pore size), and were then pooled. Splenocytes were added to wells of culture plates. $1 \times 10^7$ cells in a volume of 900 µl medium were added to each well. Medium was RPMI 1640 containing 10% fetal bovine serum. 100 µl aliquots of CpG ODN solutions in medium were added to each well to give final concentrations in the wells of 0.01-10 µg/ml. After incubation for 36 hours (37 C, 5% $CO_2$ incubator), culture supernatants were collected and assayed for cytokine concentrations using either the Luminex multiplex assay (IFNγ, IP-10, IL-10, IL-6, TNFα) or ELISA (IFNα).

Induction of Antigen-Induced Increase in Nasal Resistance in Guinea Pigs

Guinea pigs (male, Hartley) were sensitized with antigen (ovalbumin, 5 mg both intraperitoneal and subcutaneous) on study day 0. A boost sensitization (5 mg, intraperitoneal) was given on study day 4. Guinea pigs were antigen challenged by exposure to intranasally-administered antigen twice each week for two consecutive weeks. The first challenge was on study day 14. SEQ ID NO:7 (lot number AQE-03J-001-M, 0.03-1 mg/kg in 150 µl/kg saline) was administered intranasally once each week, two days before the first antigen challenge of the week. With the exception of the final challenge on study day 24, antigen challenge was with ovalbumin (1.5 mg/kg in 150 µl/kg saline). Animals were pretreated with mepyramine (10 mg/kg, intraperitoneal) 30 minutes before challenge to protect against histamine-induced anaphylaxis. On study day 24, guinea pigs were anesthetized to allow measurement of nasal resistance using a Buxco respiratory mechanics system and software. The final antigen challenge was then made with ovalbumin (2.5 mg in 250 µl saline) delivered into the nasopharynx. Animals were pretreated with mepyramine (3 mg/kg, intraperitoneal) 30 minutes before challenge. Nasal resistance was measured for 40 minutes after challenge.

Induction of Antigen-Induced Increase in Nasal Resistance in Mice

Mice (male BALB/c) were sensitized on study days 0 and 7 with antigen (ovalbumin, 100 µg, i.p.) with aluminum hydroxide adjuvant (Pierce Alum i.p.). Mice were antigen challenged daily by exposure to intranasally-administered antigen (1 mg in 10 µl saline). The first challenge was on study day 14. SEQ ID NO:7 was administered intranasally twice. The first dose was given 2 days before the first antigen challenge. The second dose was given 7 days later. Alternatively, budesonide (an anti-inflammatory, synthetic corticosteroid) was administered intranasally daily. The first dose was given 2 days before the first antigen challenge. On each day, the budesonide dose was administered intranasally 4 hours before intranasal antigen challenge. Endpoints were measured on study day 26 (i.e. 7 days after the second dose of SEQ ID NO: 7. Nasal tissues were taken for histopathological assessment of inflammation. Separate mice received a final antigen challenge and incidences of sneezing and nasal rubbing were counted for a 10 minute period after challenge.

Statistical Analysis

The Mann-Whitney test was used for comparison of data sets where the populations being compared were not normal. The Dunnitt multiple comparisons test was used for comparison of data sets to a single control.

Cytokine Induction in the Mouse In Vivo

Mice (male, BALB/c) were dosed with CpG ODNs (0.1 and 1 mg/kg) or control vehicle (saline, 25 µl) by intranasal instillation. Bronchoalveolar lavage fluid and serum (separated from blood obtained by cardiac puncture) were collected 8 hours and 15 hours after dosing. Cell numbers in bronchoalveolar lavage fluid were counted with an Advia automated cell counter. Concentrations of cytokines and chemokines in bronchoalveolar lavage fluid and serum were assayed using either ELISA (IFNα, IL-12p40) or the Luminex cytokine multiplex system (IFNγ, IP-10, IL-1α, IL-1β, IL-2, IL-4, IL-5, IL-6, IL-7, IL-9, IL-10, IL-13, IL-15, IL-17, GM-CSF, RANTES, TNFα). Minimum detectable concentrations were different for each analyte, but were in the range 0.3-12 pg/ml.

Influenza Virus Induction of Inflammation in Mouse Airways.

Influenza virus (influenza type A, subtype H1N1, mouse adapted strain PR8) was a gift from David Woodhouse, Trudeau Institute, Saranac Lake, N.Y. As a preliminary study to titrate influenza dose and determine time-course of infection, BALB/c mice (female) were infected with influenza virus by intranasal instillation on study day 0. Mice received 50, 200 or 500 egg-infective doses $(ED)_{50}$ of virus in 40 µl saline. Airway inflammation was assessed 1, 3, 6, 9 and 14 days after infection.

Intranasal Administration of CpG ODN and Measurement of Airway Inflammation

Mice received a CpG ODN (0.03, 0.3 or 3 mg/kg) by intranasal instillation in 25 µl saline. Each mouse was dosed twice, 6 days and 2 days before infection with influenza virus (200 $EID_{50}$, intranasal). This virus dose was selected from the preliminary study. Airway inflammation and virus load in the lung were assessed 6 days after virus infection. This time point was selected from the preliminary study. Cells in airways were recovered by bronchoalveolar lavage. Total leukocyte counts were made with an Advia automated cell counter (Adiva, Bayer Diagnostics, Zurich, Switzerland). Differential cell counts were made by light microscopy of cytocentrifuge preparations stained with Wright-Giemza stain. Lungs were removed and homogenized with 300 µl sterile PBS. supernatant was collected and virus load was assayed using an enzyme immunoassay kit (Takara Biomedical, Shiga, Japan) used to manufacturer's instructions. This assay utilizes a monoclonal antibody against influenza A virus nuclear protein as solid phase, and a polyclonal anti-influenza virus detection antibody.

Example 1

Effects on IFN-α Secretion by Human PBMC Treated with CpG ODN

Methods: Human peripheral blood mononuclear cells from either three (SEQ ID NO:4, SEQ ID NO:5, SEQ ID NO:6) or seven (SEQ ID NO:1, SEQ ID NO:2, SEQ ID NO:3) donors were incubated with CpG ODN for 48 hours at concentrations indicated. Interferon-alpha secretion by human PBMC was measured.

Results: FIG. 1 demonstrates increased production of IFN-α upon incubation with CpG ODN. Data represent the mean +/−SEM. Note that the absolute levels in pg/ml can not be compared directly, as PBMC from different donors were used and results from each donor are variable.

Example 2

Stimulation of TLR9-Transfected Cells In Vitro

Methods: HEK 293 cells transfected with human TLR9 were incubated with SEQ ID NO:1, SEQ ID NO:2, SEQ ID NO:3, SEQ ID NO:4, SEQ ID NO:5, or SEQ ID NO:6 for 16 hours. The signal was determined by a luciferase readout.

Results: The results are shown in Table 1. The EC50 was calculated using Sigma Plot (SigmaPlot 2002 for Windows version 8.0). The maximal stimulation index (max SI) was calculated as the quotient between the highest value of all concentrations tested for any ODN and the medium control.

TABLE 1

| ODN | EC50 | max SI |
| --- | --- | --- |
| SEQ ID NO: 1 | 2320 | 22 |
| SEQ ID NO: 2 | 4730 | 20 |
| SEQ ID NO: 3 | 2400 | 16 |
| SEQ ID NO: 4 | 3200 | 14 |
| SEQ ID NO: 5 | 4290 | 13 |
| SEQ ID NO: 6 | 4580 | 11 |

Example 3

Effects of the CpG Oligodeoxynucleotide SEQ ID NO:7 Against Antigen-Induced Increase in Nasal Resistance in Guinea Pigs Methods: To investigate the effects of the CpG oligodeoxynucleotide SEQ ID NO:7 against antigen induced increases in nasal resistance in the guinea pigs guinea pigs were sensitized with antigen, then antigen-challenged nasally. Nasal resistance was measured for 40 minutes after challenge.

TABLE 2

| Summary of study protocol | | | | | | |
| --- | --- | --- | --- | --- | --- | --- |
| Antigen sensitize | Dose with SEQ ID NO: 7 | Antigen challenge | Dose with SEQ ID NO: 7 | Antigen challenge | | |
| Day: 0 | 4 | 12 | 14 | 17 | 19 | 21 24 |
| | | | | | | Measure antigen-induced increase in nasal resistance |

Figure 2A:
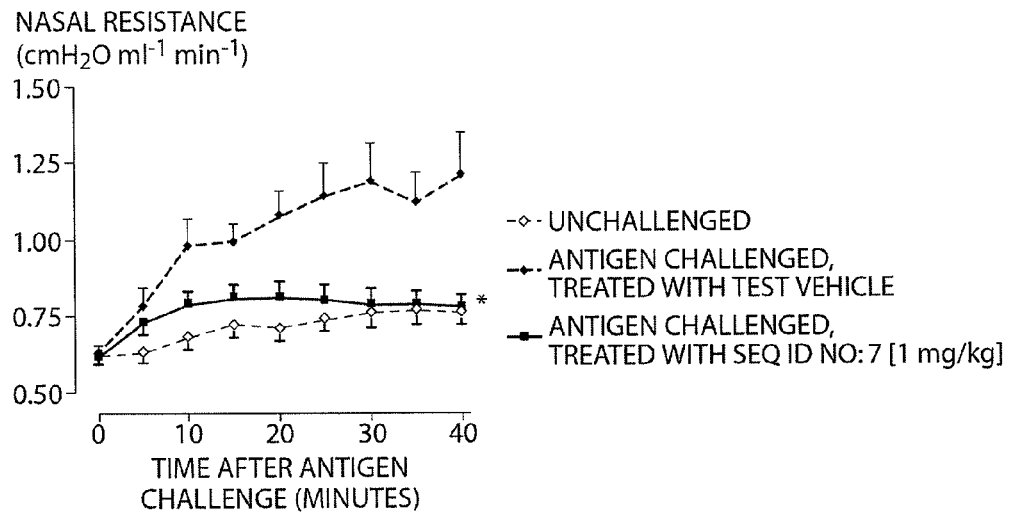
FIG. 2 is a series of graphs depicting the effects of the CpG oligodeoxynucleotide SEQ ID NO. 7 against antigen-induced increase in nasal resistance in guinea pigs administered in a dose of (A) 1 mg/kg and (B) (0.03-0.3 mg/kg). Results are mean±s.e.m. ((A)=n=5-8; (B)=n=14-15). * P<0.05 compared with antigen-challenged group treated with test vehicle (t test).
Figure 2B:
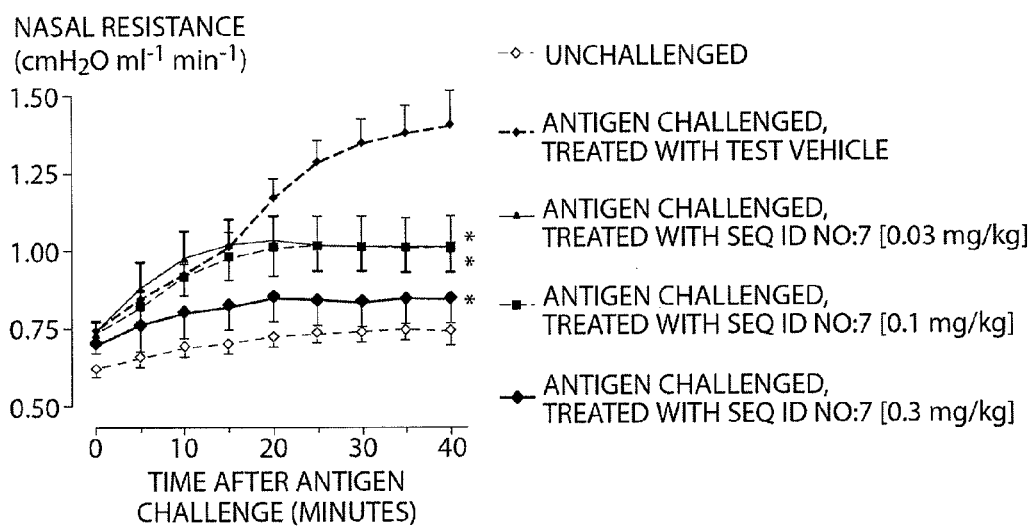

Results: FIG. 2 demonstrates that antigen challenge caused a progressive increase in nasal resistance over 40 minutes that was significantly suppressed in guinea pigs that had been treated with SEQ ID NO:7 (0.03-1 mg/kg).

Example 4

Effects of CpG Oligonucleotide SEQ ID NO:7 in a Mouse Model of Allergic Rhinitis Methods: BALB/c mice were used to study the effects of SEQ ID NO:7 on symptoms of allergic rhinitis. After sensitization and antigen challenge, nasal tissues were taken for histopathological assessment of inflammation. Separate mice received a final antigen challenge and incidences of sneezing and nasal rubbing were counted for a 10 minute period after challenge.

TABLE 3

Summary of study protocol: oligonucleotide-treated mice

| | Sensitize | SEQ ID NO: 7 or SEQ ID NO: 8 | SEQ ID NO: 7 or SEQ ID NO: 8 Daily antigen challenges | | | | | | | | | | | | |
|---|---|---|---|---|---|---|---|---|---|---|---|---|---|---|---|
| Day: | 0 | 7 | 12 | 13 | 14 | 15 | 16 | 17 | 18 | 19 | 20 | 21 | 22 | 23 | 24 | 25 | 26 |

Endpoints

TABLE 4

Summary of study protocol: budesonide-treated mice

| | Sensitize | Daily doses with budesonide | | | | | | | | | | | | | |
|---|---|---|---|---|---|---|---|---|---|---|---|---|---|---|---|
| | | | | Daily antigen challenges | | | | | | | | | | | |
| Day: | 0 | 7 | 12 | 13 | 14 | 15 | 16 | 17 | 18 | 19 | 20 | 21 | 22 | 23 | 24 | 25 | 26 |

Endpoints

Figure 3A:
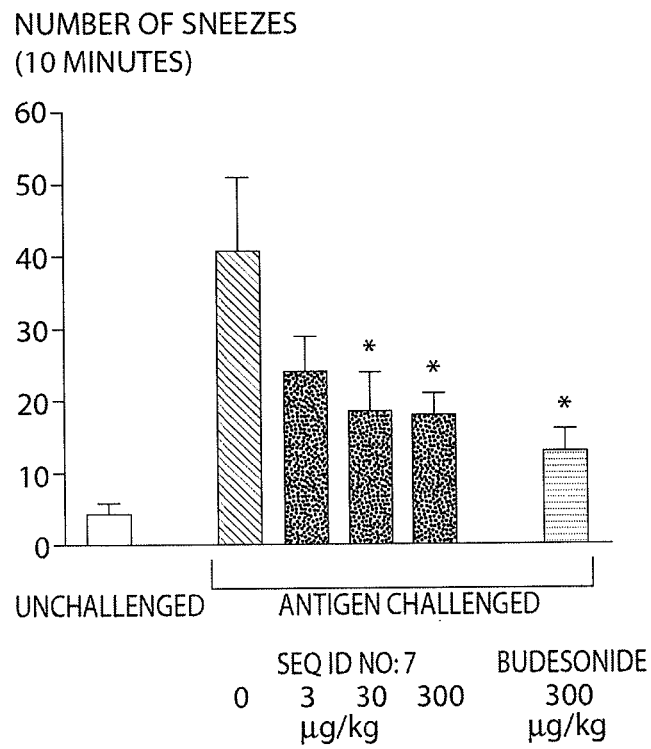
FIG. 3 is a series of graphs depicting the effects of the CpG oligodeoxynucleotide SEQ ID NO. 7 on antigen-induced sneezing (3A) and nasal rubbing (3B) in a mouse model of allergic rhinitis. Results are mean±s.e.m. (n=10). * P<0.05 compared with vehicle-treated group (Mann-Whitney test).
Figure 3B:
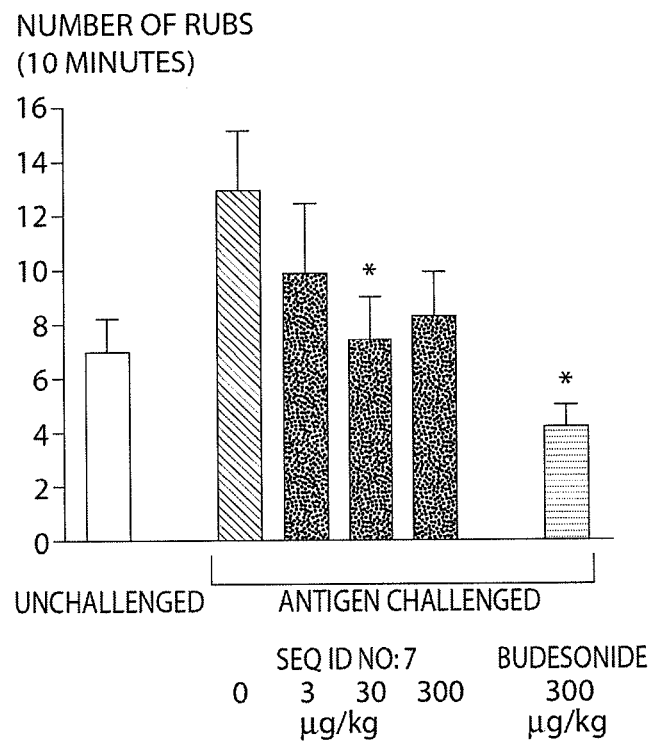

Results: Antigen challenge caused sneezing and nasal rubbing. As demonstrated in FIG. 3 the incidences of both were suppressed in mice treated with SEQ ID NO:7.

Example 5

Influenza Virus-Induced Airway Inflammation in Mouse Lung: Effects of Class C CpG Oligodeoxynucleotides Introduction: CpG oligodeoxynucleotides (ODNs) induce immune-modifying cytokines that should provide anti-asthma effects. Class C CpG ODNs induce higher titers of IFNα than previous class B ODNs. Class C CpG ODNs may offer the additional benefit of suppressing virus-induced exacerbations of asthma. This study investigated the ability of three class C CpG ODNs to suppress virus (influenza) load in mouse lungs and virus-induced airways inflammation.

Methods: Influenza virus was used to induce airway inflammation in BALB/c mice. CpG ODNs were administered intranasally and the protective effect was measured.

Figure 4:
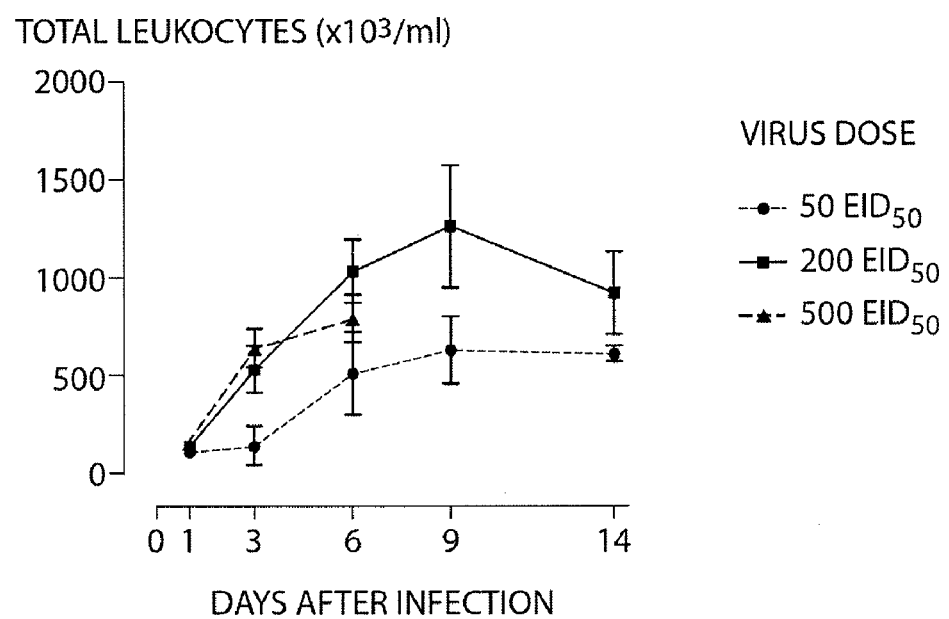
FIG. 4 is a graph depicting a titration of influenza virus and determination of time course of infection. Cell numbers in bronchoalveolar lavage fluid. Results are mean±s.e.m. (n=5). Mice infected with 500 $EID_{50}$ were sacrificed after 6 days because of weight loss.

Results: FIG. 4 shows that in a preliminary study to titrate influenza dose and determine time-course of infection, influenza virus caused an accumulation of leukocytes in the airways. Peak inflammation was achieved after 6-9 days. Mice infected with 500 EID50 of virus showed marked weight loss after 6 days and were sacrificed.

Figure 5:
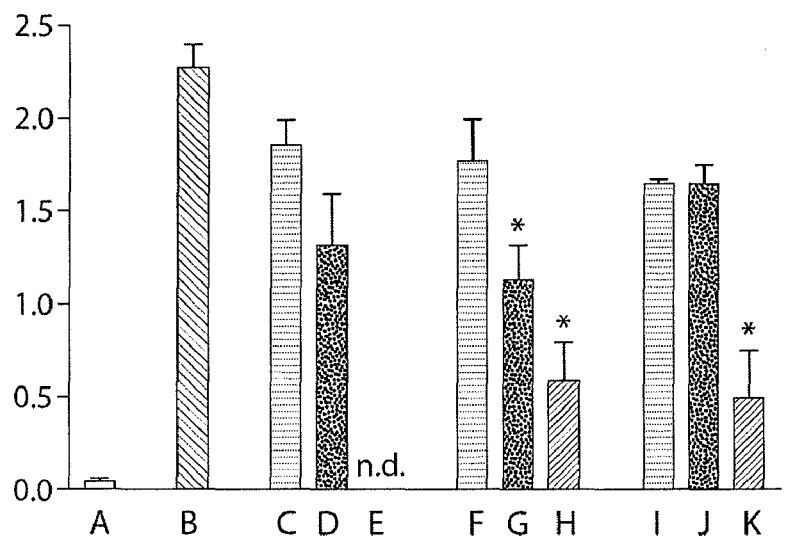
FIG. 5 is a graph depicting the protective effects of CpG ODNs on virus load in the lung. Virus load assayed by enzyme immunoassay. Results are mean±s.e.m. (n=5-10). * P<0.05 compared with group B (Kruskal-Wallis test, Dunn's post-test). n.d.=no data.
Figure 6A:
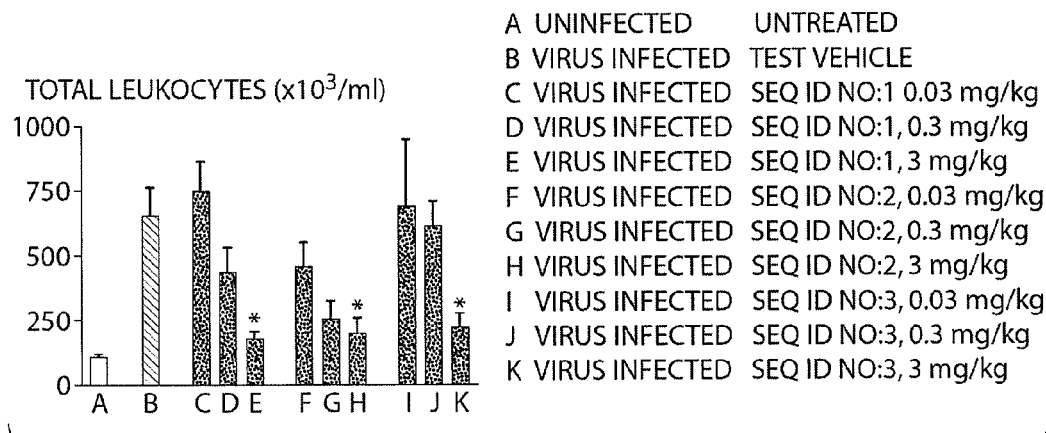
FIG. 6 is a series of graphs depicting the protective effects of CpG ODNs on virus-induced airways inflammation measuring total leukocytes (6A), total neutrophils (6B) and total mononuclear cells (6C). Cell numbers in bronchoalveolar lavage fluid. Results are mean±s.e.m. (n=10). * P<0.05 compared with group B (Kruskal-Wallis test, Dunn's post-test).
Figure 6B:
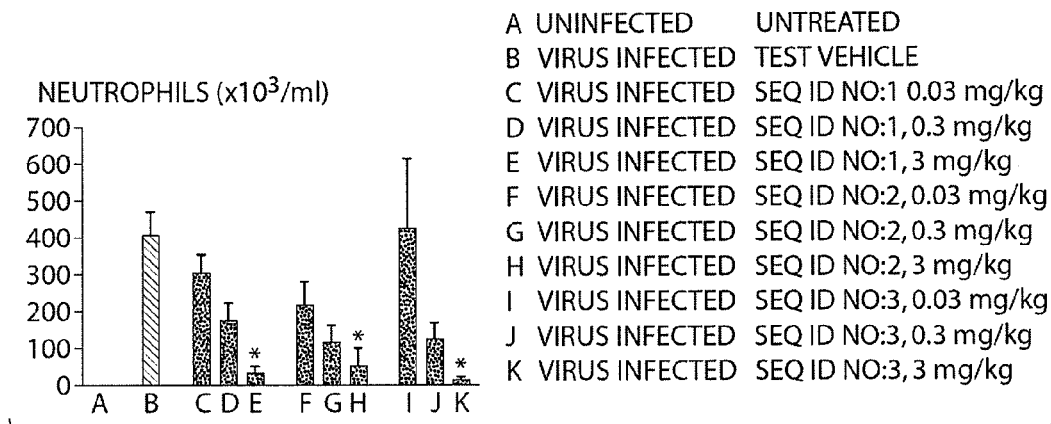
Figure 6C:
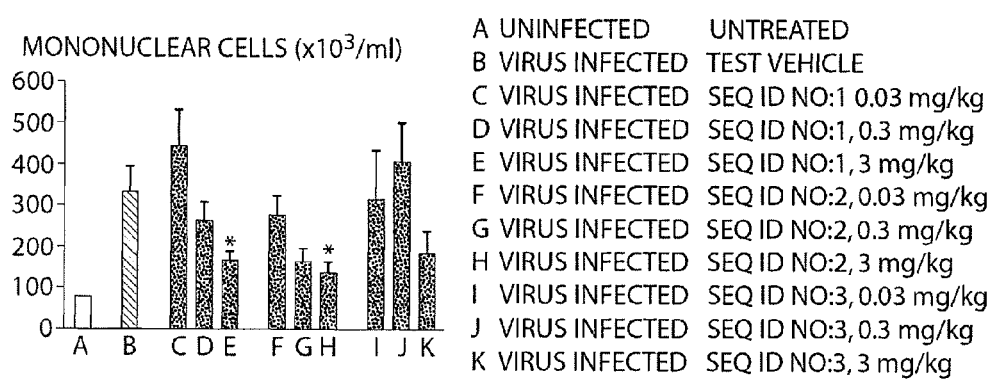

FIG. 5 demonstrates the protective effects of CpG ODNs on virus load and virus-induced airways inflammation. Pretreatment with CpG ODNs before infection with influenza virus (200 EID50) reduced virus load in the lung as assayed 6 days after infection. FIG. 6 demonstrates that infection with influenza virus caused an accumulation of leukocytes in the airways 6 days later. These were predominantly neutrophils and mononuclear cells (monocytes, macrophages and lymphocytes). There wee very few eosinophils. Cell accumulation was significantly suppressed in mice pretreated with any of the CpG ODNs.

Example 6

Effects of class C CpG Oligodeoxynucleotides Against Antigen-Induced Airways Inflammation in the Mouse The activity of three class C CpG oligodeoxynucleotides (ODNs) was compared. The class B CpG ODN SEQ ID NO:7 was included in the study for comparison.

Methods: Mice (male BALB/c) were sensitized on study days 0 and 7 with antigen (cockroach, 10 μg, intraperitoneal) with aluminum hydroxide adjuvant (Pierce Alum, intraperitoneal). Mice were antigen challenged by exposure to intranasally-administered antigen (10 μg in 40 μl saline), twice each week for two consecutive weeks. The first challenge was on study day 21. CpG ODNs (1, 10 and 100 μg/kg) were administered intranasally once each week, two days before the first antigen challenge of the week.

Airways inflammation was assessed 48 hours after the last antigen challenge. Cells in airways were recovered by bronchoalveolar lavage. Differential cell counts were made by an Advia automated cell counter. Numbers of T cells (Total CD3+ cells, and CD3+ CD4+ cells) were counted by flow cytometry.

TABLE 5

Summary of study protocol

| | Antigen sensitize | Dose with CpG ODN | Antigen challenge | Dose with CpG ODN | Antigen challenge | | | |
|---|---|---|---|---|---|---|---|---|
| Day: | 0 | 7 | 19 | 21 | 24 | 26 | 28 | 31 | 33 |

Assess airways inflammation

TABLE 6

CpG ODNs tested

| SEQ ID NO: 7 | Semi-soft class B | Lot A25-0313-L1 |
| SEQ ID NO: 1 | Semi-soft class C | Lot C44-1209-M1B |
| SEQ ID NO: 2 | Semi-soft class C | Lot C44-1209-M2D |
| SEQ ID NO: 3 | Semi-soft class C | Lot C44-1209-M4B |

Figure 7A:
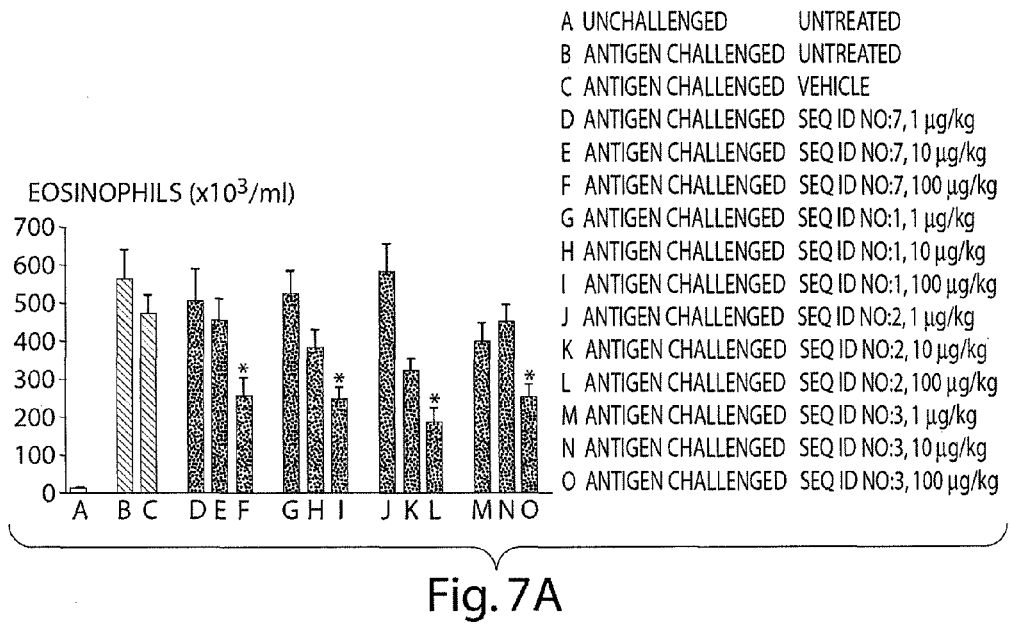
FIG. 7 is a series of graphs depicting the protective effects of CpG ODNs on cell numbers in antigen-induced airways inflammation in eosinophils (7A) and neutrophils (7B). Results are mean±s.e.m. (n=10-14). * P<0.05 compared with antigen challenged, vehicle-treated group (Kruskal-Wallis multiple comparison test, Dunn's post test).
Figure 7B:
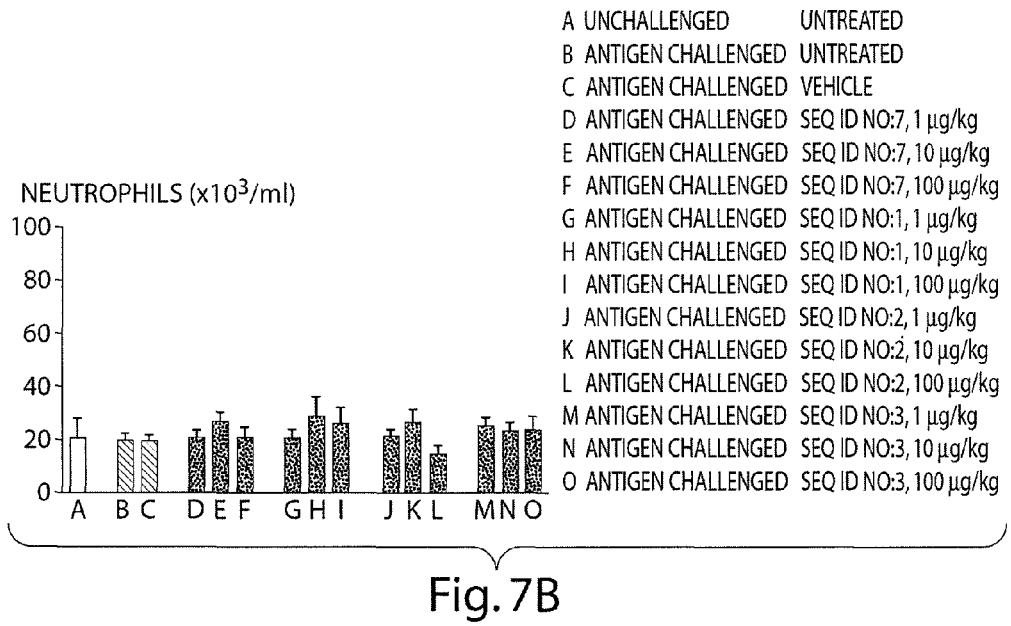
Figure 8A:
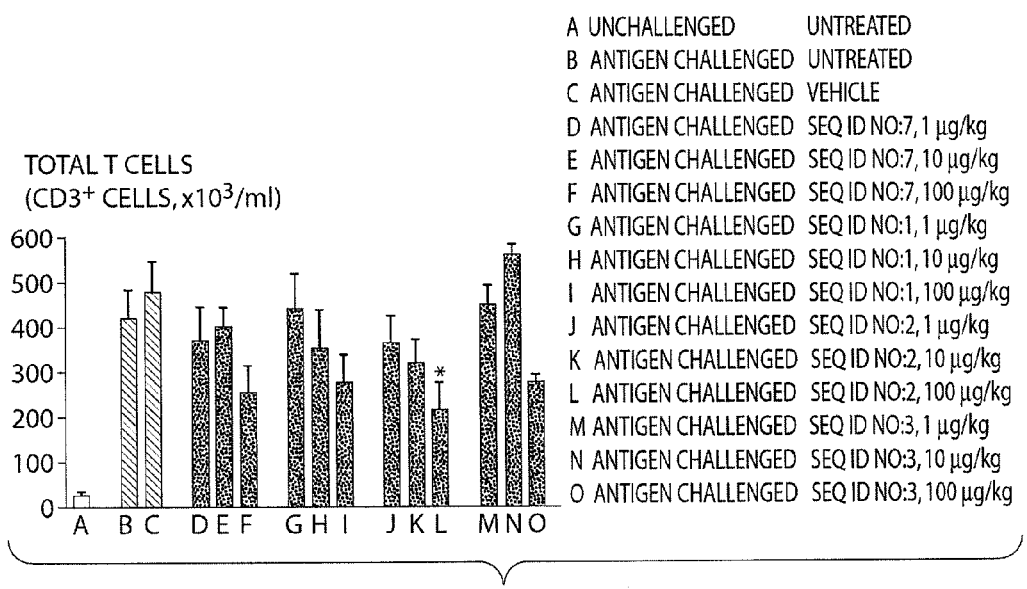
FIG. 8 is a series of graphs depicting the protective effects of CpG ODNs on $CD3^+$ (8A) and $CD3^+CD4^+$ (8B) cell numbers in antigen-induced airways inflammation. Results are mean±s.e.m. (n=8). * P<0.05 compared with antigen challenged, vehicle-treated group (Kruskal-Wallis multiple comparison test, Dunn's post test).
Figure 8B:
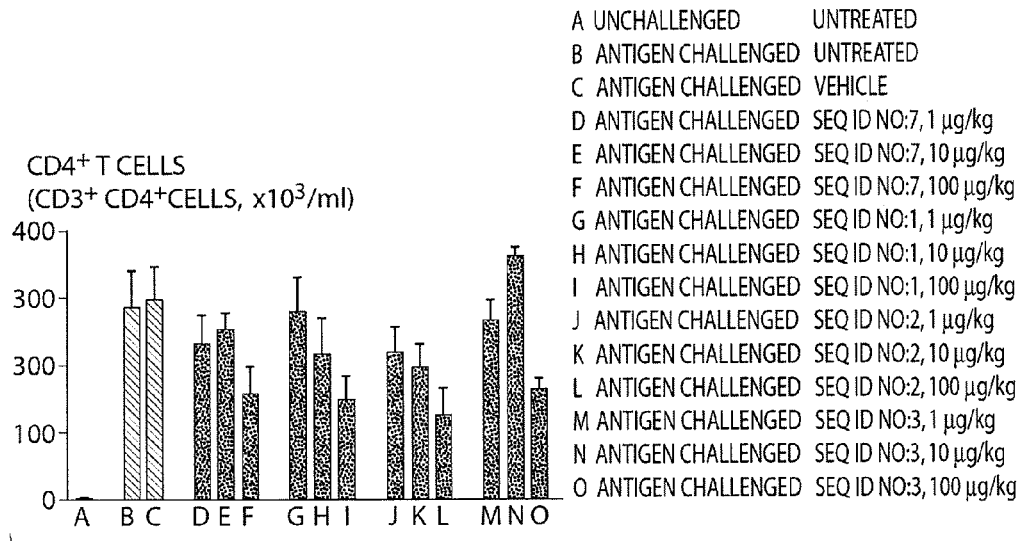
Figure 9A:
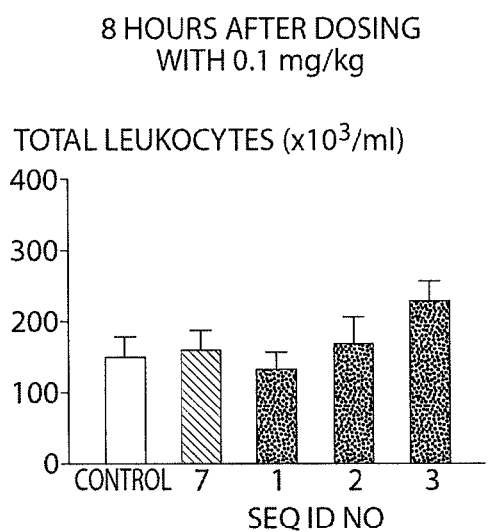
FIG. 9 is a series of graphs depicting cell numbers in bronchoalveolar lavage fluid 8 hours after dosing with 0.1 mg/kg ODN (9A); 15 hours after dosing with 0.1 mg/kg ODN (9B); 8 hours after dosing with 1 mg/kg ODN (9C); and 15 hours after dosing with 1 mg/kg ODN (9D). Results are mean±s.e.m (n=10)
Figure 9B:
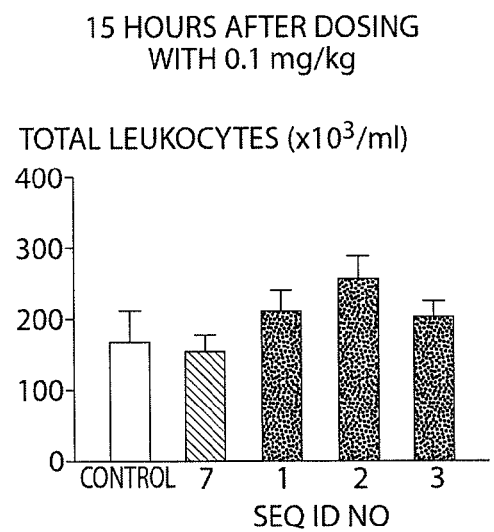
Figure 9C:
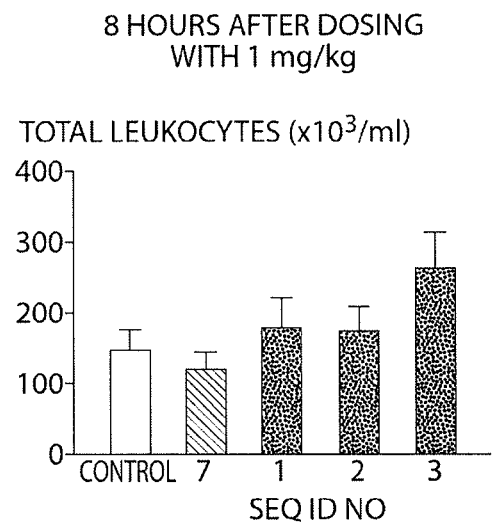
Figure 9D:
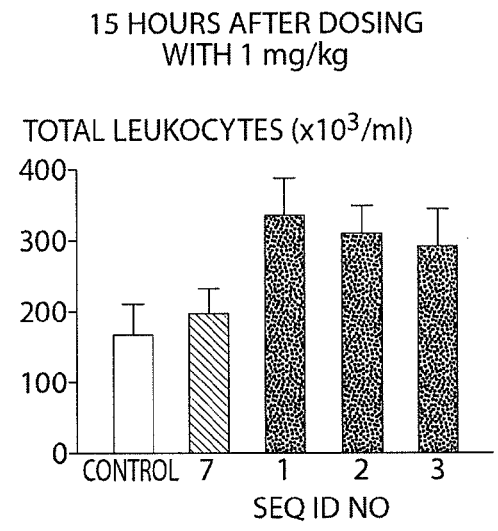
Figure 10A:
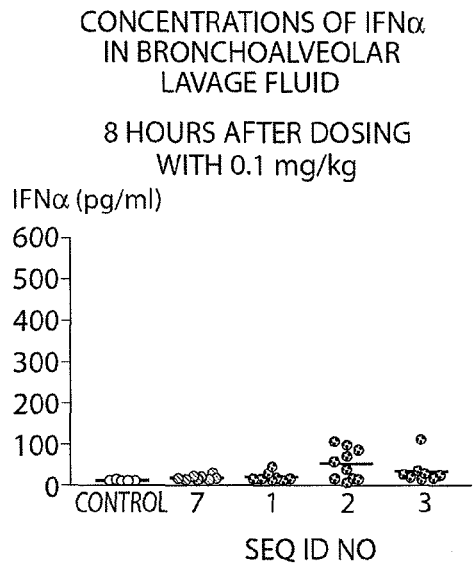
FIG. 10 is a series of graphs depicting concentrations of IFN alpha in bronchoalveolar lavage fluid 8 hours after dosing with 0.1 mg/kg ODN (10A); 15 hours after dosing with 0.1 mg/kg ODN (10B); 8 hours after dosing with 1 mg/kg ODN (10C); and 15 hours after dosing with 1 mg/kg ODN (10D).
Figure 10B:
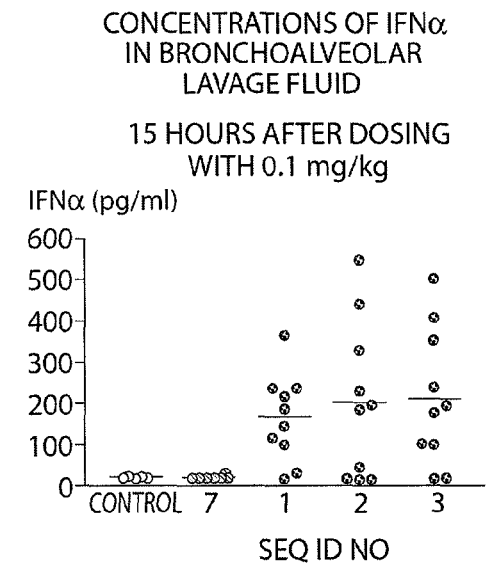
Figure 10C:
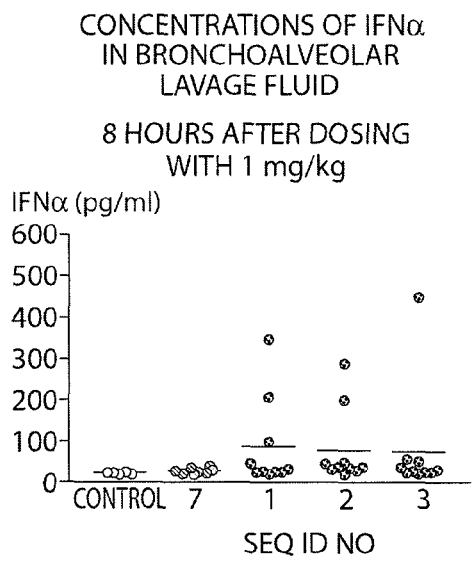
Figure 10D:
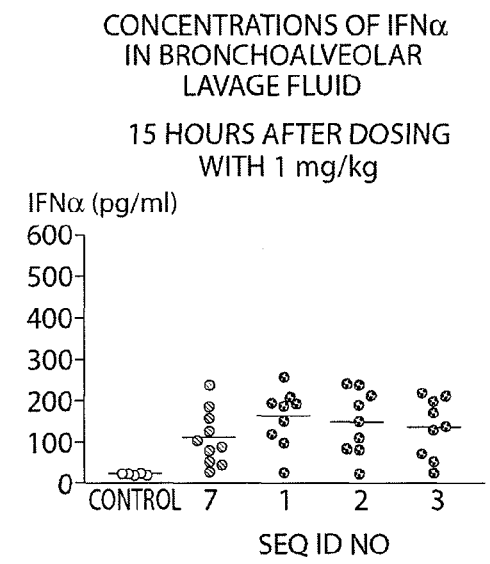
Figure 11A:
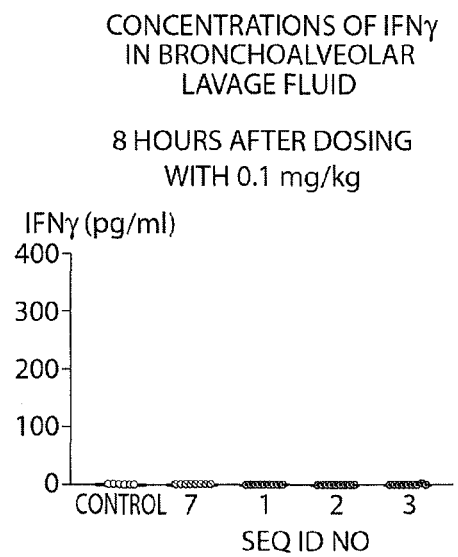
FIG. 11 is a series of graphs depicting concentrations of IFN gamma in bronchoalveolar lavage fluid 8 hours after dosing with 0.1 mg/kg ODN (11A); 15 hours after dosing with 0.1 mg/kg ODN (11B); 8 hours after dosing with 1 mg/kg ODN (11C); and 15 hours after dosing with 1 mg/kg ODN (11D).
Figure 11B:
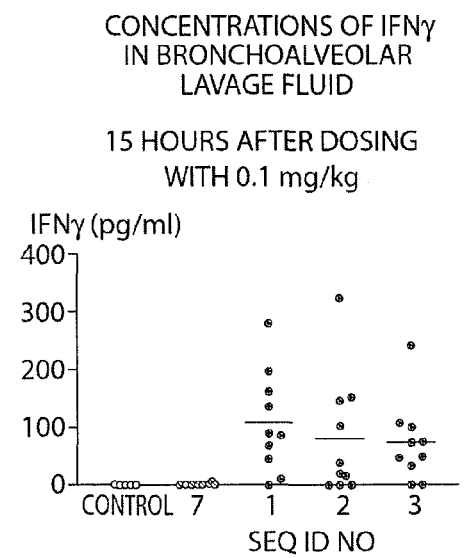
Figure 11C:
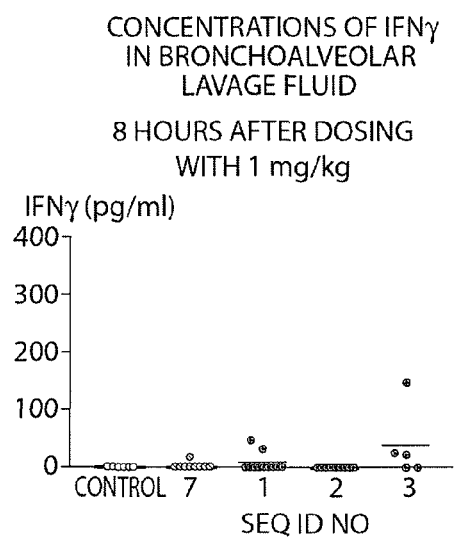
Figure 11D:
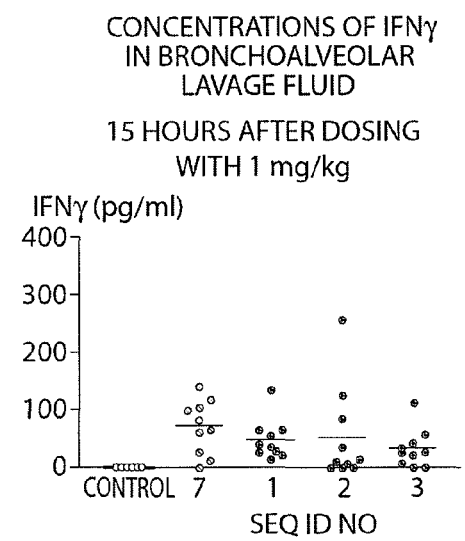
Figure 12A:
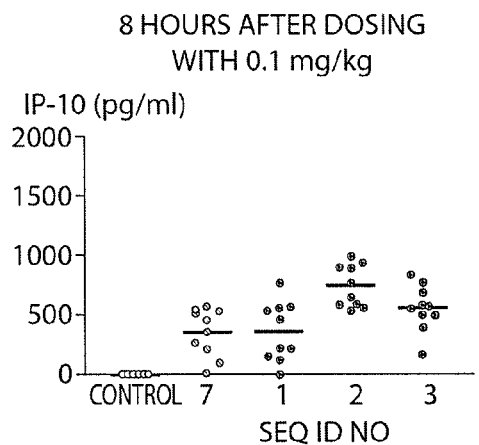
FIG. 12 is a series of graphs depicting concentrations of IP-10 in bronchoalveolar lavage fluid 8 hours after dosing with 0.1 mg/kg ODN (12A); 15 hours after dosing with 0.1 mg/kg ODN (12B); 8 hours after dosing with 1 mg/kg ODN (12C); and 15 hours after dosing with 1 mg/kg ODN (12D).
Figure 12B:
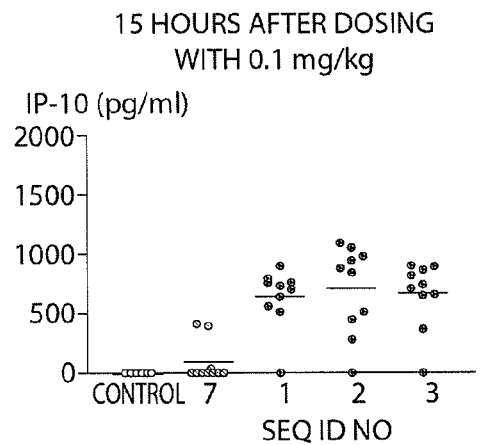
Figure 12C:
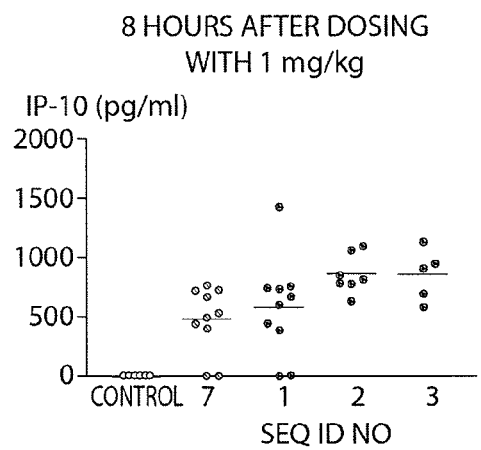
Figure 12D:
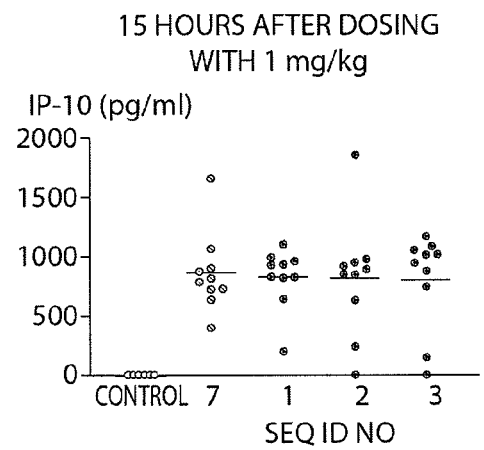
Figure 13A:
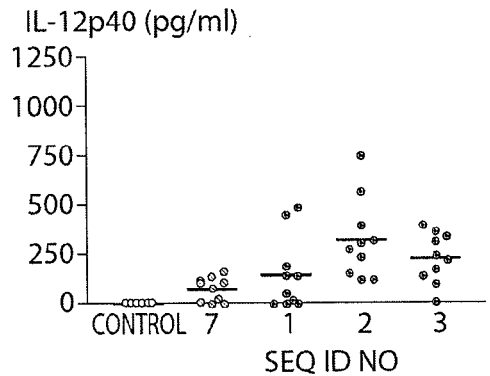
FIG. 13 is a series of graphs depicting concentrations of IL-12p40 in bronchoalveolar lavage fluid 8 hours after dosing with 0.1 mg/kg ODN (13A); 15 hours after dosing with 0.1 mg/kg ODN (13B); 8 hours after dosing with 1 mg/kg ODN (13C); and 15 hours after dosing with 1 mg/kg ODN (13D).
Figure 13B:
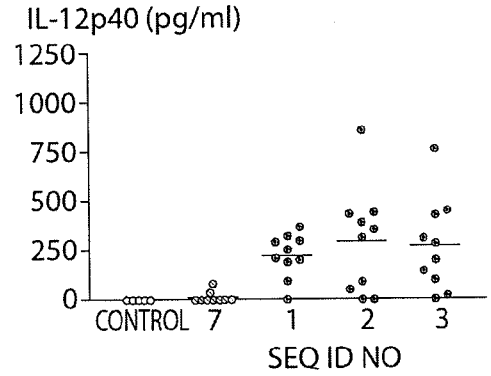
Figure 13C:
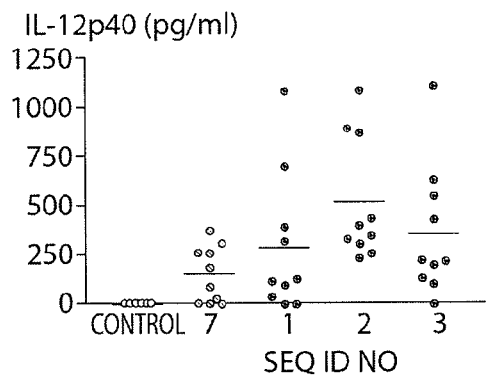
Figure 13C:
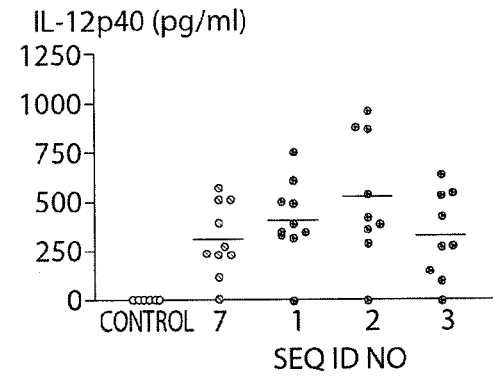
Figure 14A:
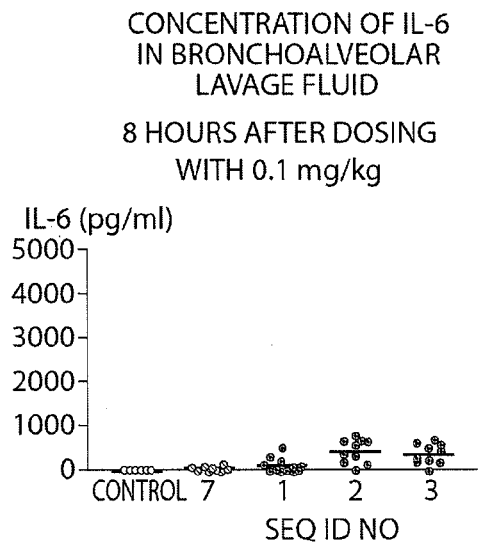
FIG. 14 is a series of graphs depicting concentrations of IL-6 in bronchoalveolar lavage fluid 8 hours after dosing with 0.1 mg/kg ODN (14A); 15 hours after dosing with 0.1 mg/kg ODN (14B); 8 hours after dosing with 1 mg/kg ODN (14C); and 15 hours after dosing with 1 mg/kg ODN (14D).
Figure 14B:
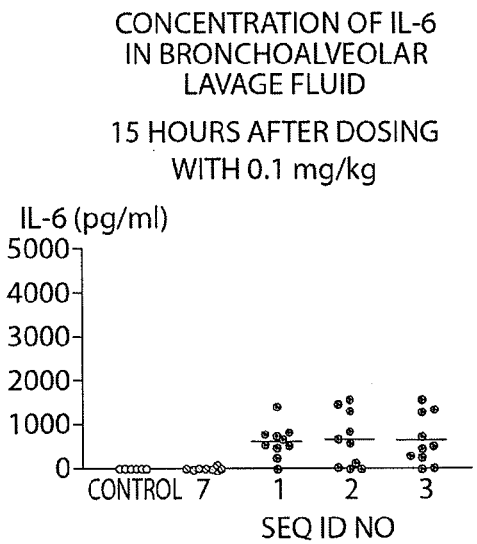
Figure 14C:
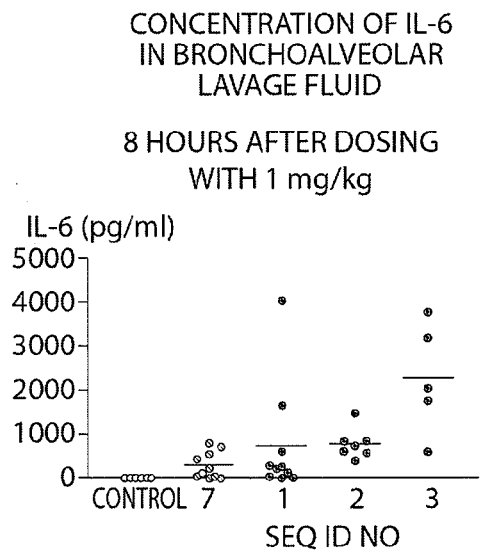
Figure 14D:
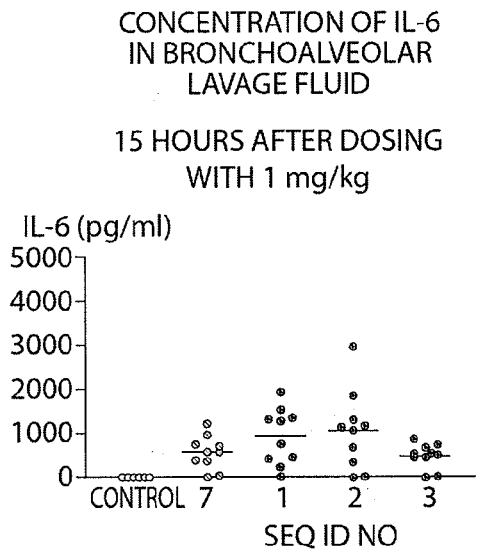
Figure 15A:
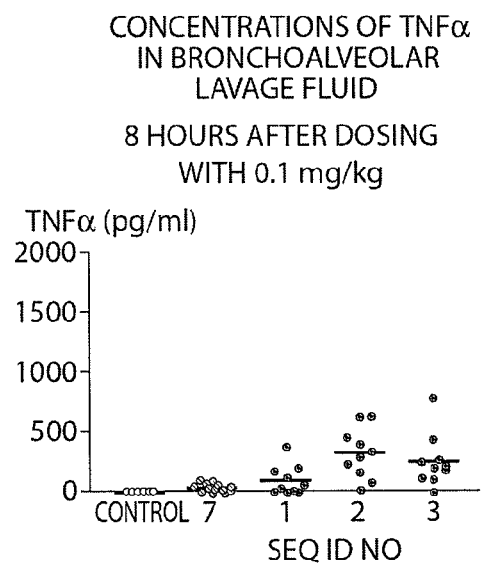
FIG. 15 is a series of graphs depicting concentrations of TNFalpha in bronchoalveolar lavage fluid 8 hours after dosing with 0.1 mg/kg ODN (15A); 15 hours after dosing with 0.1 mg/kg ODN (15B); 8 hours after dosing with 1 mg/kg ODN (15C); and 15 hours after dosing with 1 mg/kg ODN (15D).
Figure 15B:
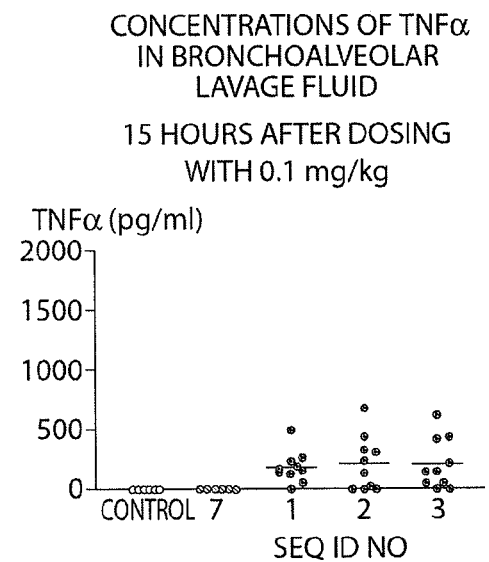
Figure 15C:
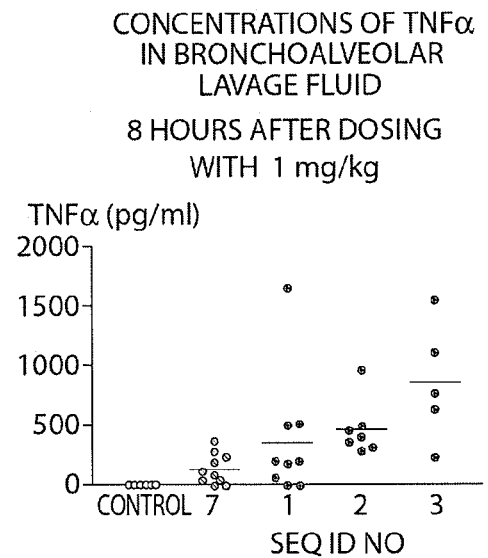
Figure 15D:
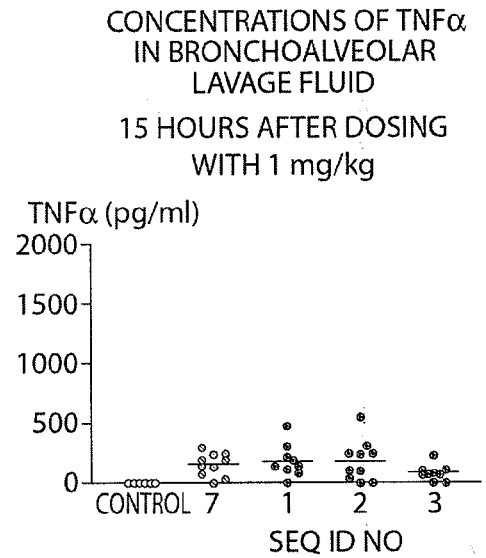
Figure 16A:
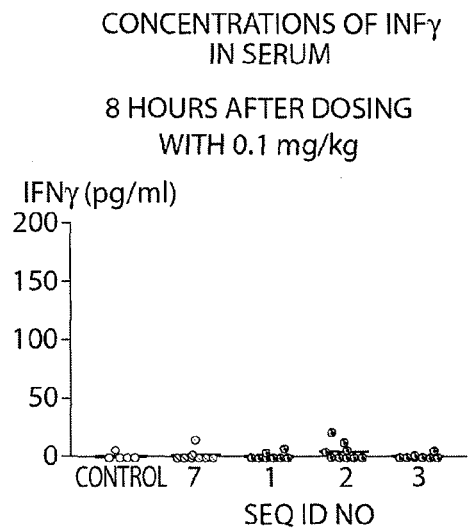
FIG. 16 is a series of graphs depicting concentrations of IFN gamma in serum 8 hours after dosing with 0.1 mg/kg ODN (16A); 15 hours after dosing with 0.1 mg/kg ODN (16B); 8 hours after dosing with 1 mg/kg ODN (16C); and 15 hours after dosing with 1 mg/kg ODN (16D).
Figure 16B:
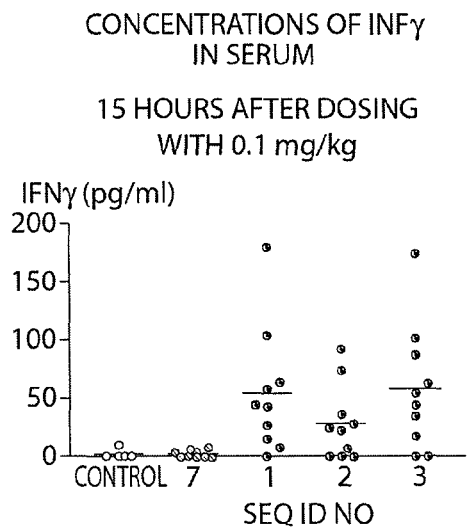
Figure 16C:
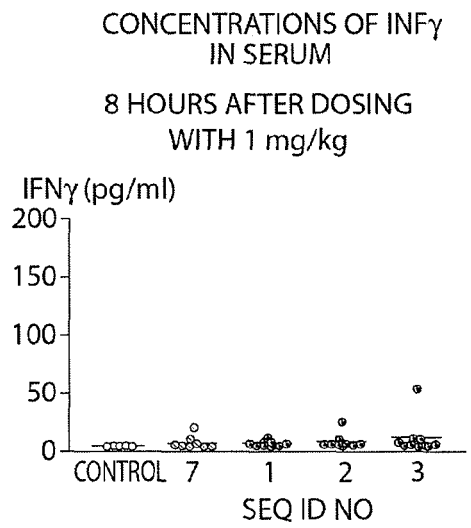
Figure 16D:
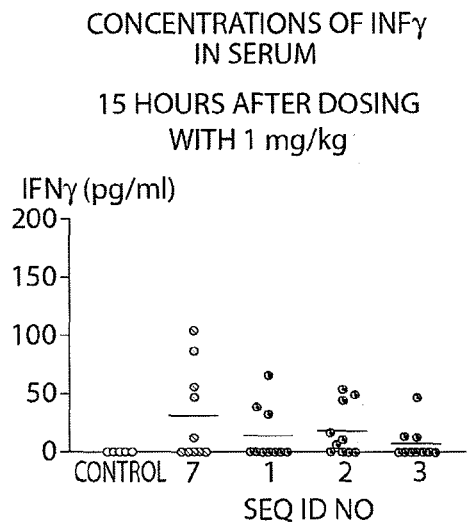
Figure 17A:
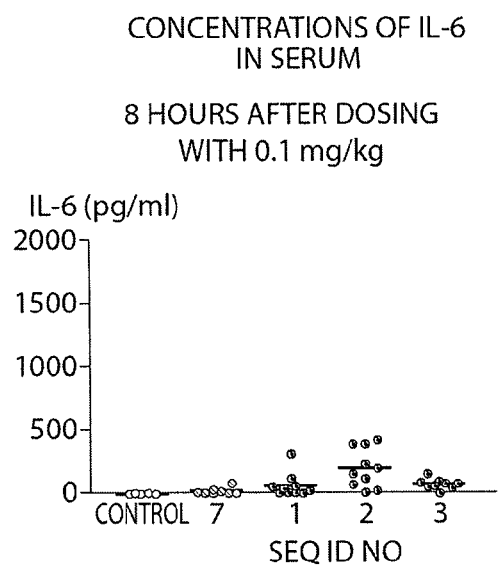
FIG. 17 is a series of graphs depicting concentrations of IL-6 in serum 8 hours after dosing with 0.1 mg/kg ODN (17A); 15 hours after dosing with 0.1 mg/kg ODN (17B); 8 hours after dosing with 1 mg/kg ODN (17C); and 15 hours after dosing with 1 mg/kg ODN (17D).
Figure 17B:
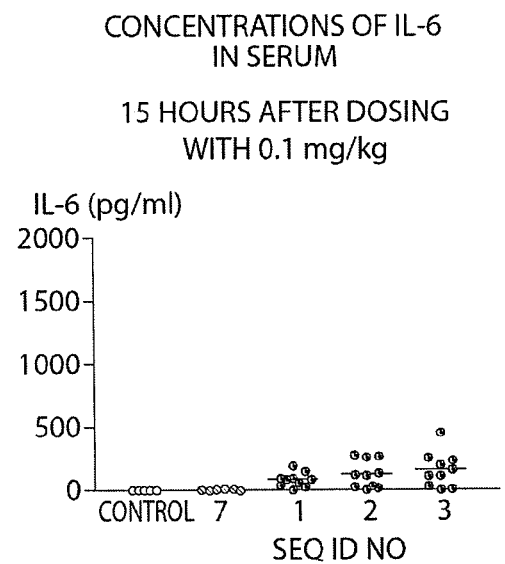
Figure 17C:
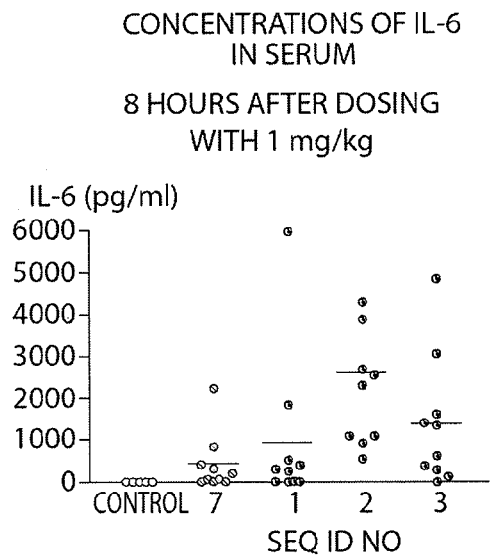
Figure 17D:
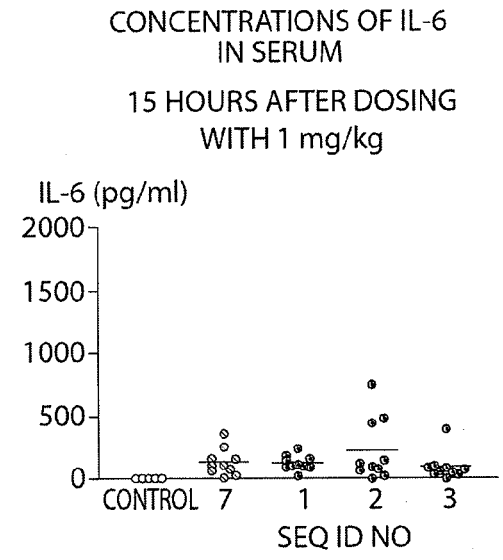
Figure 18A:
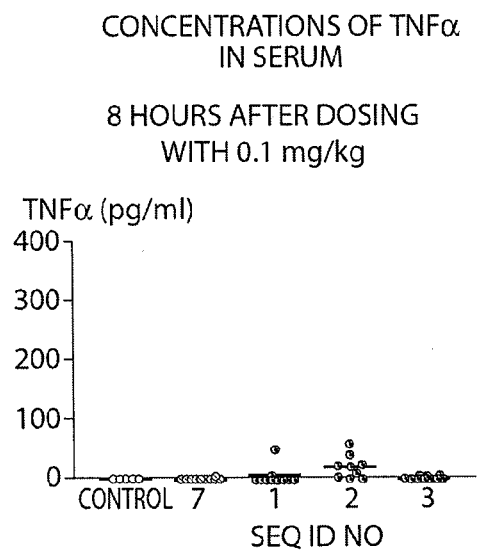
FIG. 18 is a series of graphs depicting concentrations of TNF alpha in serum 8 hours after dosing with 0.1 mg/kg ODN (18A); 15 hours after dosing with 0.1 mg/kg ODN (18B); 8 hours after dosing with 1 mg/kg ODN (18C); and 15 hours after dosing with 1 mg/kg ODN (18D).
Figure 18B:
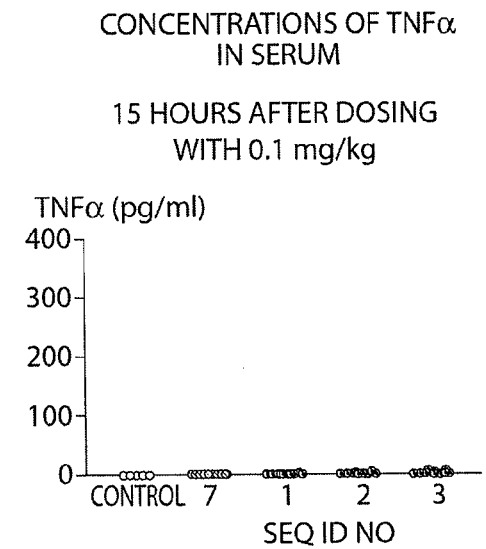
Figure 18C:
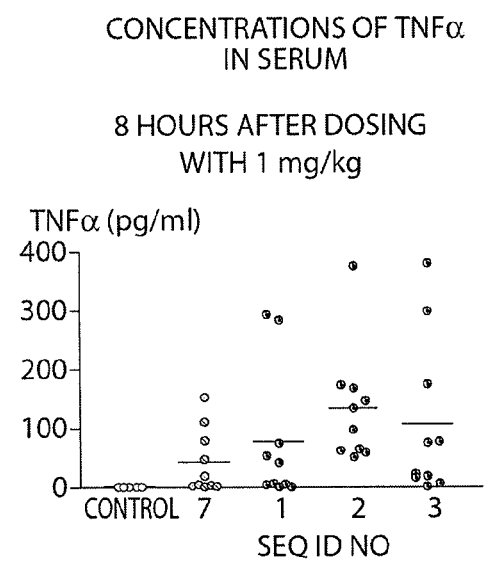
Figure 18D:
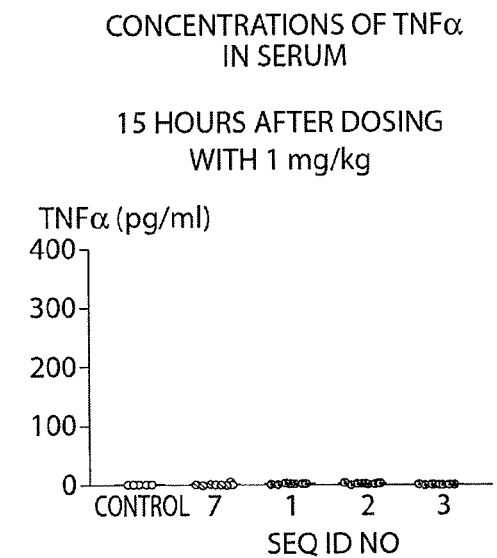

Results: Antigen challenge caused accumulations of eosinophils and T cells in the airways (FIGS. 7 and 8). There was no accumulation of neutrophils. Each of the CpG ODNs caused a significant suppression of eosinophil accumulation at the highest dose tested (100 mg/kg) (FIG. 7). Numbers of T cells were also lower, although the reductions were not generally statistically significant (FIG. 8).

Example 7

Cytokine Induction by Class C CpG Oligodeoxynucleotides in the Mouse in Vivo

The activities of three class C CpG oligodeoxynucleotides (ODNs) were compared. The class B CpG ODN SEQ ID NO:7 was included in the study for comparison.

Methods: Concentrations of cytokines and chemokines in bronchoalveolar lavage fluid and serum were assayed as described in materials and methods.

TABLE 7

Treatment groups

| CpG oligodeoxynucleotide | | | Intranasal doses | Time points for sample collection |
|---|---|---|---|---|
| Vehicle | | | | 8, 15 hours |
| SEQ ID NO: 7 | Semi-soft class B | Lot A25-0313-L1 | 0.1, 1 mg/kg | 8, 15 hours |
| ODN SEQ ID NO: 1 | Semi-soft class C | Lot C44-1209-M1B | 0.1, 1 mg/kg | 8, 15 hours |
| ODN SEQ ID NO: 2 | Semi-soft class C | Lot C44-1209-M2D | 0.1, 1 mg/kg | 8, 15 hours |
| ODN SEQ ID NO: 3 | Semi-soft class C | Lot C44-1209-M4B | 0.1, 1 mg/kg | 8, 15 hours |

Results: FIG. 9 shows cell numbers in bronchoalveolar lavage fluid. Intranasal instillation of each of the class C ODNs, especially at 1 mg/kg, showed a trend to causing a very mild accumulation of leukocytes in bronchoalveolar lavage fluid.

FIGS. 10-15 show cytokine concentrations in bronchoalveolar lavage fluid. Intranasal instillation of each of the CpG ODNs induced measurable titers of IFNα, IFNγ, IP-10, IL-12p40, IL-6 and TNFα in bronchoalveolar lavage fluid. Titers of the other analytes measured did not reach detectable concentrations or concentrations above background (typically <20 pg/ml, data not shown). The class C ODNs were each more potent than the class B ODN SEQ ID NO:7 as inducers of IFNα, IFNγ, IP-10, IL-12p40, IL-6 and TNFα. The increased potency of the class C ODNs was especially apparent at the 0.1 mg/kg dose level. Of particular interest was the observation that only the class C ODNs were able to induce any measurable titers of IFNα and IFNγ after dosing at 0.1 mg/kg (FIG. 10).

FIGS. 15-18 show cytokine concentrations in serum. Intranasal instillation of each of the CpG ODNs induced measurable titers of IFNγ, IL-6 and TNFα in serum. Titers of the other analytes measured did not reach detectable concentrations (typically <20 pg/ml, data not shown). When compared with the class B CpG SEQ ID NO:7, each of the three class C ODNs were more potent inducers of the immune-modifying cytokines IFNα, IFNγ, IP-10, IL-12p40, IL-6 and TNFα.

Example 8

Effects of CpG Oligodeoxynucleotides SEQ ID NO:2 and SEQ ID NO:7 on Antigen-Induced IgE Production in the Mouse Methods: Mice (male BALB/c) were sensitized on study days 0 and 7 with antigen (ovalbumin, 10 µg, i.p.) and aluminum hydroxide adjuvant Pierce Alum, i.p.). Mice received SEQ ID NO:2 or SEQ ID NO:7 on study days −2, 0, 5 and 7 (i.e. two days before each sensitization and on the day of sensitization). Mice were bled by cardiac puncture on study day 18. Serum was collected by centrifugation and assayed by ELISA for ovalbumin-specific IgE and IgG2a.

TABLE 8

Treatment groups:

| | Sensitization | Treatment | n |
|---|---|---|---|
| 1 | None | None | 5 |
| 2 | Antigen | Vehicle, i.p. | 10 |
| 3 | Antigen | SEQ ID NO: 2, 1 µg/kg, i.p. | 10 |

TABLE 8-continued

Treatment groups:

| | Sensitization | Treatment | n |
|---|---|---|---|
| 4 | Antigen | SEQ ID NO: 2, 10 µg/kg, i.p. | 10 |
| 5 | Antigen | SEQ ID NO: 2, 100 µg/kg, i.p. | 10 |

TABLE 8-continued

| | Treatment groups: | | |
|---|---|---|---|
| | Sensitization | Treatment | n |
| 6 | Antigen | SEQ ID NO: 2, 1000 µg/kg, i.p. | 10 |
| 7 | Antigen | SEQ ID NO: 7, 1 µg/kg, i.p. | 10 |
| 8 | Antigen | SEQ ID NO: 7, 10 µg/kg, i.p. | 10 |
| 9 | Antigen | SEQ ID NO: 7, 100 µg/kg, i.p. | 10 |
| 10 | Antigen | SEQ ID NO: 7, 1000 µg/kg, i.p. | 10 |

TABLE 9

Summary of study protocol

| Day: | ODN −2 | Immunize ODN 0 | ODN 5 | Immunize ODN 7 | 18 |
|---|---|---|---|---|---|
| | | | | | Endpoints |

Figure 19A:
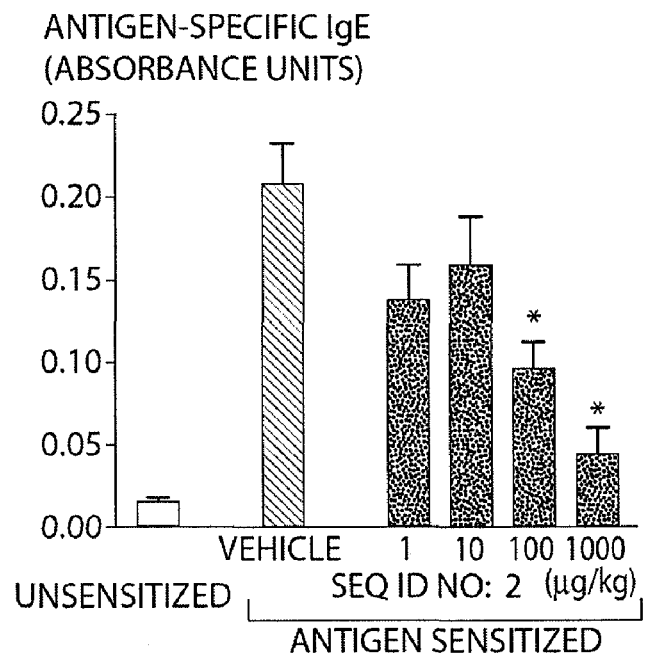
FIG. 19 is a series of graphs depicting the effects of CpG oligodeoxynucleotides ODN SEQ ID NO: 2 and ODN SEQ ID NO: 7 on antigen-induced IgE (19A) and IgG2a (19B) production in the mouse. Results are mean±s.e.m. (n=10). * $P<0.05$ compared with antigen sensitized, vehicle-treated group (Kruskal-Wallis test with Dunn's post test).
Figure 19B:
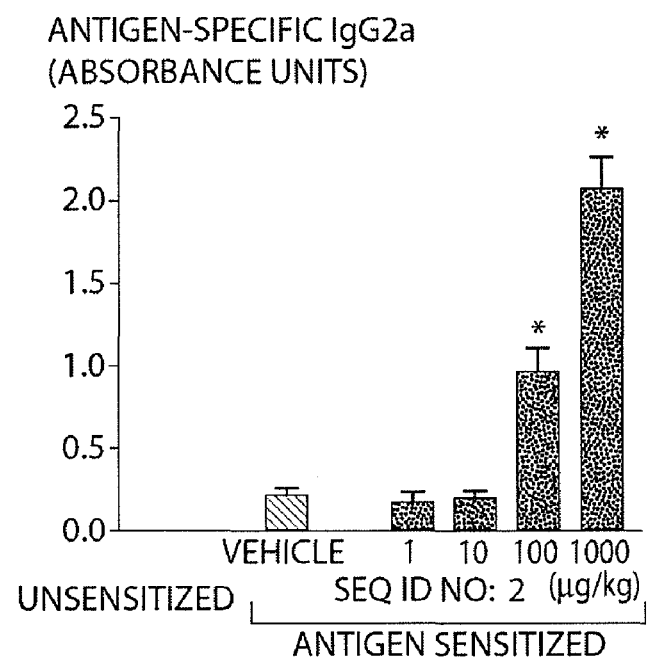

Results: Antigen sensitization resulted in serum titers of antigen (ovalbumin)-specific IgE and IgG2a. The production of IgE was suppressed in mice treated with either SEQ ID NO:2 or SEQ ID NO:7, while the production of IgG2a was potentiated (FIG. 19).

Conclusions: The data of Example 8 demonstrates that SEQ ID NO:2 and SEQ ID NO:7 suppress Th2-associated production of IgE in response to antigen sensitization, and potentiate Th1-associated IgG2a production. The results of this study provide further evidence that these CpG oligos can suppress a Th2-type response to antigen exposure in the mouse.

Example 9

Effects of SEQ ID NO:2 Against Exacerbated Airways Inflammation Induced by Combined Influenza Infection and Antigen Challenge Introduction: The class C CpG oligodeoxynucleotide SEQ ID NO:2 can suppress influenza virus load and virus-induced airways inflammation in mice. The present study investigated the protective effects of SEQ ID NO:2 against the exacerbated airways inflammation induced by combined influenza virus infection and antigen challenge.

Methods: Antigen and virus administrations: Mice (male BALB/c) were sensitized on study days 0 and 7 with antigen (cockroach, 10 µg, intraperitoneal) with aluminum hydroxide adjuvant (Pierce Alum). Mice were antigen challenged by exposure to intranasally-administered antigen (10 µg in 40 µl saline), twice each week for three consecutive weeks. The first challenge was on study day 21. Mice were infected with influenza virus (influenza type A, subtype H1N1, mouse adapted strain PR8, 200 $EID_{50}$ in 40 µl saline) by intranasal instillation on study day 34 (i.e. before the last pair of antigen challenges). Alternatively, separate groups of mice received antigen challenge alone or virus infection alone.

SEQ ID NO:2 (100 µg/kg) was administered intranasally once each week, two days before the first antigen challenge of the week. Airways inflammation was assessed 48 hours after the last antigen challenge. Cells in airways were recovered by bronchoalveolar lavage. Differential cell counts were made by light microscopy from cytocentrifuge preparations stained with Wright-Giemza stain.

TABLE 10

Summary of study protocol

| | Antigen sensitize | | ODN | Antigen challenge | | ODN | Antigen challenge | | ODN | Virus | Antigen challenge | |
|---|---|---|---|---|---|---|---|---|---|---|---|---|
| Day: | 0 | 7 | 19 | 21 | 24 | 26 | 28 | 31 | 33 | 34 | 35 | 38 | 40 |
| | First treatment week | | | | | Second treatment week | | | | Third treatment week | | | Endpoints |

Figure 20:
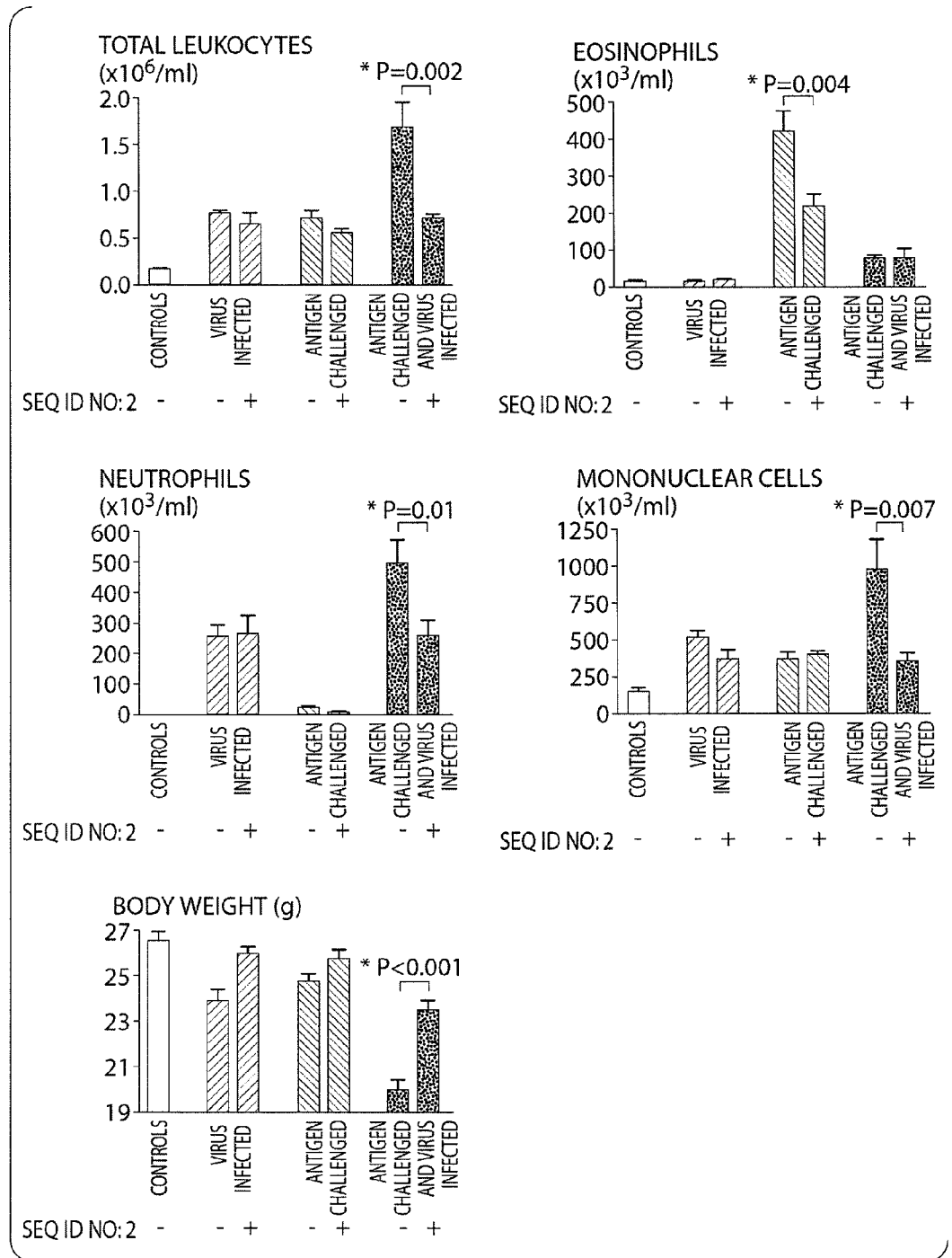
FIG. 20 is a series of graphs depicting Effects of ODN SEQ ID NO: 2 against influenza-induced exacerbation of allergic airway inflammation in mice, depicting total leukocytes (20A), eosinophils (20B), neutrophils (20C), mononuclear cells (20D), and body weight (20E).

Results: FIG. 20 shows that infection with influenza virus alone or antigen challenge alone each caused an increase in the total number of leukocytes in bronchoalveolar lavage fluid. In virus-infected mice, this cell accumulation included a marked neutrophilia, whereas in antigen-challenged mice, the accumulation included a marked eosinophilia. When compared with mice that received antigen challenge alone, those that were antigen-challenged and virus-infected showed an exacerbated accumulation of leukocytes in bronchoalveolar lavage fluid. This increased accumulation included both neutrophils and mononuclear cells. However, these mice showed reduced eosinophilia. Other researchers have similarly shown that influenza infection can suppress airways eosinophilia in antigen-challenged mice, and have hypothesized that this is a Th1-mediated effect (e.g. Wohlleben et al., 2003).

Treatment with SEQ ID NO:2 (100 µg/kg) did not suppress the virus-induced neutrophilia (FIG. 20). This negative finding was expected since, in an earlier study a higher dose of 300 µg/kg was most desirable to show anti-virus effects. Furthermore, SEQ ID NO:2 (100 µg/kg) did significantly suppress antigen-induced eosinophilia. This positive finding was in agreement with earlier studies.

SEQ ID NO:2 (100 µg/kg) significantly suppressed the exacerbated airways inflammation induced in mice that were both virus-infected and antigen-challenged. The exacerbated accumulations of neutrophils and mononuclear cells were both suppressed. In addition to exacerbated airways inflammation, mice that were both virus-infected and antigen-challenged showed a marked loss of body weight. This was significantly suppressed in mice treated with SEQ ID NO:2.

Conclusions: In both children and adults with existing asthma, infections with respiratory tract viruses are important precipitants for airway obstruction and wheezing. The inflammatory processes involved are complex. However, virus-induced neutrophil and mononuclear cell recruitment and activation are implicated in aggravating the airway obstruction that contributes to these asthma exacerbations (reviewed by Gern and Busse, Nature Immunology, 2002). The data of Example 9 demonstrate that SEQ ID NO:2 markedly suppresses the exacerbated accumulations of neutrophils and mononuclear cells induced in mice by combined virus infection and antigen challenge.

Example 10

Guinea Pig Studies

Example 10a

Summary of Guinea Pig AHR Protocol

Figure 21:
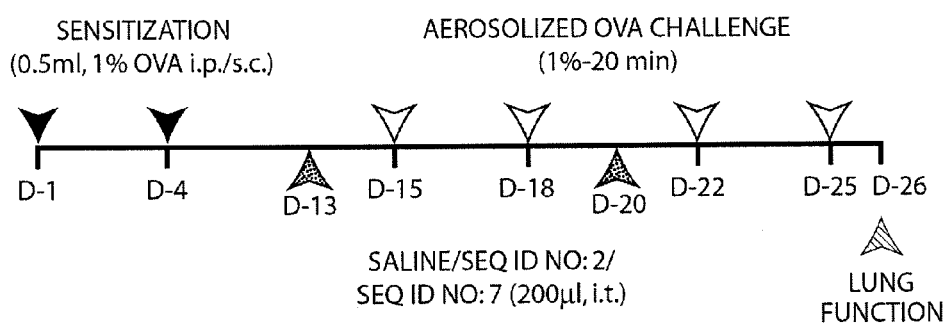
FIG. 21 is a guinea pig AHR Protocol used herein.

Male guinea pigs were sensitized on study days 0 and 4 with antigen (ovalbumin, 0.5 ml, 1% OVA i.p./s.c.) with aluminum hydroxide adjuvant. Guinea pigs were antigen challenged by exposure to inhaled ovalbumin aerosol, twice each week for two consecutive weeks. The first challenge was on study day 13. CpG ODN or vehicle (saline, 20 µl) were administered intranasally once each week, two days before the first antigen challenge of the week. Airways hyperreactivity was assessed 24 hours after the last antigen challenge by measuring bronchoconstriction (increase in airway resistance) to intravenous methacholine. For each animal, a dose-response curve to methacholine was obtained, and airway reactivity was quantified as the area under the curve. FIG. 21 shows a schematic of the procedure.

Example 10b

Effect of SEQ ID NO:7 on Airway Resistance and Lung Compliance in Guinea Pigs

Method: Guinea pigs were sensitized as described in Example 10. The first challenge was on study day 13. Guinea pigs were given intranasally either carrier (saline), OVA alone, of concentrations of SEQ ID NO:7 of 10 µl/kg, 30 µl/kg, 100 µl/kg, or 300 µl/kg, i.t.

Figure 22:
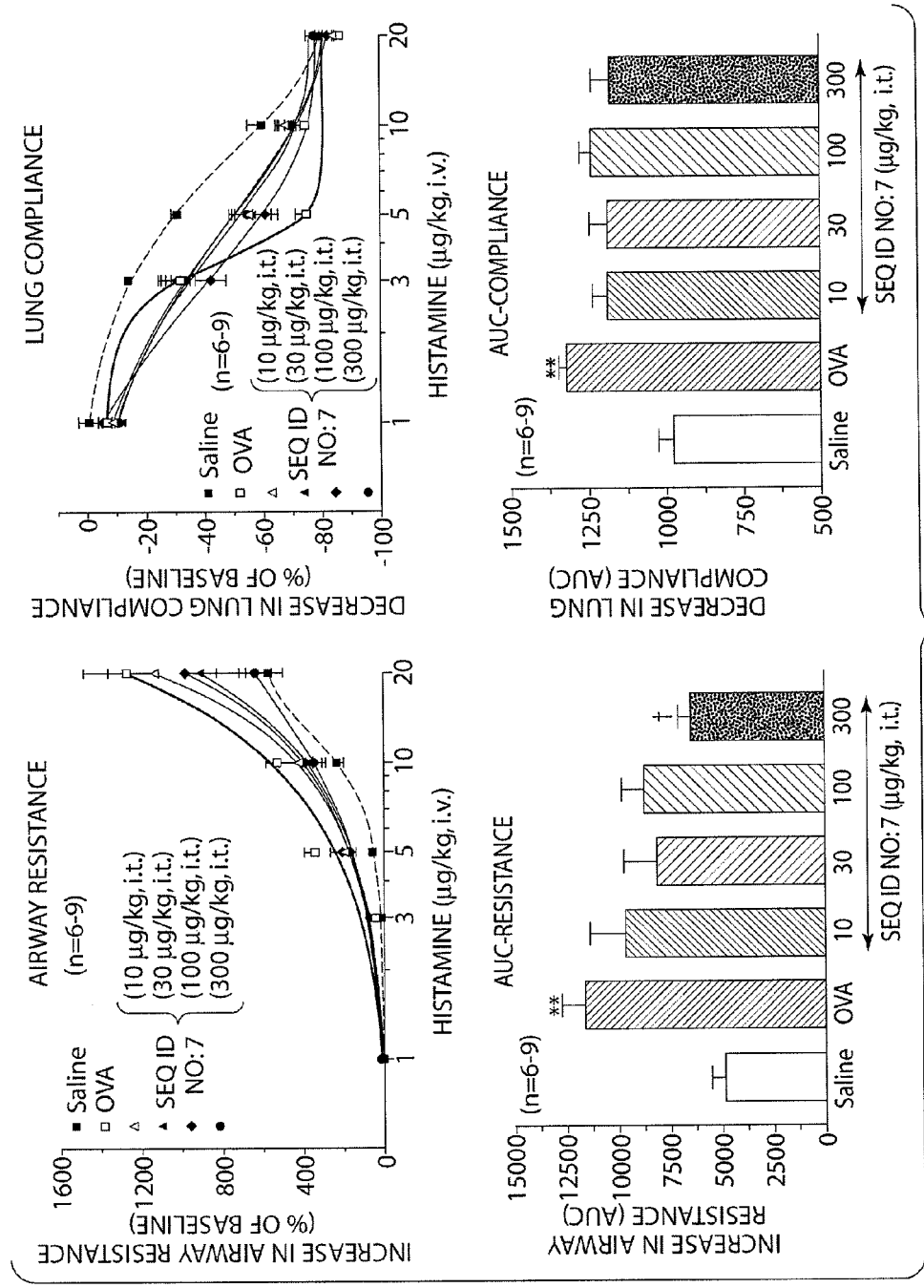
FIG. 22 is a set of graphs depicting the effect of SEQ ID NO:7 on Airway resistance and lung compliance. For each animal, a dose-response curve was obtained, and airway reactivity was quantified as the area under the curve. Guinea pigs were given intranasally either carrier (saline), OVA alone, or concentrations of SEQ ID NO:7 of 10 µl/kg, 30 µl/kg, 100 µl/kg, or 300 µl/kg, i.t. The data demonstrate that SEQ ID NO:7 caused a dose-dependent reduction in AUC-resistance.

Results: FIG. 22 shows that SEQ ID NO:7 caused a dose-dependent reduction in AUC-resistance.

Example 10c

Statistical Analysis of the Effect of SEQ ID NO:7 on Airway Resistance and Lung Compliance in Guinea Pigs Method: The Dunnett multiple comparisons test was used to analyze the data from the experiments in Example 10b. The Dunnett multiple comparisons test allows comparison of all samples to a single control group.

Results: FIG. 23 shows that SEQ ID NO:7 caused a dose-dependent reduction in AUC-resistance.

Example 10d

Effect of SEQ ID NO:2 on Airway Resistance and Lung Compliance in Guinea Pigs

Method: Guinea pigs were sensitized as described in Example 10. The first challenge was on study day 13. Guinea pigs were given intranasally either carrier (saline), OVA alone, of concentrations of SEQ ID NO:2 of 10 µl/kg, 30 µl/kg, 100 µl/kg, or 300 µl/kg, i.t.

Figure 24:
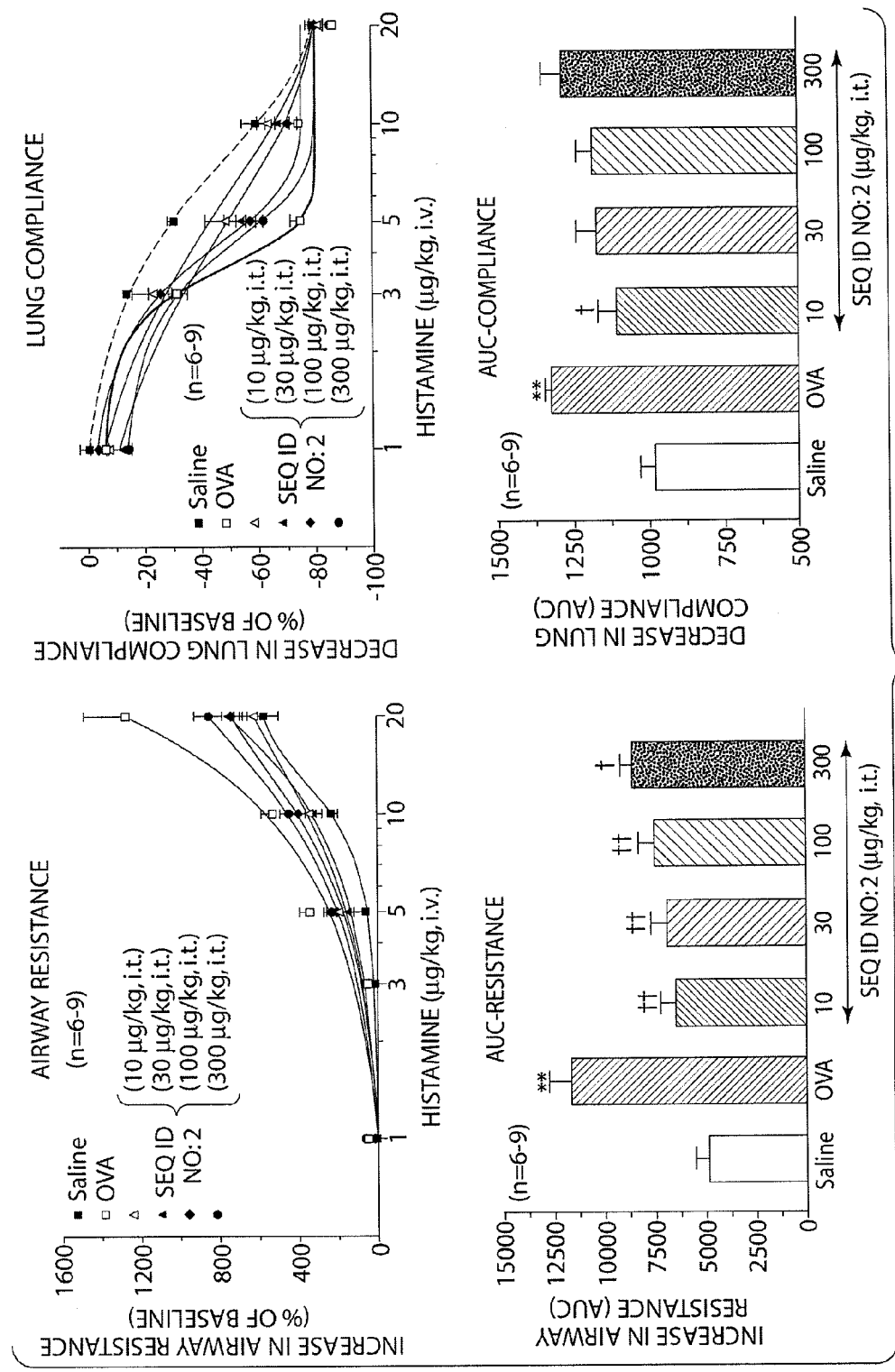
FIG. 24 is a set of graphs depicting the effect of SEQ ID NO:2 on Airway resistance and lung compliance. For each animal, a dose-response curve was obtained, and airway reactivity was quantified as the area under the curve. Guinea pigs were given intranasally either carrier (saline), OVA alone, or concentrations of SEQ ID NO:2 of 10 µl/kg, 30 µl/kg, 100 µl/kg or 300 µl/kg, i.t. The data demonstrate that SEQ ID NO:2 caused a dose-dependent reduction in AUC-resistance.
Figure 26A:
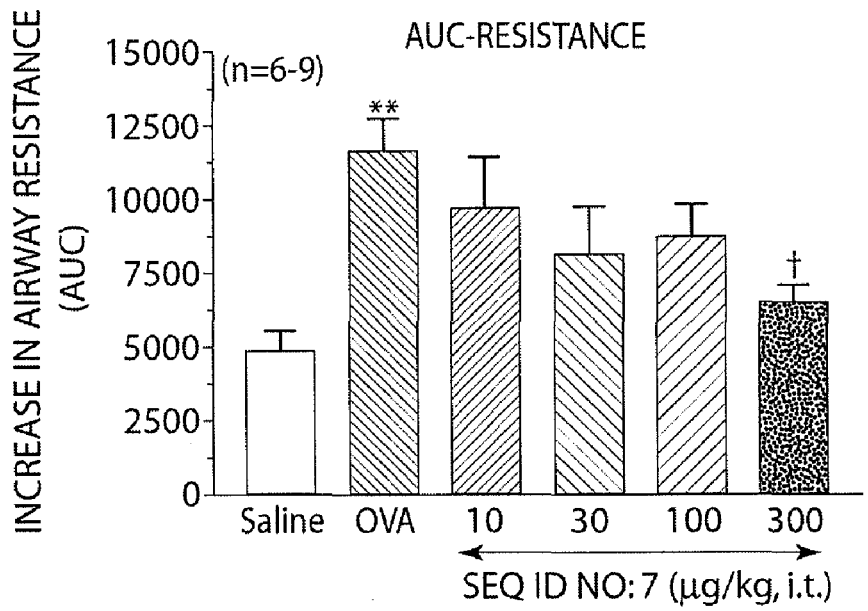
FIGS. 26A and 26B correspond to FIGS. 22C and 22D.
Figure 26B:
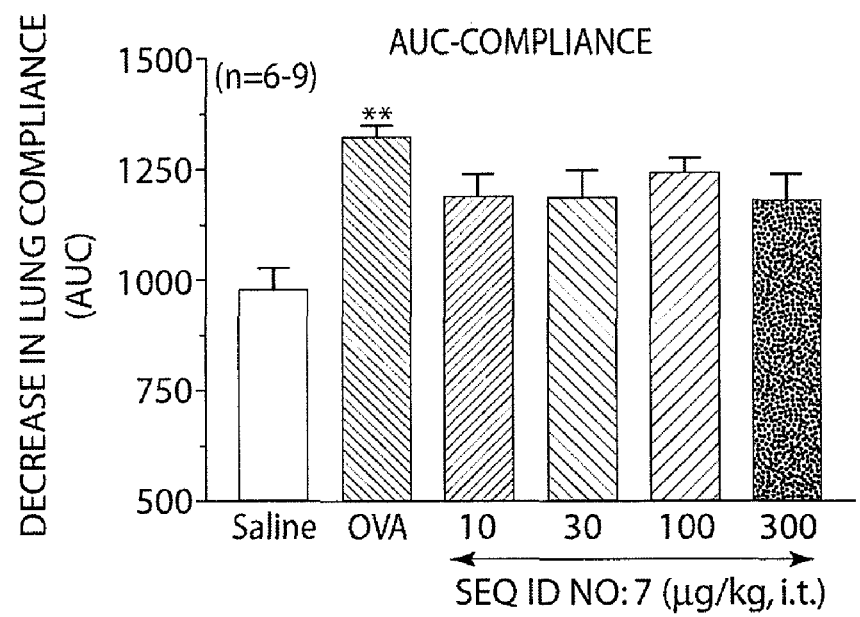
Figure 26C:
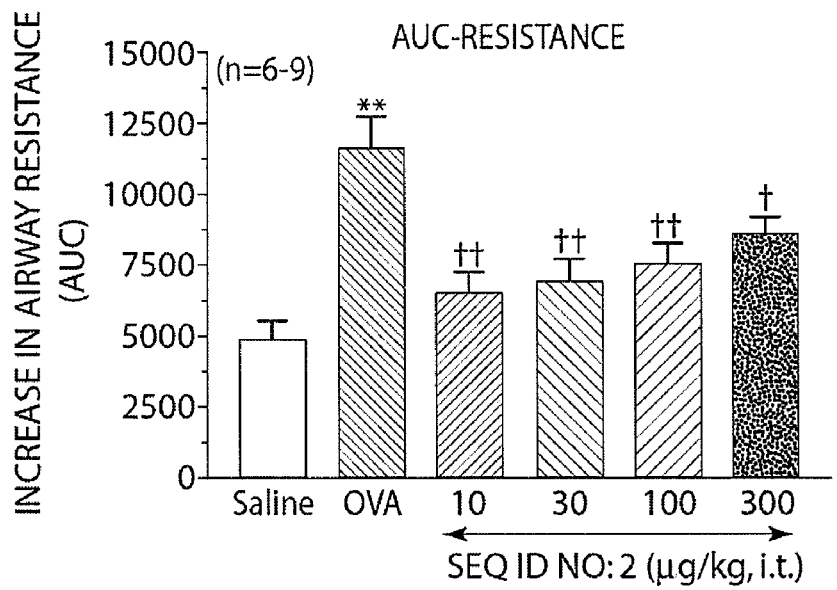
FIGS. 26C and 26D correspond to FIGS. 24C and 24D.
Figure 26D:
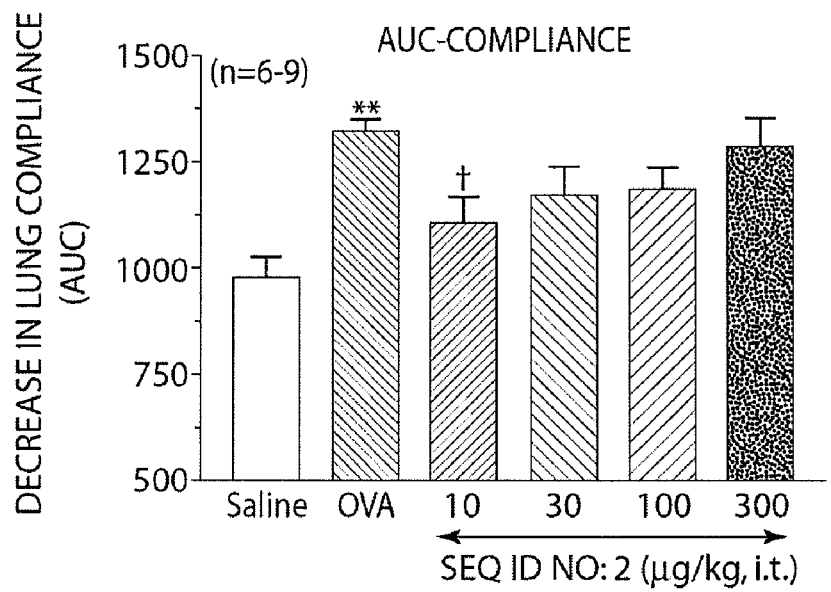

Results: FIG. 24 shows that SEQ ID NO:2 caused a dose-dependent reduction in AUC-resistance.

Example 10e

Statistical Analysis of the effect of SEQ ID NO:2 on Airway Resistance and Lung Compliance in Guinea Pigs Method: The Dunnett multiple comparisons test was used to analyze the data from the experiments in Example 10d. The Dunnett multiple comparisons test allows comparison of all samples to a single control group Results: FIG. 25 shows that SEQ ID NO:2 caused a dose-dependent reduction in AUC-resistance.

Example 11

Levels of IL-10, TNF-alpha, interferon-gamma, and IL-6 (pg/ml) produced by human PBMC following exposure of these cells to the CpG oligonucleotides described herein is shown in the attached FIG. 27-31. The test oligonucleotides shown in FIG. 27 include SEQ ID NOs: 10, 9, 13, 14, 1, and 2. The concentration of oligonucleotide used to produce a particular data point is depicted along the X-axis (µM).

Figure 27:
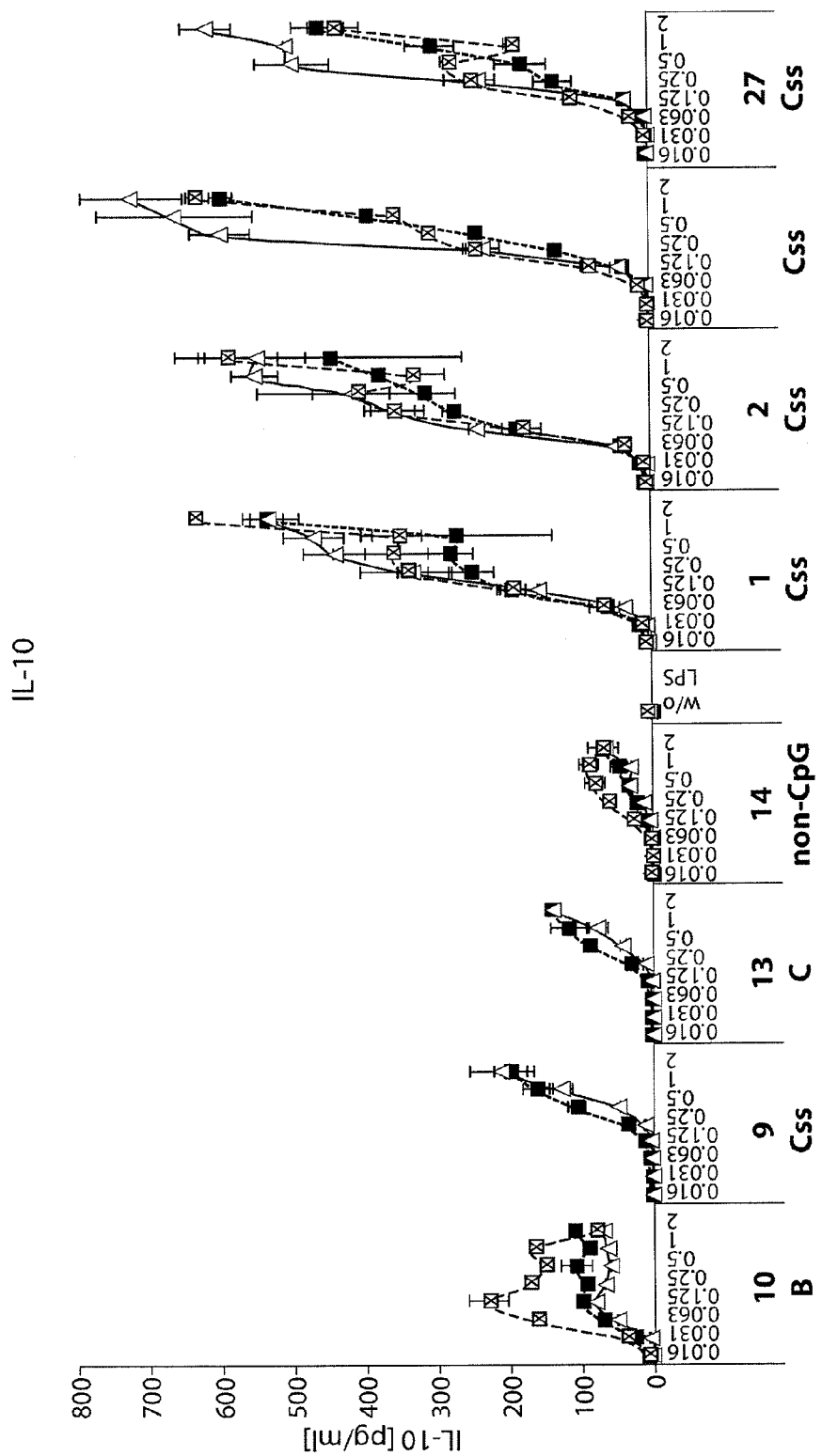
FIG. 27 is a set of graphs depicting levels of IL-10 µg/ml) secreted from human PBMC (3 donors) following exposure of these cells to the oligonucleotides listed by SEQ ID No. along the bottom X-axis of the graph (data points from the 3 donors are depicted by a ▲, ■ and x) for 48 hours. The test oligonucleotides shown in FIG. 27 include SEQ ID NOs: 10, 9, 13, 14, 1, and 2. The concentration of oligonucleotide used to produce a particular data point is depicted along the X-axis (µM). Supernatants were harvested and IL-10 measured by ELISA. Given are the mean cytokine amounts of all donors.

As demonstrated in FIG. 27 each of the oligonucleotides tested in the assays were able to produce different levels and patterns of IL-10 secretion. Of those tested ODN SEQ ID NO 1 and 2 resulted in dramatically higher induction of IL-10.

Figure 28A:
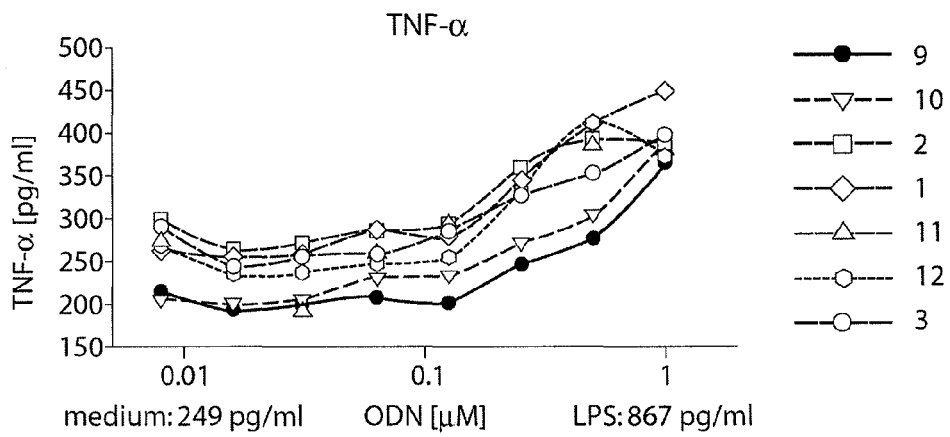
FIG. 28 is a set of graphs depicting levels of TNF-alpha (28A), interferon-gamma (28B), and IL-6 (28C) (µM) secreted from human PBMC following exposure of these cells to the oligonucleotides listed by SEQ ID NO. in the key of the graph. Each data point is the calculated mean cytokine value of three donors. The PBMC were incubated with the indicated ODN concentrations. Supernatants were harvested and cytokines measured by ELISA. Given are the calculated mean cytokine amounts of all donors.
Figure 28B:
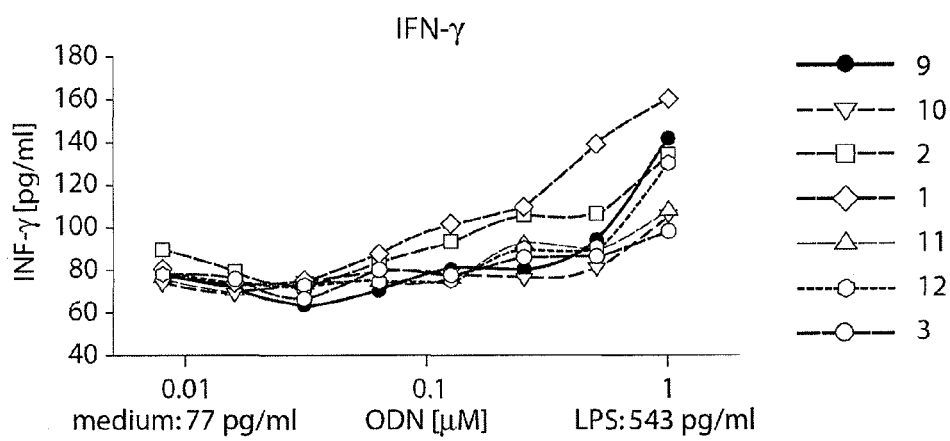
Figure 28C:
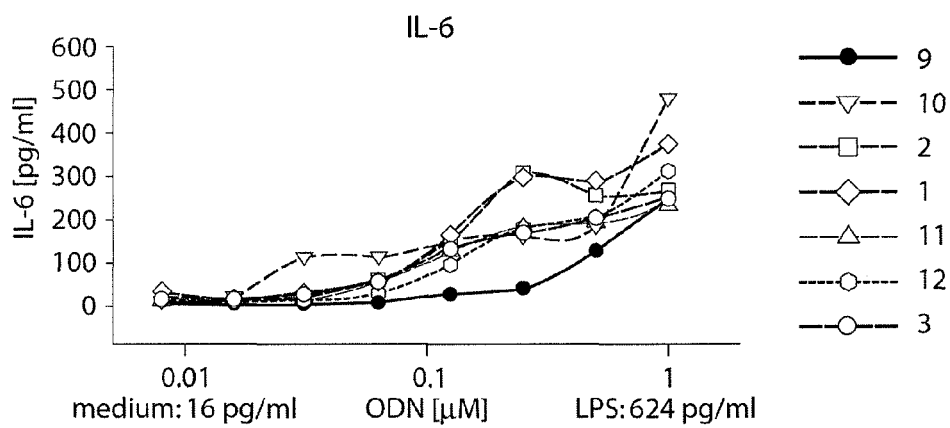
Figure 29:
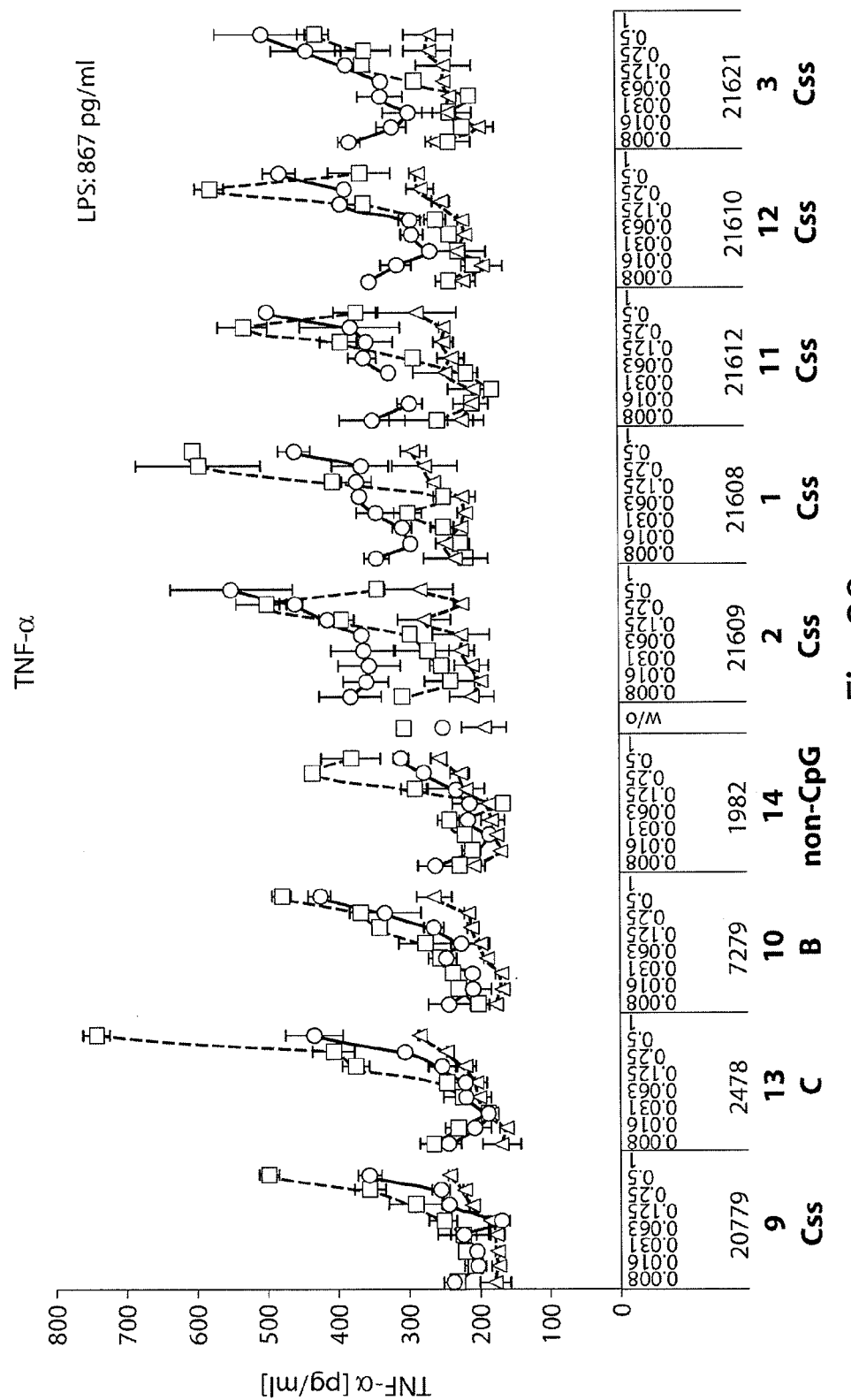
FIG. 29 is a set of graphs depicting levels of TNF-alpha (pg/ml) secreted from human PBMC following exposure of these cells to the oligonucleotides for 16 hours listed by the SEQ ID NO along the bottom X-axis of the graph. The oligonucleotides shown in FIG. 29 include SEQ ID NO: 9, 13, 10, 14, 2, 1, 11, 12, and 3. The concentration of oligonucleotide used to produce a particular data point is depicted along the X-axis (µM). The data shown represents the values of three donors. Below the SEQ ID NOs is a designation referring to the class of ODN. Css=C-class semi soft, C=C-class, B=B-class, non-CpG=an ODN without an unmethylated CpG. Supernatants were harvested and IL-6 measured by ELISA. Given are the mean cytokine amounts of all donors.
Figure 30:
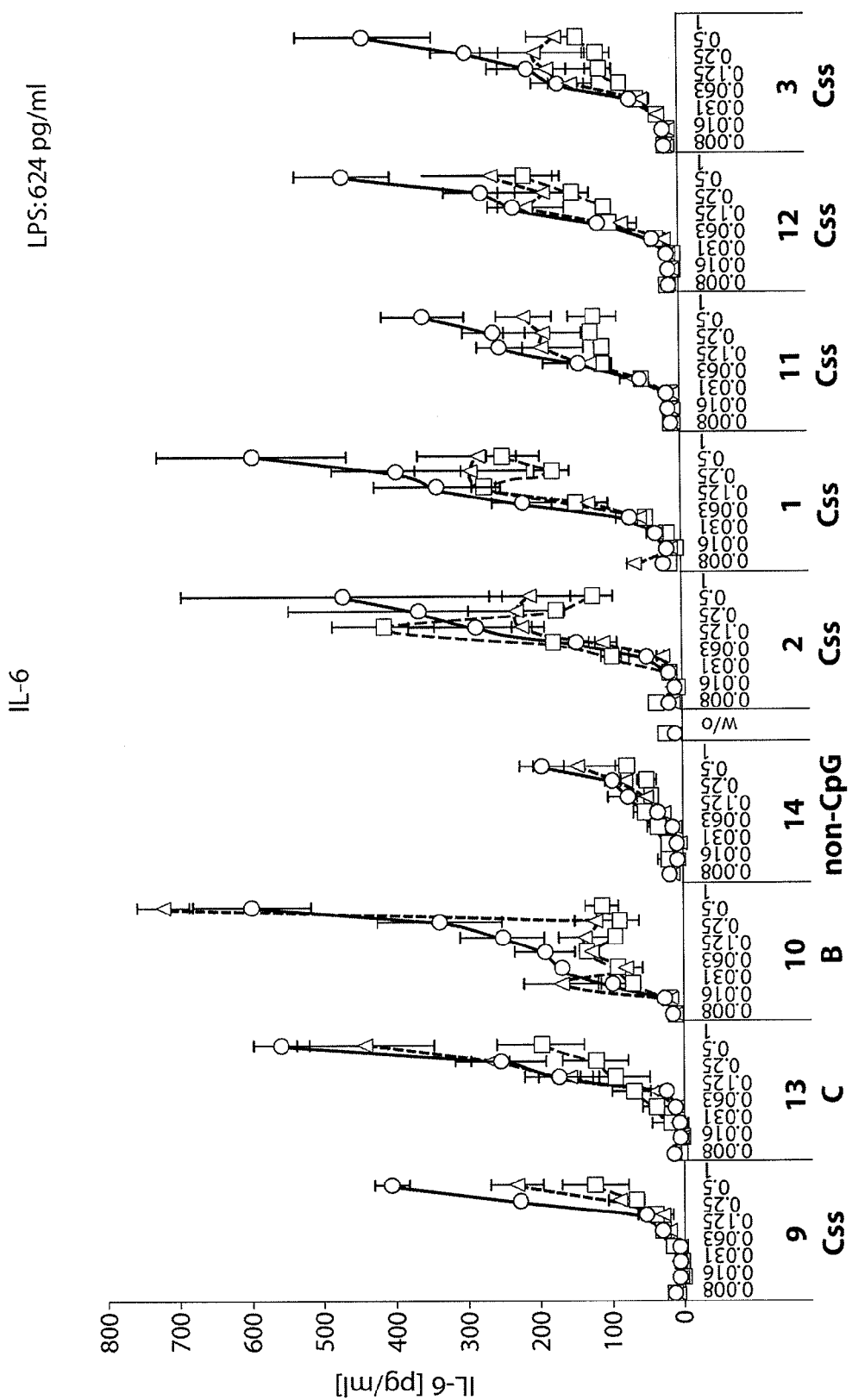
FIG. 30 is a set of graphs depicting levels of IL-6 (pg/ml) secreted from human PBMC following exposure of these cells to the oligonucleotides for 24 hours listed by the SEQ ID NO along the bottom X-axis of the graph. The oligonucleotides shown in FIG. 30 include SEQ ID NO: 9, 13, 10, 14, 2, 1, 11, 12, and 3. The concentration of oligonucleotide used to produce a particular data point is depicted along the X-axis (µM). The data shown represents the values of three donors. Below the SEQ ID NOs is a designation referring to the class of ODN. Css=C-class semi soft, C=C-class, B=B-class, non-CpG=an ODN without an unmethylated CpG.
Figure 31:
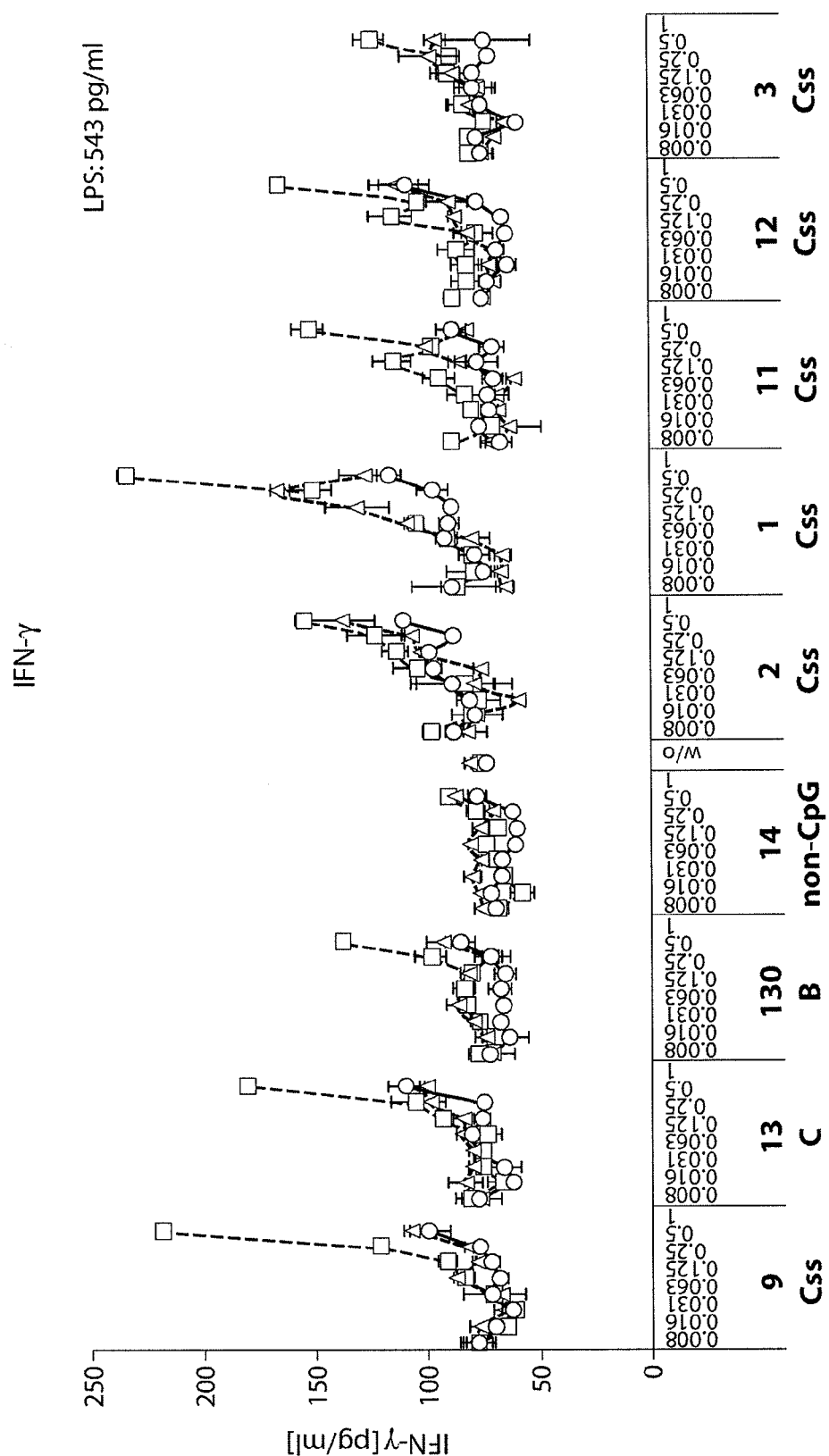
FIG. 31 is a set of graphs depicting levels of IFN-gamma (pg/ml) secreted from human PBMC following exposure of these cells to the oligonucleotides for 48 hours listed by the SEQ ID NO along the bottom X-axis of the graph. The oligonucleotides shown in FIG. 31 include SEQ ID NO. 9, 13, 10, 14, 2, 1, 11, 12, and 3. The concentration of oligonucleotide used to produce a particular data point is depicted along the X-axis ($\mu$M). The data shown represents the values of three donors, Below the SEQ ID NOs is a designation referring to the class of ODN. Css=C-class semi soft, C=C-class, B=B-class, non-CpG=an ODN without an unmethylated CpG. Supernatants were harvested and IFN-gamma measured by ELISA. Given are the mean cytokine amounts of all donors.

FIG. 28 depicts data relating to TNF-alpha, interferon-gamma, and IL-6 at three representative doses. More detailed graphs on these cytokines are depicted in FIGS. 29-31 with additional oligonucleotide dosages.

Example 12

Levels of B cell, plasmacytoid dendritic cell and monocyte activation following exposure of these cells to the CpG oligonucleotides described herein is shown in the attached FIGS. 32-42. The oligonucleotides examined are depicted in the Figures by SEQ ID NO and included SEQ ID NO: 9, 13, 10, 14, 2, 1, 11, 12, and 3. The concentration of oligonucleotide used to produce a particular data point is depicted along the X-axis (µM).

Figure 32A:
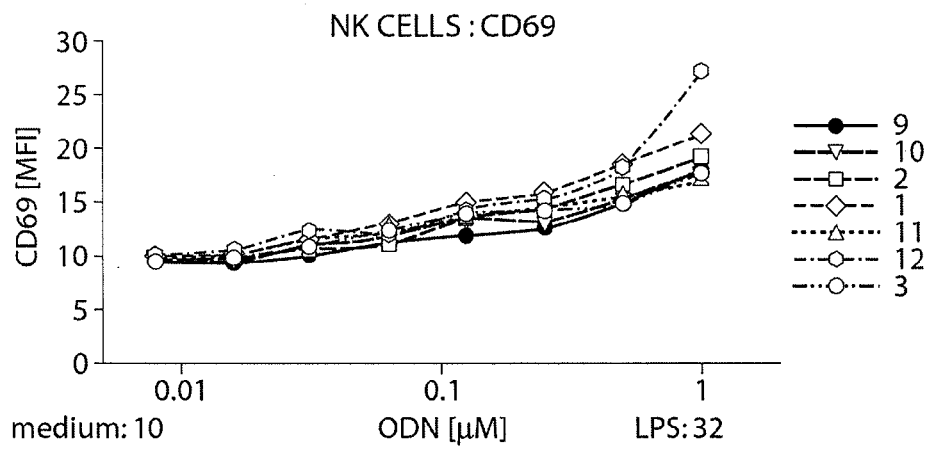
FIG. 32 is a set of graphs depicting levels of CD69 expression (MFI) on NK cells as an indicator of NK cell activation (32A) and CD80 (32B) and CD86 (32C) expression on B cells following exposure of these cells to the oligonucleotides for 24 or 48 hours listed by SEQ ID NO. in the key of the graph. Each data point is the mean fluorescence intensity of three donors. The cells were incubated with the indicated ODN concentrations for 24, or 48 hours. Cells were stained and analyzed by flow cytometry.
Figure 32B:
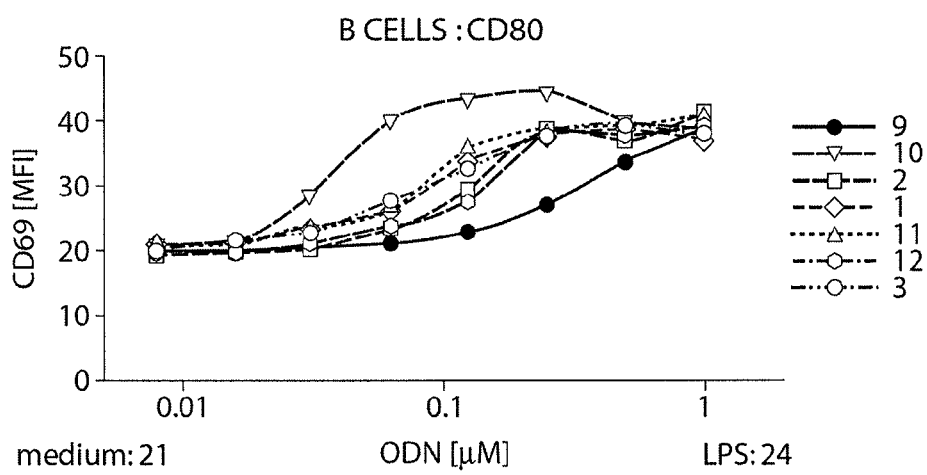
Figure 32C:
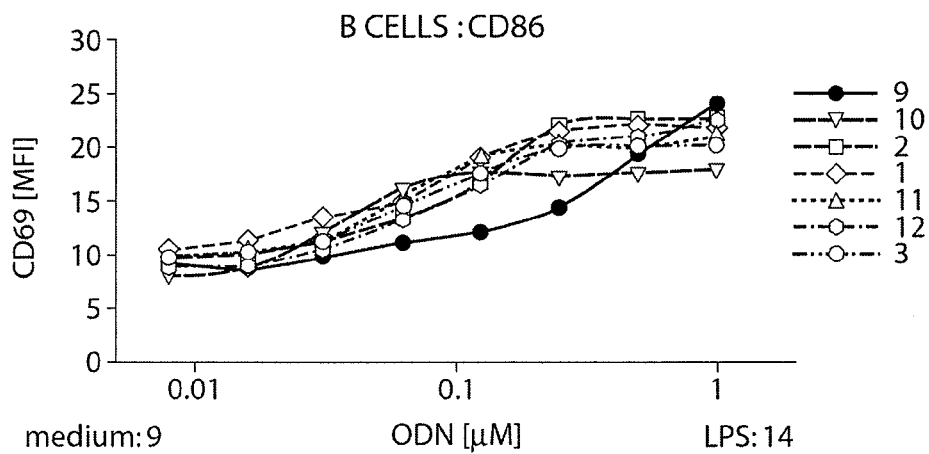
Figure 33:
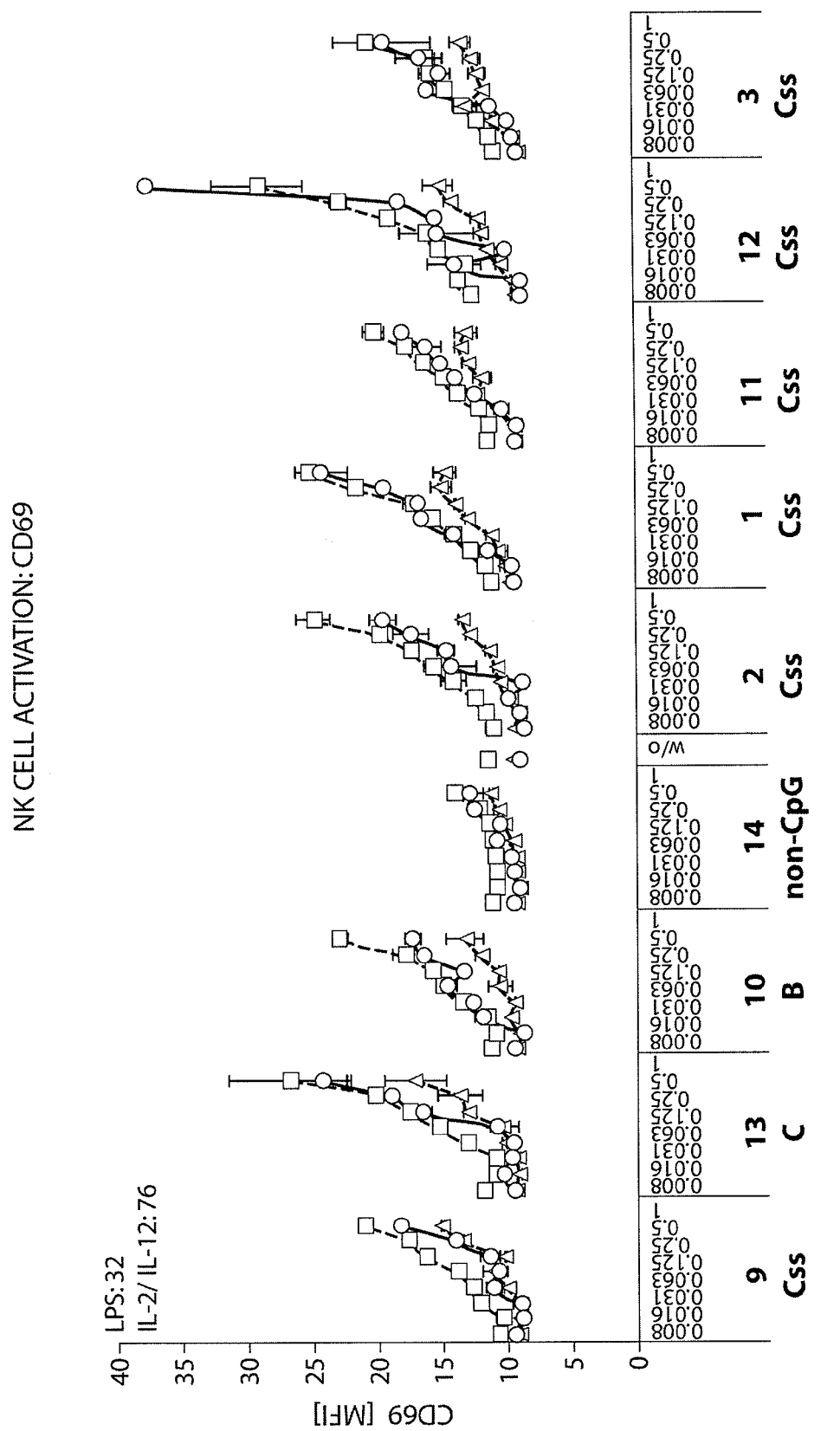
FIG. 33 is a set of graphs depicting levels of levels of CD69 expression on NK cells as an indicator of NK cell activation following exposure of these cells to the oligonucleotides for 24 hours listed by the SEQ ID NO along the bottom X-axis of the graph. The oligonucleotides shown in FIG. 33 include SEQ ID NO: 9, 13, 10, 14, 2, 1, 11, 12, and 3. The concentration of oligonucleotide used to produce a particular data point is depicted along the X-axis ($\mu$M). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD3, CD56, and CD69 and analyzed by flow cytometry. The data presented is the mean fluorescence intensity.
Figure 34:
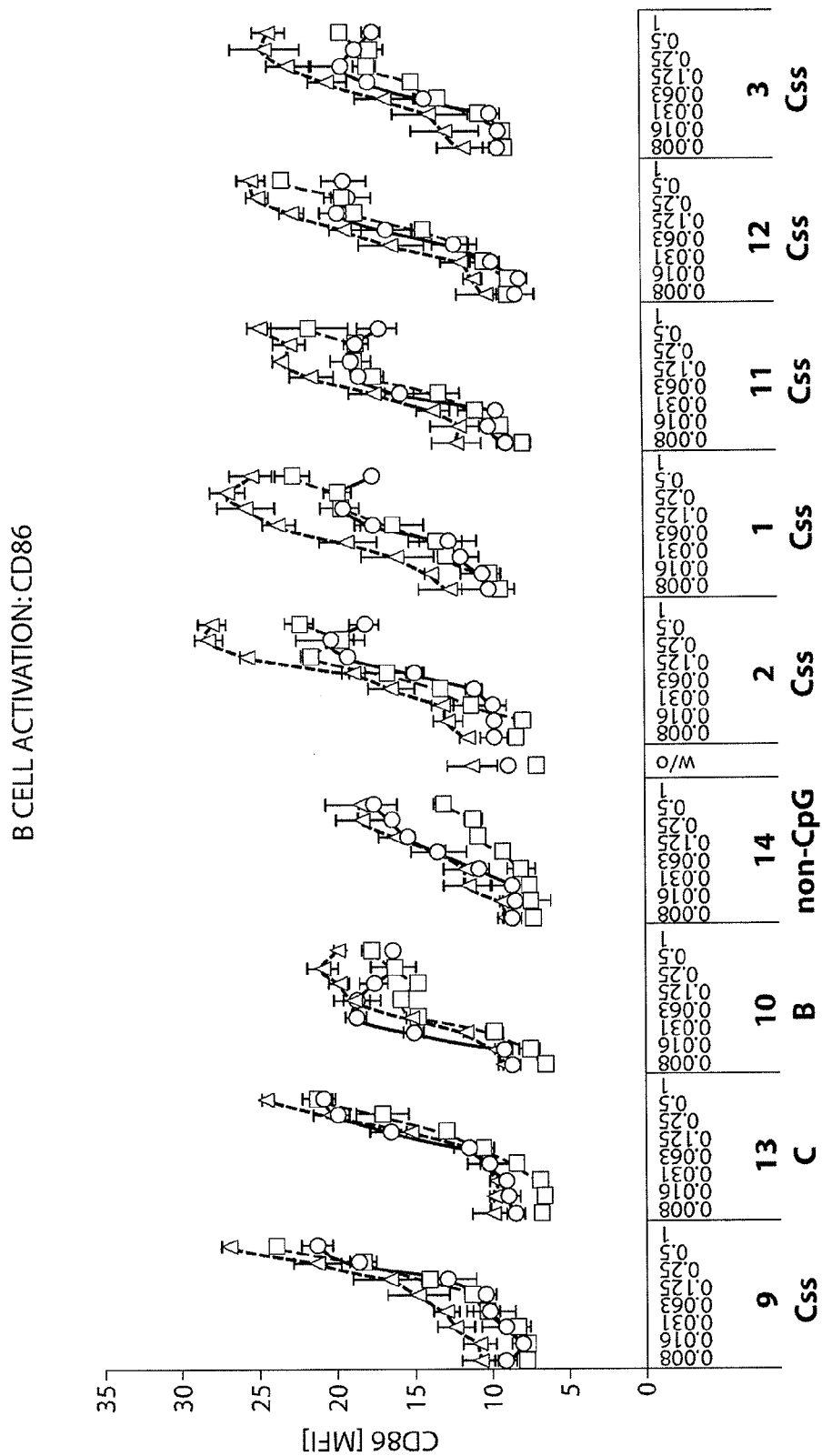
FIG. 34 is a set of graphs depicting CD86 expression on human PBMC following exposure of these cells to the oligonuelcotides for 48 hours listed by the SEQ ID NO along the bottom X-axis of the graph. The oligonucleotides shown in FIG. 34 include SEQ ID NO: 9, 13, 10, 14, 2, 1, 11, 12, and 3. The concentration of oligonucleotide used to produce a particular data point is depicted along the X-axis ($\mu$M). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD86, CD80, CD19, and CD14 and analyzed by flow cytometry. The data presented is the mean fluorescence intensity.
Figure 35:
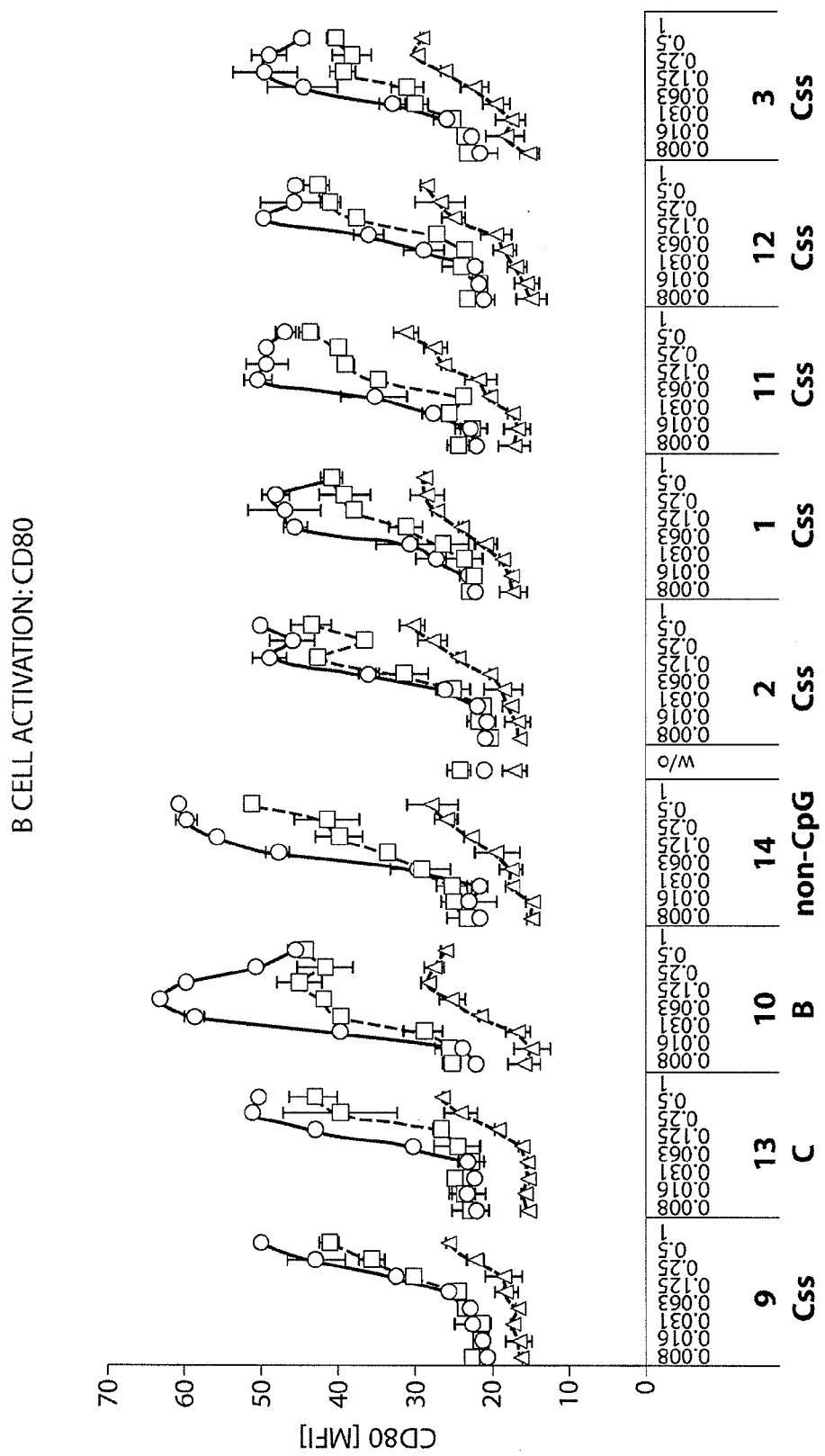
FIG. 35 is a set of graphs depicting CD86 expression on human PBMC following exposure of these cells to the oligonucleotides for 48 hours listed by the SEQ ID NO along the bottom X-axis of the graph. The oligonucleotides shown in FIG. 35 include SEQ ID NO: 9, 13, 10, 14, 2, 1, 11, 12, and 3. The concentration of oligonucleotide used to produce a particular data point is depicted along the X-axis ($\mu$M). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD86, CD80, CD19, and CD14 and analyzed by flow cytometry. The data presented is the mean fluorescence intensity.
Figure 36A:
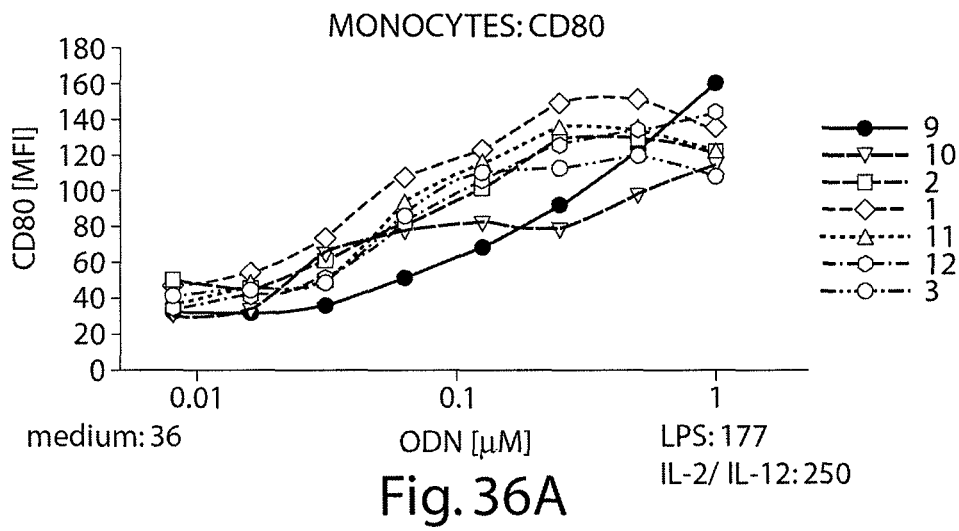
FIG. 36 is a set of graphs depicting levels of CD86 expression on plasmacytoid dendritic cells (36A) and CDS0 (36B) and CD86 (36C) expression on monocytes following exposure of these cells to the oligonucleotides listed by SEQ ID NO. in the key of the graph. Each data point is the calculated mean fluorescence intensity of three donors. The cells were incubated with the indicated ODN concentrations for 48 hours. Cells were stained and analyzed by flow cytometry.
Figure 36B:
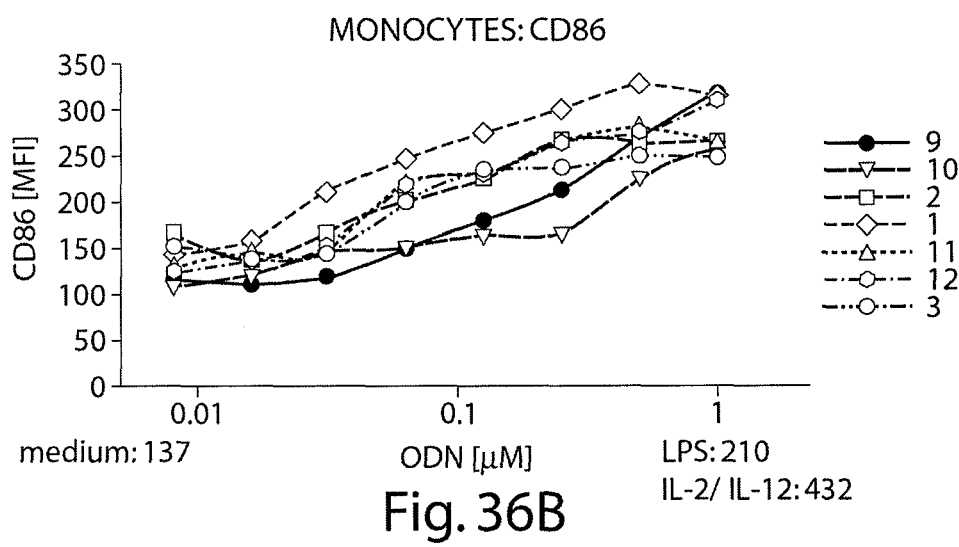
Figure 36C:
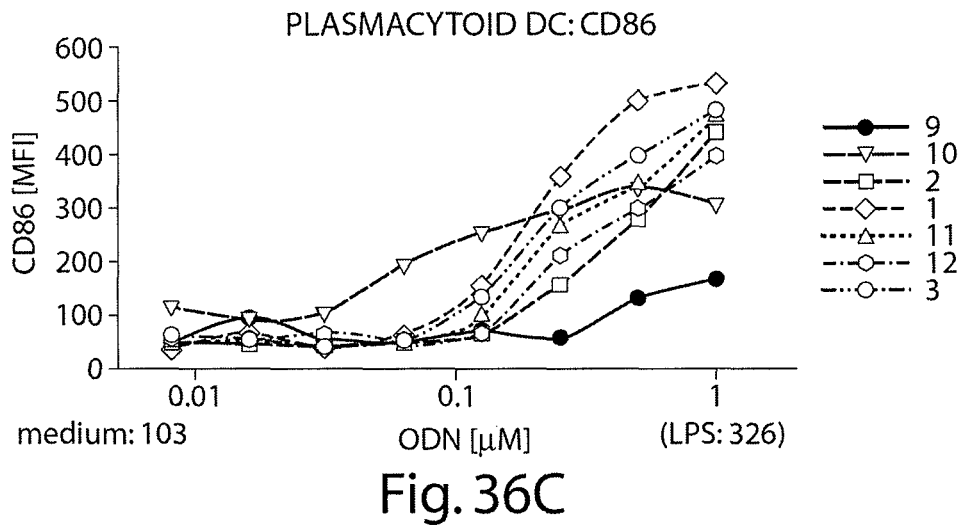
Figure 37:
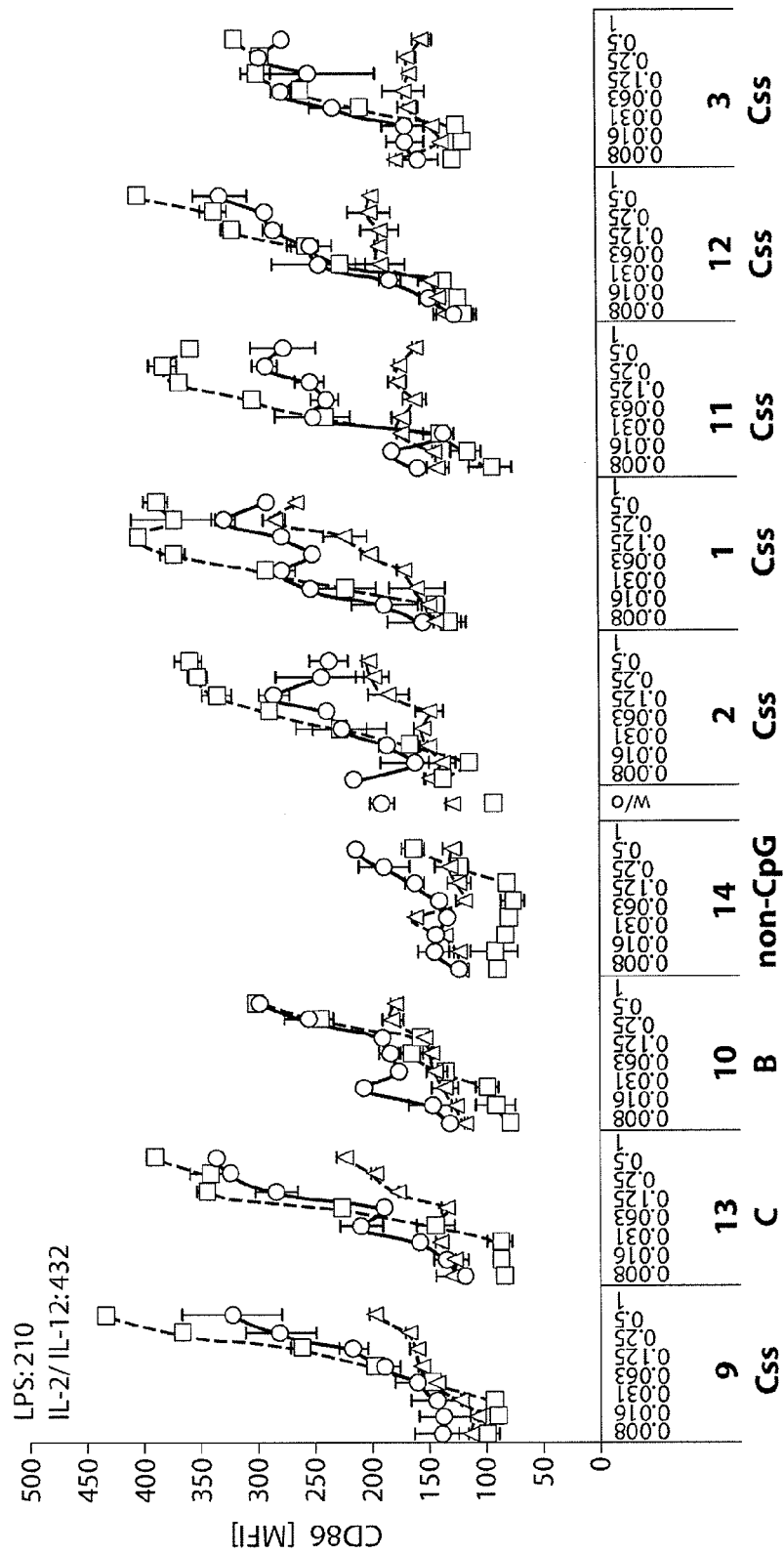
FIG. 37 is a set of graphs depicting levels of CD86 expression on monocytes following exposure of the cells to the oligonucleotides for 48 hours listed by the SEQ ID NO along the bottom X-axis of the graph. The oligonucleotides shown in FIG. 37 include SEQ ID NO: 9, 13, 10, 14, 2, 1, 11, 12, and 3. The concentration of oligonucleotide used to produce a particular data point is depicted along the X-axis ($\mu$M). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD86, CD80, CD19, and CD14 and analyzed by flow cytometry. The data presented is the mean fluorescence intensity.
Figure 38:
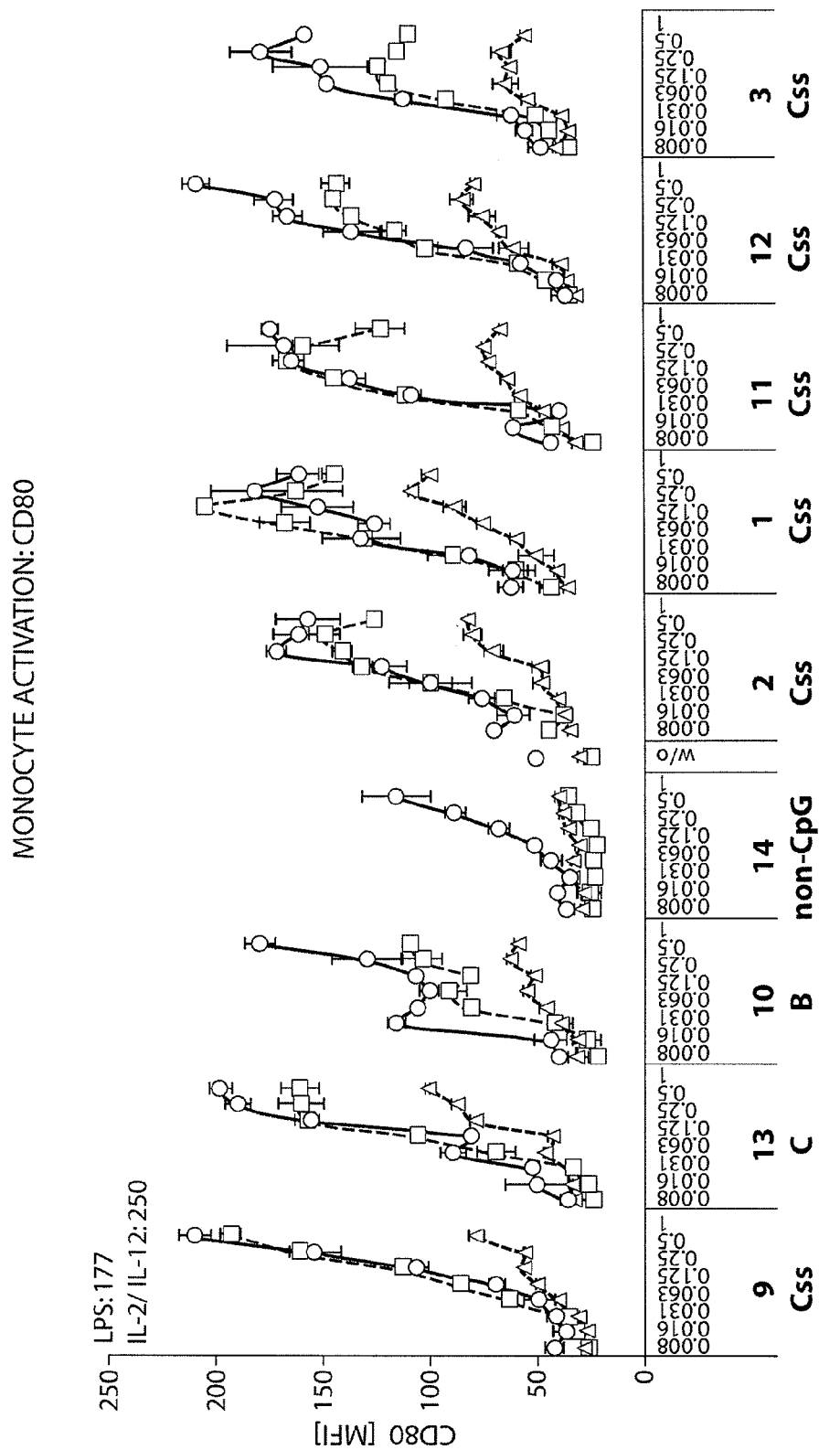
FIG. 38 is a set of graphs depicting CD80 expression on monocytes following exposure of these cells to the oligonucleotides for 48 hours listed by the SEQ ID NO along the bottom X-axis of the graph. The oligonucleotides shown in FIG. 38 include SEQ ID NO: 9, 13, 10, 14, 2, 1, 11, 12, and 3. The concentration of oligonucleotide used to produce a particular data point is depicted along the X-axis ($\mu$M). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD86, CD80, CD19, and CD14 and analyzed by flow cytometry. The data presented is the mean fluorescence intensity.
Figure 39:
FIG. 39 is a set of graphs depicting CD80 expression on plasmacytoid dendritic cells following exposure of these cells to the oligonucleotides for 48 hours listed by the SEQ ID NO along the bottom X-axis of the graph. The oligonucleotides shown in FIG. 37 include SEQ ID NO: 9, 13, 10, 14, 2, 1, 11, 12, and 3. The concentration of oligonucleotide used to produce a particular data point is depicted along the X-axis ($\mu$M). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD86, CD11c, CD123, and HLA-DR and analyzed by flow cytometry. The data presented is the mean fluorescence intensity.
Figure 40A:
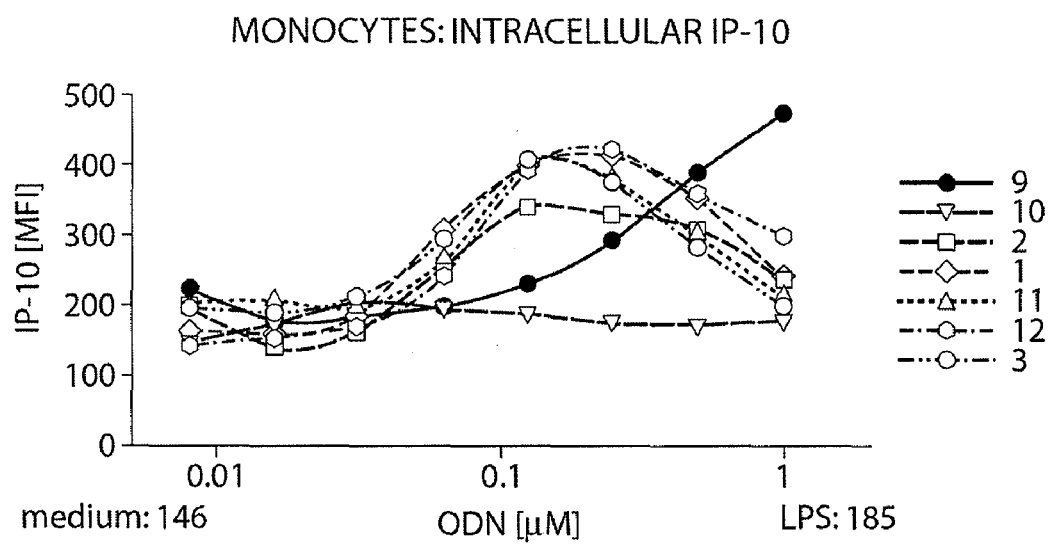
FIG. 40 is a set of graphs depicting levels of expression of intracellular IP-10 in B cells (40B) and monocytes (40A) following exposure of these cells to the oligonucleotides for 24 hours listed by SEQ ID NO. in the key of the graph. Each data point is the a calculated mean fluorescence intensity of three donors. The cells were incubated with the indicated ODN concentrations for 24 hours. Cells were stained and analyzed by flow cytometry.
Figure 40B:
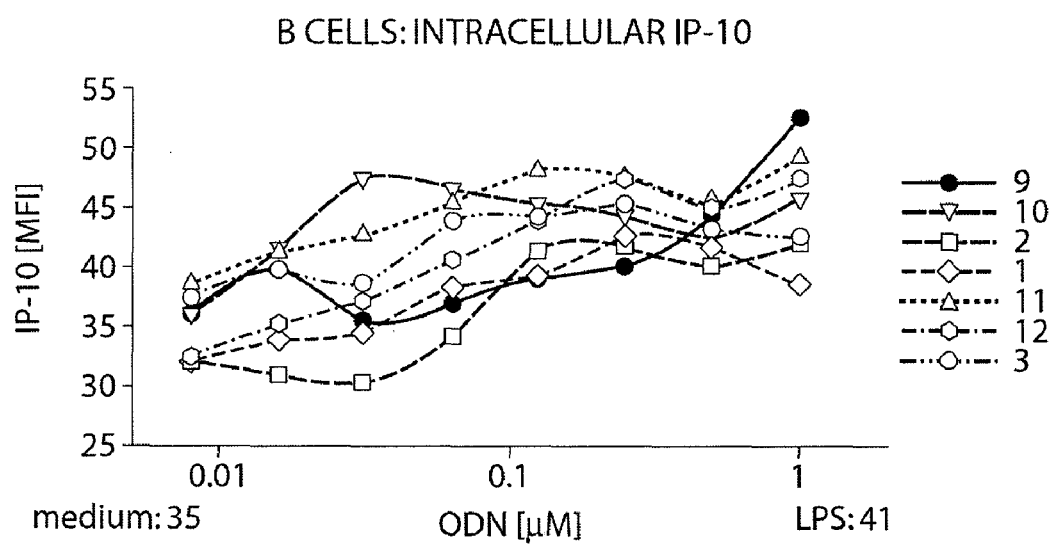
Figure 41:
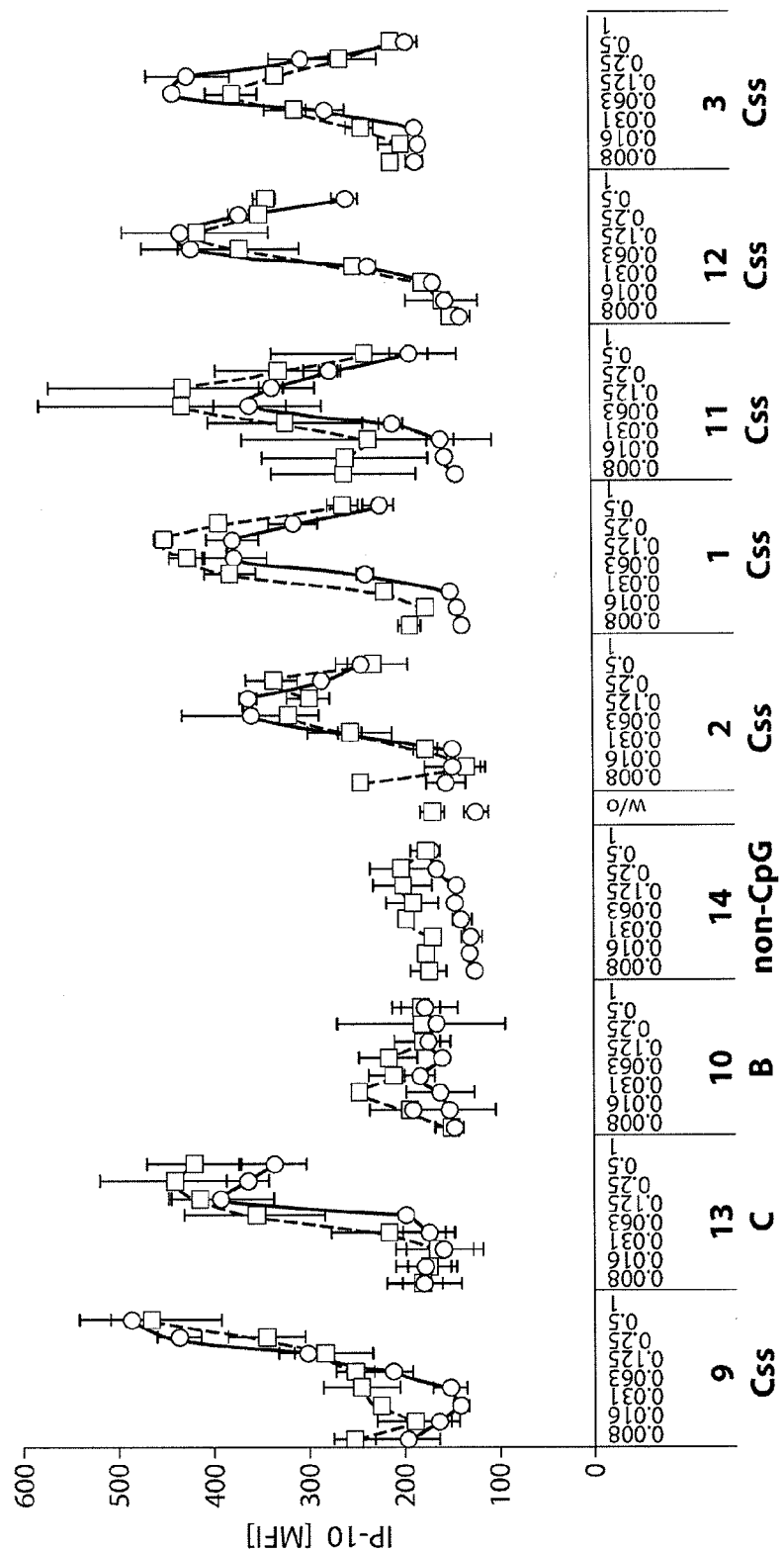
FIG. 41 is a set of graphs depicting levels of expression of intracellular IP-10 in monocytes following exposure of the cells to the oligonucleotides for 24 hours listed by the SEQ ID NO along the bottom X-axis of the graph. The oligonucleotides shown in FIG. 41 include SEQ ID NO: 9, 13, 10, 14, 2, 1, 11, 12, and 3. The concentration of oligonucleotide used to produce a particular data point is depicted along the X-axis ($\mu$M). The data represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD14, CD19, and IP-10 and analyzed by flow cytometry. The data presented is the mean fluorescence intensity.
Figure 42:
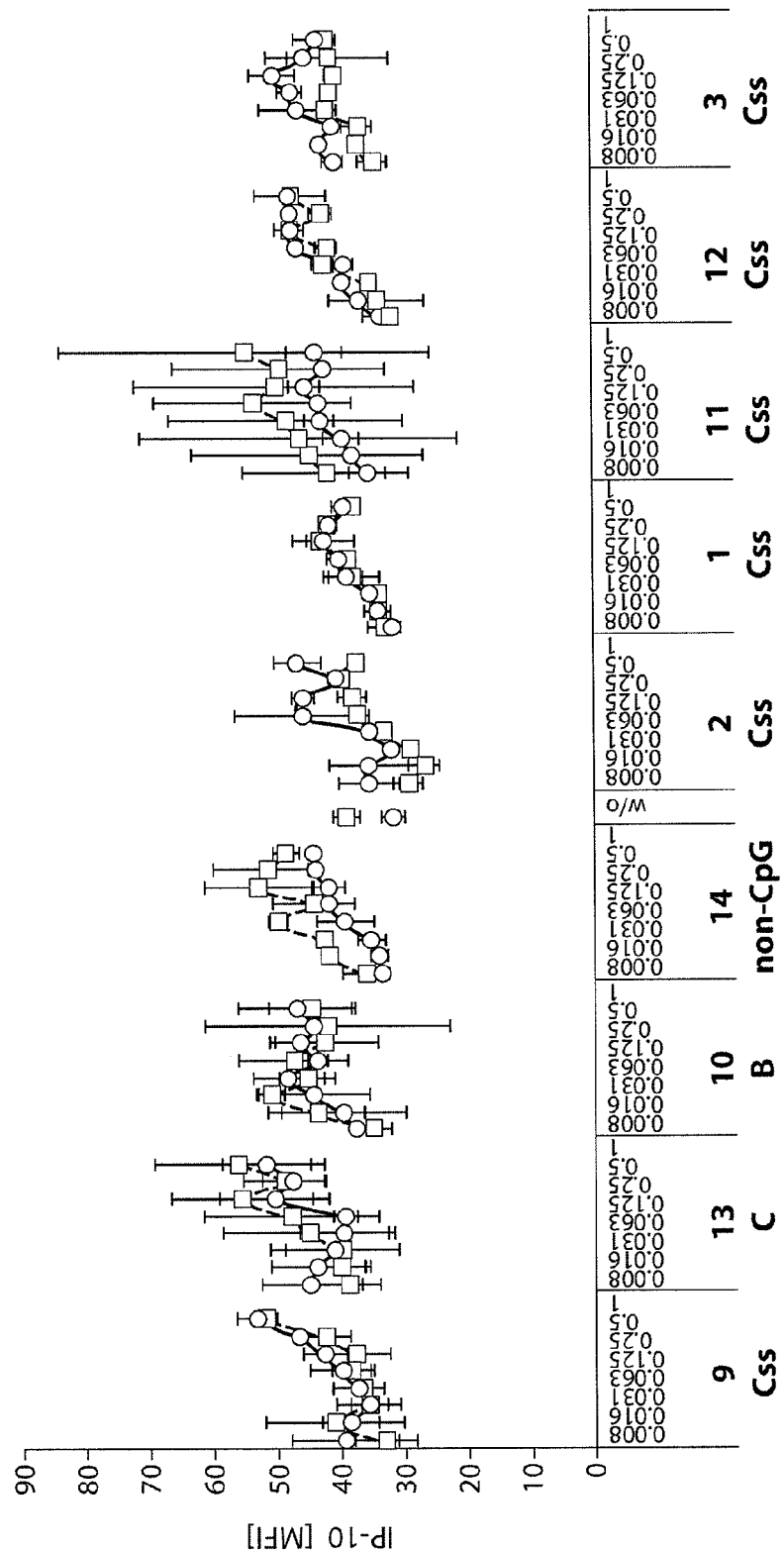
FIG. 42 is a set of graphs depicting levels of expression of intracellular IP-10 in B cells following exposure of these cells to the oligonucleotides for 24 hours listed by the SEQ ID NO along the bottom X-axis of the graph. The oligonucleotides shown in FIG. 42 include SEQ ID NO: 9, 13, 10, 14, 2, 1, 11, 12, and 3. The concentration of oligonucleotide used to produce a particular data point is depicted along the X-axis (µM). The data shown represents the values of three donors. Below the SEQ ID NOs is a designation referring to the class of ODN. Css=C-class semi soft, C=C-class, B=B-class, non-CpG=an ODN without an unmethylated CpG. The cells were stained with antibodies to CD14, CD19, and IP-10 and analyzed by flow cytometry. The data presented is the mean fluorescence intensity.
Figure 43A:
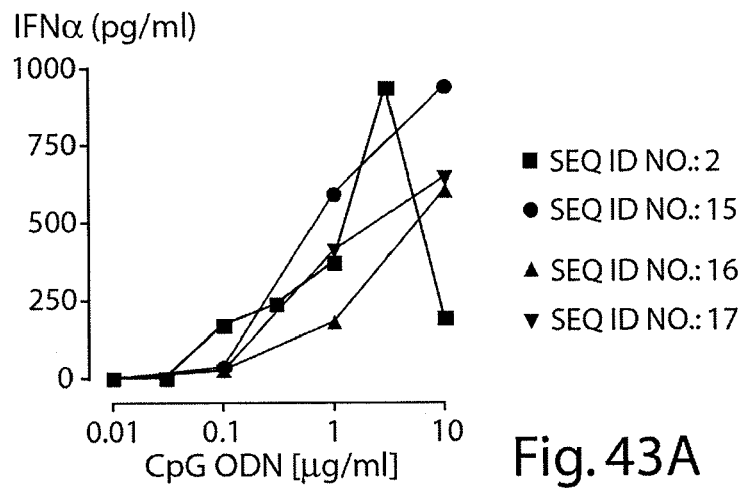
FIG. 43 is a set of graphs depicting a comparison of the abilities of SEQ ID NO.: 2 and fragments thereof (SEQ ID NO 15-17) to induce cytokine secretion from mouse splenocytes. The cytokines analyzed include IFNα (43A), IFNγ (43B), IP-10 (43C), IL-6 (43D), IL-10 (43E), and TNFα (43F).
Figure 43B:
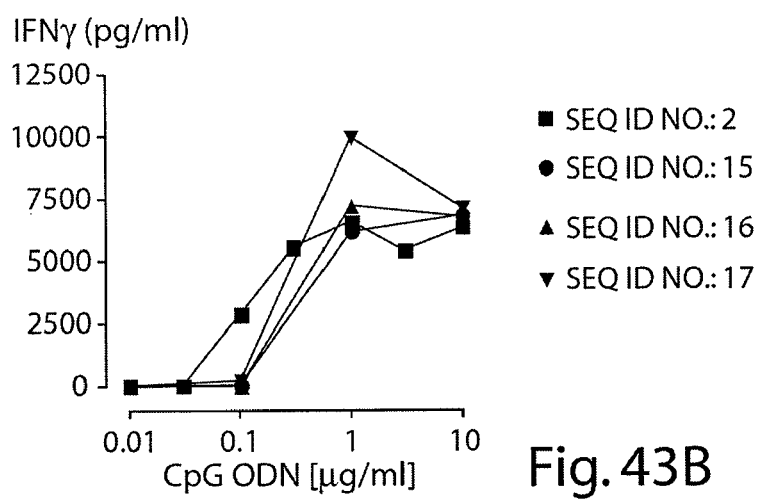
Figure 43C:
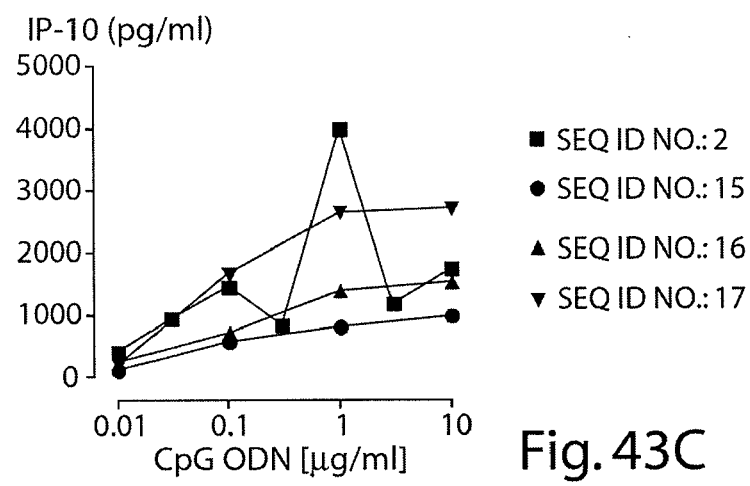
Figure 43D:
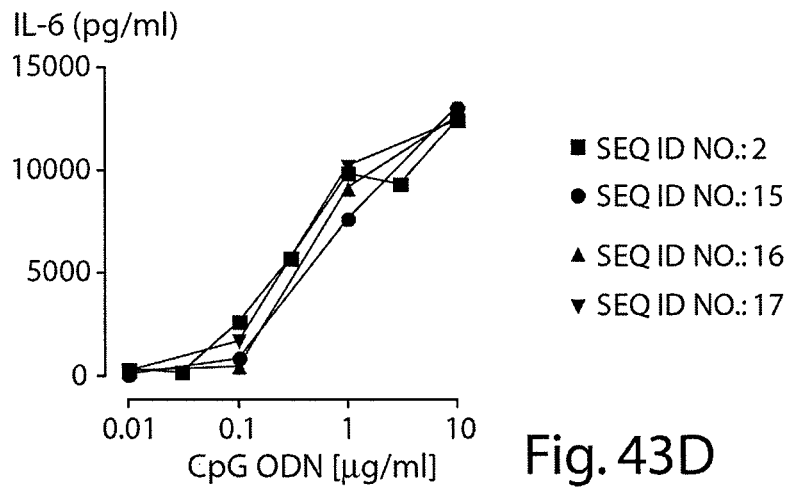
Figure 43E:
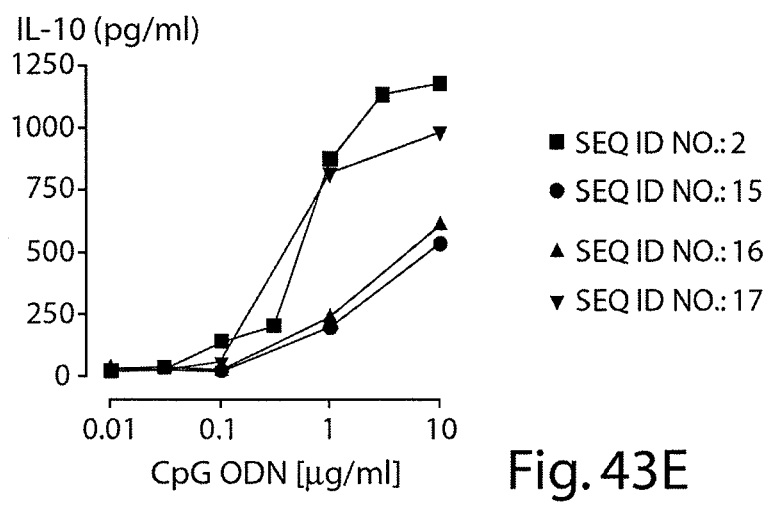
Figure 43F:
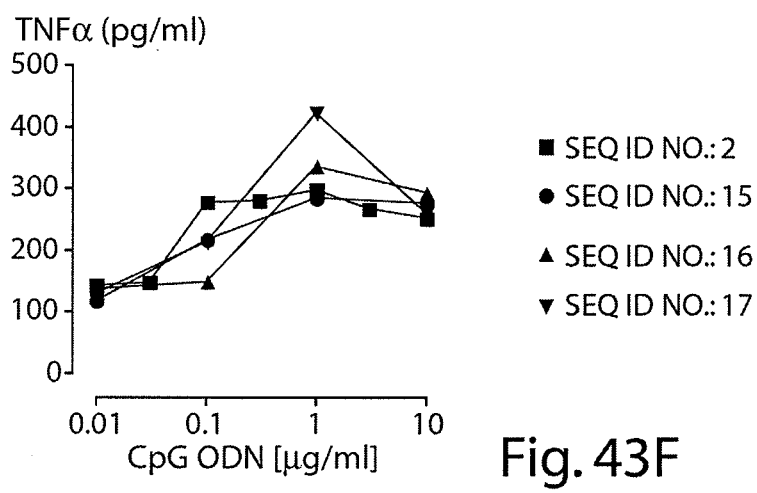
Figure 44A:
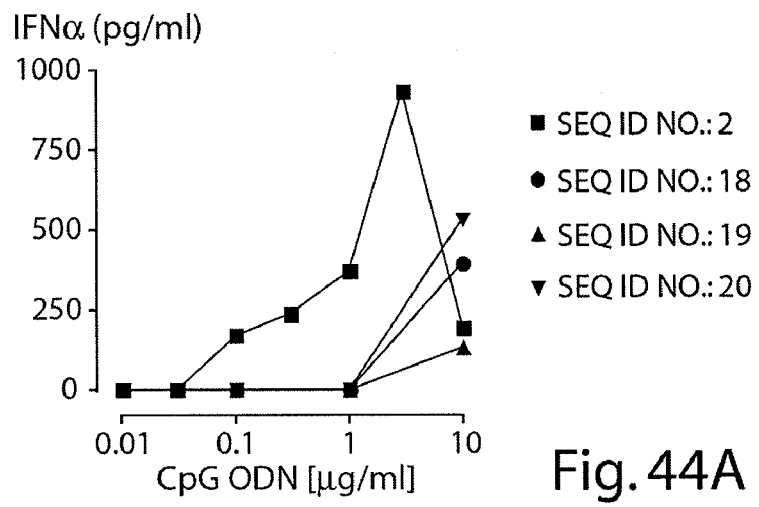
FIG. 44 is a set of graphs depicting a comparison of the abilities of SEQ ID NO.: 2 and fragments thereof (SEQ ID NO 18-20) to induce cytokine secretion from mouse splenocytes. The cytokines analyzed include IFNα (44A), IFNγ (44B), IP-10 (44C), IL-6 (44D), IL-10 (44E), and TNFα (44F).
Figure 44B:
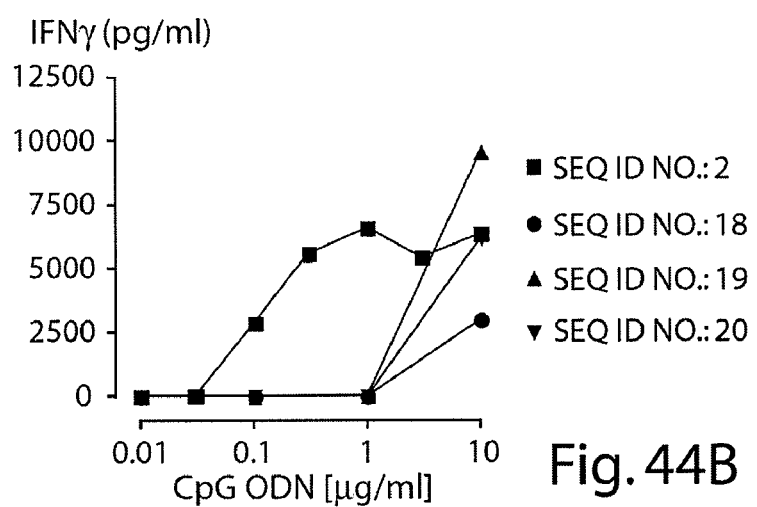
Figure 44C:
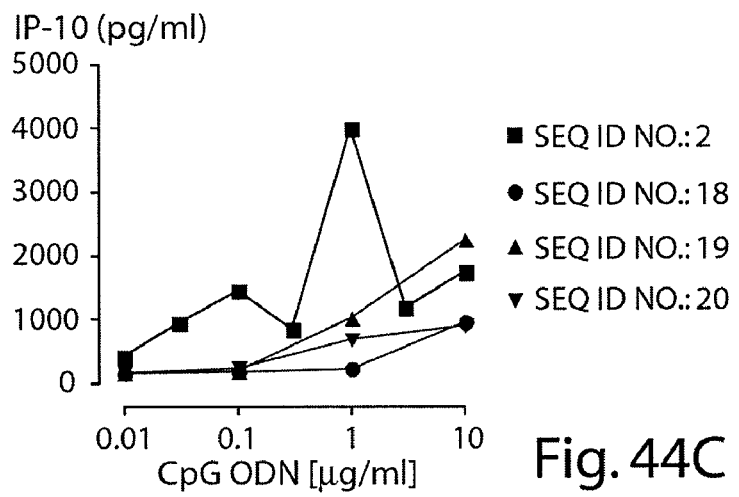
Figure 44D:
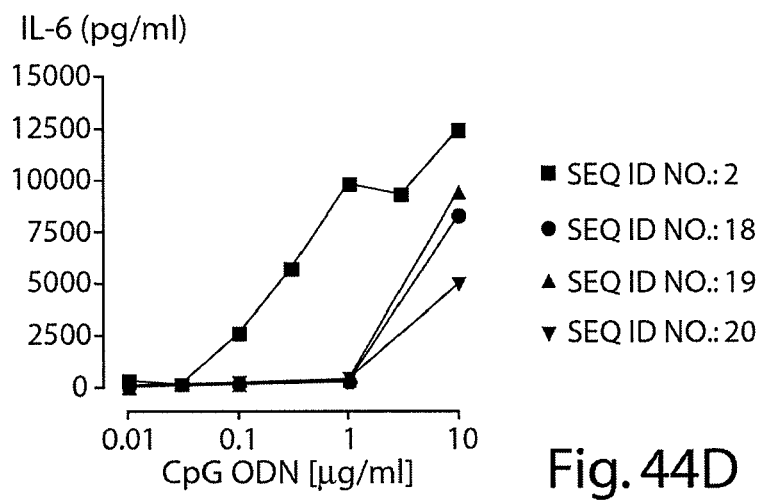
Figure 44E:
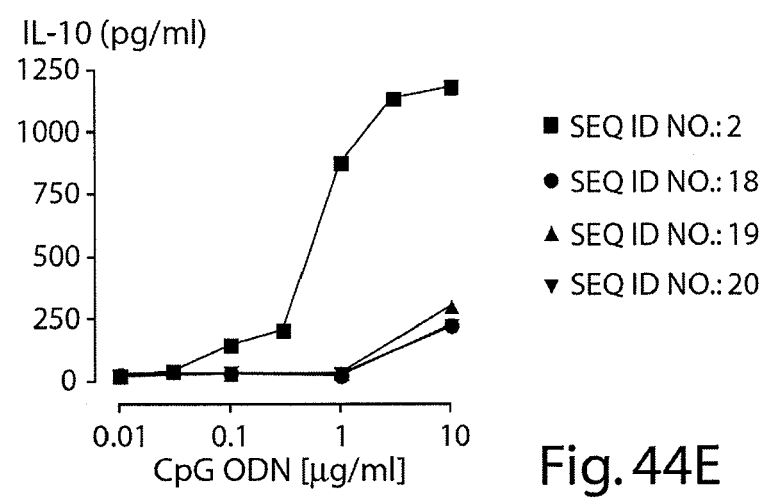
Figure 44F:
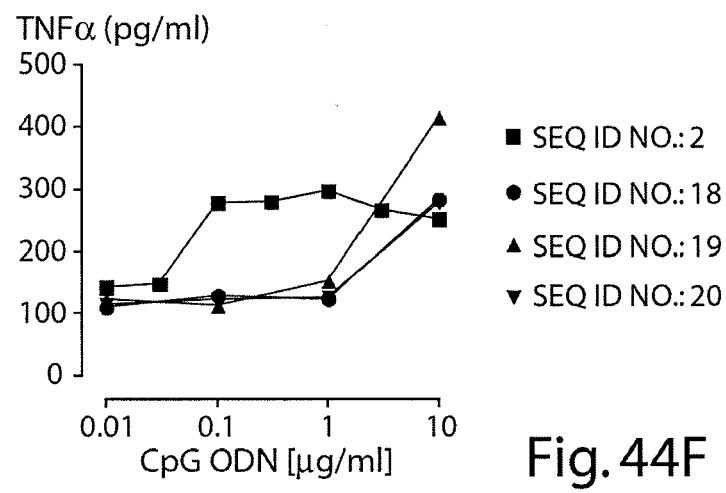
Figure 45A:
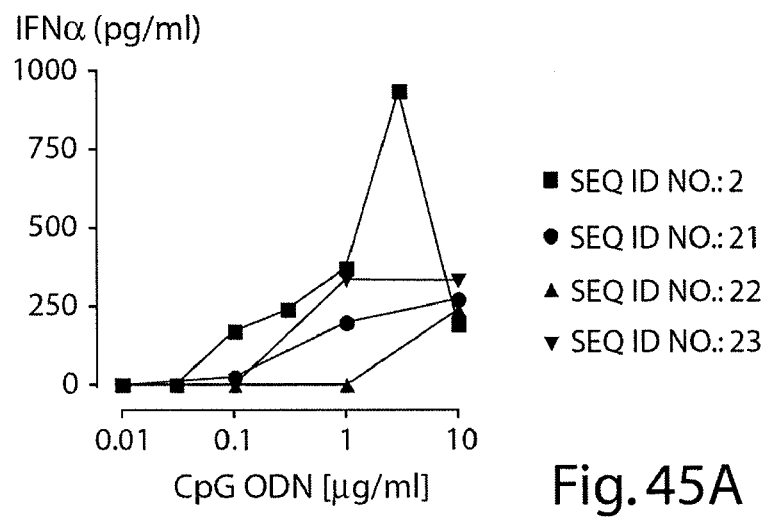
FIG. 45 is a set of graphs depicting a comparison of the abilities of SEQ ID NO.: 2 and fragments thereof (SEQ ID NO 21-23) to induce cytokine secretion from mouse splenocytes. The cytokines analyzed include IFNα (45A), IFNγ (45B), IP-10 (45C), IL-6 (45D), IL-10 (45E), and TNFα (45F).
Figure 45B:
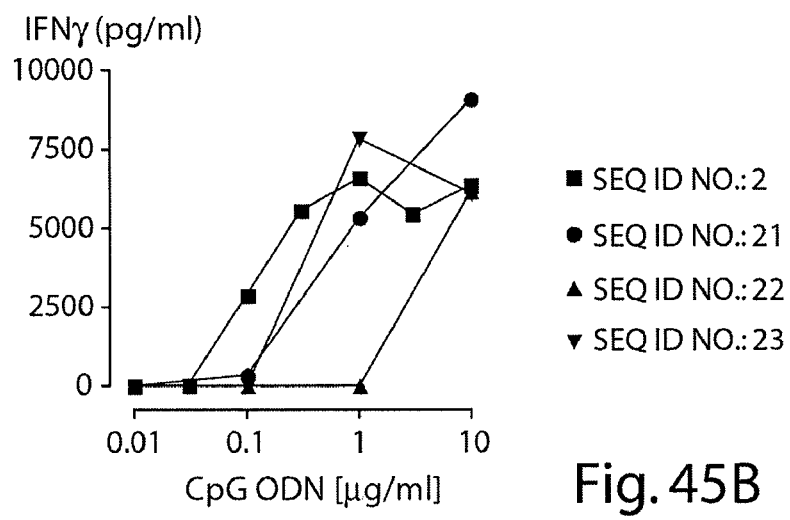
Figure 45C:
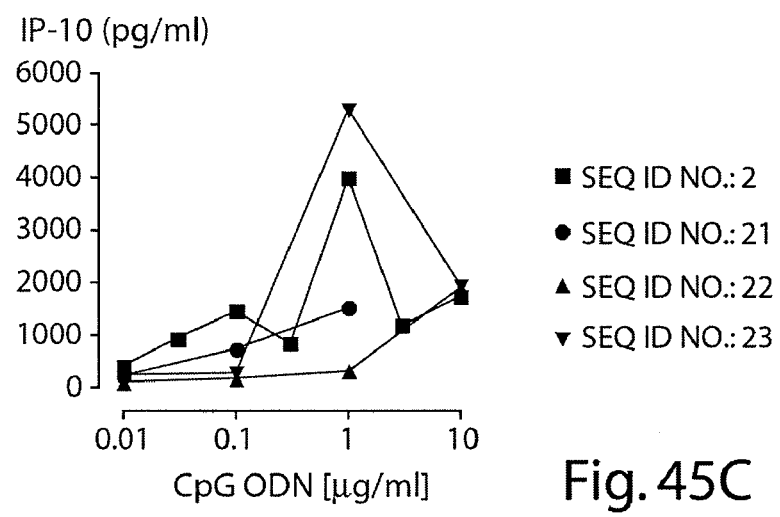
Figure 45D:
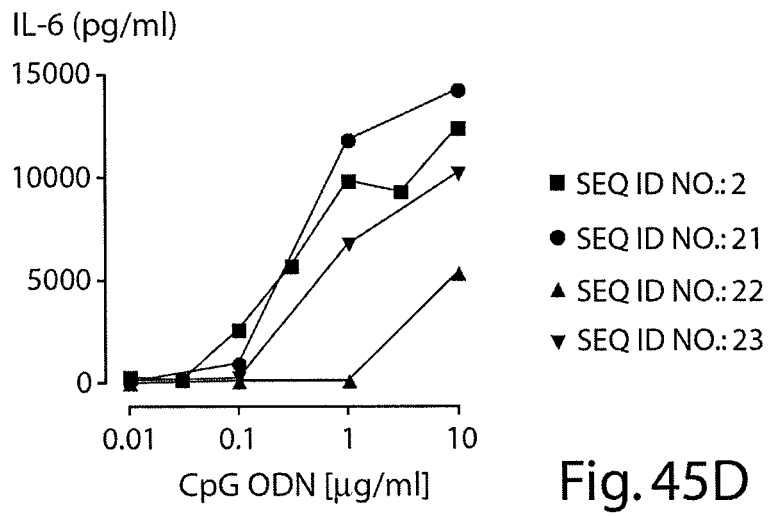
Figure 45E:
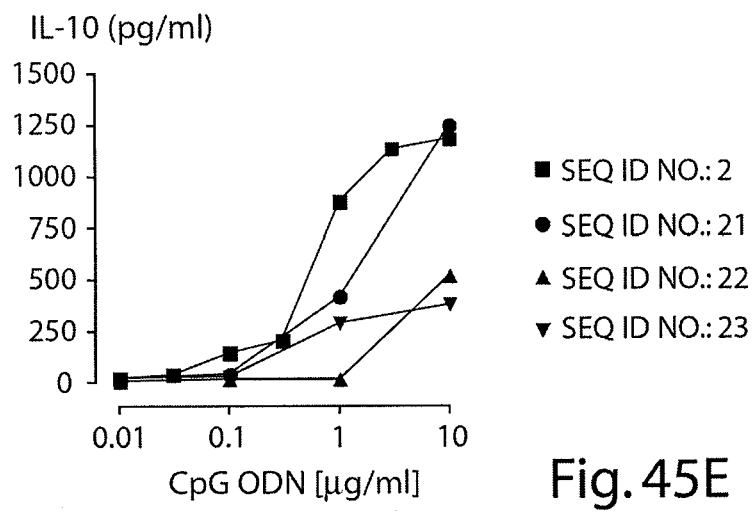
Figure 45F:
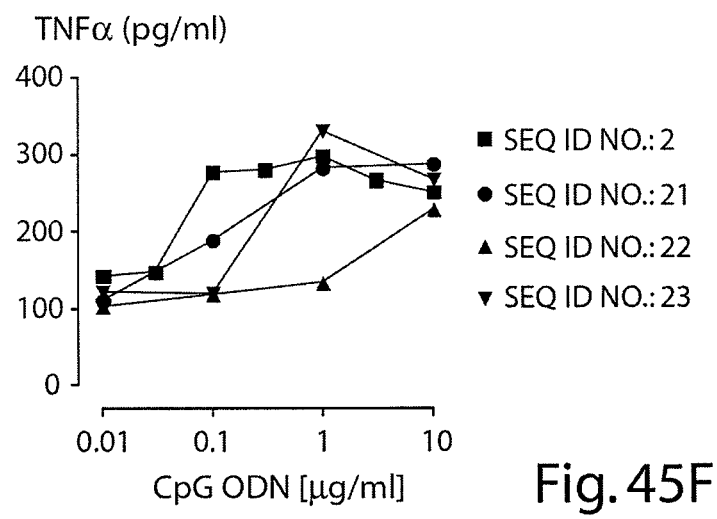

As demonstrated in FIGS. 32, 34, 35, 40, and 42 the CpG oligonucleotides tested in the assays were able activate B cells, as represented by the markers tested. In FIGS. 32 and 33 the CpG oligonucleotides tested in the assays were able activate NK cells, as represented by the markers tested. In FIGS. 36, 37, 40, and 41 the CpG oligonucleotides tested in the assays were able activate monocytes, as represented by the markers tested. In FIGS. 36 and 39 the CpG oligonucleotides tested in the assays were able activate plasmacytoid dendritic cells, as represented by the markers tested.

All five ODN having a semi soft backbone that were tested in the assays showed an increased potency in the assays (IFN-alpha, IP-10, IL-10) compared to SEQ ID NO. 9 (fully phosphorothioate backbone). The potency of these semi-soft ODN is also increased in: Monocyte activation (CD80, CD86 expression), pDC activation (CD86 expression), Intracellular IP-10 (Monocytes and B cells), IL-6 secretion, and B cell activation (CD80, CD86 expression). For instance, at approximately equivalent or lower concentrations most of the tested ODN resulted in better induction of the cell surface markers than the fully phosphorothioate SEQ ID NO. 9.

Example 13

The aim of this study was to investigate the biological activity of selected fragments (putative metabolites) of SEQ ID NO: 2. Activity was determined by measuring the ability of each fragment to induce secretion of TLR9-associated cytokines from mouse splenocytes in vivo.

Stimulation of cytokine secretion by fragments of SEQ ID NO.: 2 is shown in the attached FIGS. 43-45. The oligonucleotides examined are depicted in the Figures by SEQ ID NO and include SEQ ID NO: 15-23. The concentration of oligonucleotide used to produce a particular data point is depicted along the X-axis (µg/ml).

As demonstrated in FIGS. 43-45 SEQ ID NO: 2 and the fragments (putative metabolites, SEQ ID NOs:15-23) tested all induced the TLR9-associated cytokines IFNα, IFNγ, IP-0, IL-6, IL-10 and TNFα from mouse splenocytes in vitro (FIGS. 43, 44 and 45). This data demonstrates that each of the fragments retained biological activity.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A method for treating asthma, comprising administering to a subject having or at risk of having asthma an oligonucleotide comprising TCGTCGTCGTTCGGCGCGCGCCG (SEQ ID NO:2) in an effective amount to treat asthma.

2. A method for treating asthma exacerbated by viral infection, comprising administering to a subject having or at risk of having asthma exacerbated by viral infection an oligonucleotide comprising TCGTCGTCGTTCGGCGCGCGCCG (SEQ ID NO:2), in an effective amount to treat the asthma.

3. The method of claim 2, wherein the oligonucleotide is administered without an antigen to the subject.

4. The method of claim 1, wherein the oligonucleotide is delivered by a route selected from the group consisting of oral, nasal, sublingual, intravenous, subcutaneous, mucosal, respiratory, direct injection, and dermally.

5. A method for treating chronic obstructive pulmonary disease, comprising administering to a subject having or at risk of having chronic obstructive pulmonary disease an oligonucleotide comprising TCGTCGTCGTTCGGCGCGCGCCG (SEQ ID NO:2) in an effective amount to treat chronic obstructive pulmonary disease.

* * * * *